(12) United States Patent
Kakigami et al.

(10) Patent No.: US 7,345,180 B2
(45) Date of Patent: Mar. 18, 2008

(54) COMPOUND INHIBITING DIPEPTIDYL PEPTIDASE IV

(75) Inventors: Takuji Kakigami, Nagoya (JP); Mitsuru Oka, Nagoya (JP); Noriyasu Katoh, Nagoya (JP); Masahiro Yoshida, Nagoya (JP); Masahiro Shirai, Nagoya (JP); Toru Murase, Nagoya (JP); Masao Sakairi, Nagoya (JP); Takayo Murase, Nagoya (JP); Mitsuaki Takeuchi, Nagoya (JP); Yuji Hayashi, Nagoya (JP); Motohiro Takeda, Nagoya (JP); Mitsuhiro Makino, Nagoya (JP)

(73) Assignee: Sanwa Kagaku Kenkyusho Co., Ltd., Nagoya-Shi (JP)

( * ) Notice: Subject to any disclaimer, the term of this patent is extended or adjusted under 35 U.S.C. 154(b) by 0 days.

(21) Appl. No.: 10/541,108

(22) PCT Filed: Jan. 30, 2004

(86) PCT No.: PCT/JP2004/000886

§ 371 (c)(1),
(2), (4) Date: Feb. 1, 2006

(87) PCT Pub. No.: WO2004/067509

PCT Pub. Date: Aug. 12, 2004

(65) Prior Publication Data

US 2006/0229286 A1    Oct. 12, 2006

(30) Foreign Application Priority Data

Jan. 31, 2003   (JP) .............................. 2003-023077

(51) Int. Cl.
*C07D 487/04* (2006.01)
*C07D 277/06* (2006.01)
*C07D 209/04* (2006.01)

(52) U.S. Cl. ...................... 548/453; 548/200; 548/469

(58) Field of Classification Search ................ 548/453, 548/200, 469
See application file for complete search history.

(56) References Cited

U.S. PATENT DOCUMENTS

| | | | |
|---|---|---|---|
| 4,528,282 A * | 7/1985 | Preston et al. ................. 514/19 |
| 5,416,093 A * | 5/1995 | Shuman ....................... 514/307 |
| 5,939,560 A | 8/1999 | Jenkins et al. | |
| 6,011,155 A | 1/2000 | Villhauer | |
| 6,303,661 B1 | 10/2001 | Demuth et al. | |
| 2002/0193390 A1 | 12/2002 | Villhauer | |
| 2004/0180925 A1 | 9/2004 | Matsuno et al. | |

FOREIGN PATENT DOCUMENTS

| | | |
|---|---|---|
| EP | 1 354 882 | 10/2003 |
| JP | 09-509921 | 10/1997 |
| WO | 97/40832 | 11/1997 |
| WO | 01/96295 | 12/2001 |
| WO | 02/051836 | 7/2002 |

OTHER PUBLICATIONS

Lupus erythematosus [online], [retrieved on Dec. 28, 2006]. Retrieved from the Internet, URL; http://en.wikipedia.org/wiki/Lupus_erythematosus>.*
Edwin B. Villhauer, Gary M. Coppola, and Thomas E. Hughes, Novartis Institute for Biomedical Research, Summit, NJ 07901, "Chapter 19. DPP-IV Inhibition and Therapeutic Potential," Section IV—Immunology, Endocrinology and Metabolic Deseases, Hagmann, Ed., Annual Reports in Medicinal Chemistry-36, pp. 191-200, Copyright © 2001 by Academic Press.

* cited by examiner

*Primary Examiner*—Rebecca Anderson
*Assistant Examiner*—Shawquia Young
(74) *Attorney, Agent, or Firm*—Burr & Brown

(57) ABSTRACT

A dipeptidyl peptidase IV inhibitor which is satisfactory in respect of activity, stability and safety and has an excellent action as a pharmaceutical agent. A compound represented by the following general formula or a pharmaceutically acceptable salt thereof:

(I)

wherein $R^1$ and $R^2$ each represents hydrogen, an optionally substituted C1-6 alkyl group, or —COOR$^5$ whereupon $R^5$ represents hydrogen or an optionally substituted C1-6 alkyl group, or $R^1$, $R^2$, and a carbon atom together represent a 3- to 6-membered cycloalkyl group, $R^3$ represents hydrogen or an optionally substituted C6-10 aryl group, $R^4$ represents a hydrogen or a cyano group, D represents —CONR$^6$-, —CO— or —NR$^6$CO—, $R^6$ represents hydrogen or an optionally substituted C1-6 alkyl group, E represents —(CH$_2$)$_m$— whereupon m is 1 to 3, —CH$_2$OCH$_2$—, or —SCH$_2$—, n is 0 to 3, and A represents an optionally substituted bicyclic heterocyclic group or bicyclic hydrocarbon group.

15 Claims, No Drawings

COMPOUND INHIBITING DIPEPTIDYL PEPTIDASE IV

CROSS REFERENCE TO RELATED APPLICATION

This application is a National Phase of International Application No. PCT/JP2004/000886 having an international filing date of Jan. 30, 2004, published in Japanese on Aug. 12, 2004, which claims the benefit of Japanese Application 2003-023077, filed Jan. 31, 2003, the entirety of which is incorporated herein by reference.

TECHNICAL FIELD

The present invention relates to a compound which has an excellent inhibitory effect on dipeptidyl peptidase IV (abbreviated hereinafter to DPP-IV) and is useful for treatment and prevention of type 2 diabetes, treatment or prevention of its related complications, or treatment of other pathologic condition associated with DPP-IV, or pharmaceutically acceptable salts thereof.

BACKGROUND ART

DPP-IV is one kind of serine protease hydrolyzing a dipeptide Xaa-Pro or Xaa-Ala (Xaa may be any amino acid) specifically from the N-end of a polypeptide chain. The role of DPP-IV (also called CD26) in vivo and the relationship of this enzyme with diseases are not completely elucidated, but there are many reports thereon. In particular, attention is paid recently to the role of DPP-IV as an enzyme participating in the inactivation of glucagon-like peptide 1 (abbreviated hereinafter to GLP-1).

GLP-1 is a peptide hormone which without inducing insulin secretion by itself, has an action of increasing insulin secretion induced by glucose. Accordingly, its enhancement of insulin secretion depending on blood glucose level can be expected with less possibility of hypoglycemia. Further, there is also a report suggesting that GLP-1 has an appetite suppressing action. However, GLP-1 is rapidly cleaved by DPP-IV, so GLP-1 itself is hardly applicable as medicine. Accordingly, peptide analogues of GLP-1 have been examined, but any of such analogues are injections, but are not preparations for oral administration.

Under these circumstances, inhibition of the cleavage enzyme DPP-IV was anticipated in order to prevent the degradation of GLP-1 thereby enhancing the activity of GLP-1. This involves orally administering a DPP-IV inhibitor thereby keeping the concentration of GLP-1 intact in vivo to prevent and treat diabetes and the like, particularly type 2 diabetes, by the action of GLP-1. Such treatment method is also expected to have an effect of preventing or treating other diseases induced or developed by impaired glucose tolerance, for example, hyperglycemia (postprandial hyperglycemia), hyperinsulinemia, diabetic complications (renal diseases, neuropathy and the like), abnormal lipid metabolism, obesity and the like. Further, its effect on prevention or treatment of diseases expected to be ameliorated by enhancing the inhibition of food intake of GLP-1, for example, bulimia, obesity and the like can also be expected.

On the other hand, the reported action of DPP-IV further includes cleavage of neuropeptides, activation of T cells, adhesion of metastatic tumor cells to endothelium, and invasion of HIV virus into lymphocytes. It is found with respect to DPP-IV and known that the positiveness of DPP-IV is increased in peripheral blood T cells from patients with rheumatism and the activity of DPP-IV is high in urine from patients with nephritis. Accordingly, a substance inhibiting DPP-IV is expected to have an effect of preventing or treating autoimmune diseases (for example, arthritis, rheumatoid arthritis), osteoporosis, acquired immune deficiency syndrome (AIDS), rejection of transplanted organs and tissues, and the like.

Patent applications relating to DPP-IV inhibitors have also been already filed. WO02/51836, WO01/96295, US20020193390, U.S. Pat. No. 6,011,155 and Japanese Patent Application National Publication No. 9-509921 disclose 2-cyanopyrrolidine derivatives, and WO97/40832 discloses aminoacyl thiazolidide derivatives. In addition to the compound group described above, Annual Report in Medicinal Chemistry, Vol. 36, pp. 191-200 (2001) reports peptide derivatives such as aminoacyl pyrrolidide derivative, dipeptide phosphonate derivative, dipeptide borate derivative, tetrahydroisoquinoline derivative and cyclic peptide derivative, and non-peptide derivatives such as N-phenylphthalimide derivative, N-phenylhomophthalimide derivative and isoquinoline derivative.

DISCLOSURE OF THE INVENTION

Up to now, many DPP-IV inhibitors have been reported, but any compounds cannot be said to be sufficient in respect of inhibitory activity, stability and safety, and are not satisfactory as pharmaceutical preparations. Accordingly, there is demand for development of compounds which have a therapeutic or prophylactic effect attributable to an inhibitory action on DPP-IV and are sufficiently satisfactory as pharmaceutical agents.

In view of the circumstances described above, the present inventors made earnest study for the purpose of development of novel DPP-IV inhibitors. As a result, the present inventors have found that a compound represented by the general formula below having a suitably hydrophobic bicyclic ring, particularly a bicyclic heterocyclic group, in its side chain has a potent inhibitory activity on DPP-IV, and have developed the compound to further increase its stability, thus completing the present invention.

That is, the present invention provides a compound represented by the following formula:

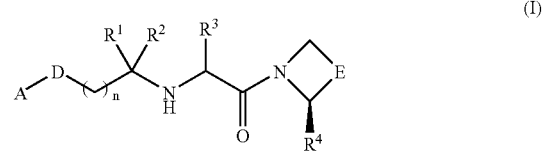

(I)

(wherein $R^1$ and $R^2$ are the same or different and each represents a hydrogen atom, an optionally substituted C1-6 alkyl group, or —COOR$^5$ whereupon $R^5$ represents a hydrogen atom or an optionally substituted C1-6 alkyl group, or $R^1$ and $R^2$, together with a carbon atom to which they are bound, represent a 3- to 6-membered cycloalkyl group, $R^3$ represents a hydrogen atom or an optionally substituted C6-10 aryl group, $R^4$ represents a hydrogen atom or a cyano group, D represents —CONR$^6$—, —CO— or —NR$^6$CO—, $R^6$ represents a hydrogen atom or an optionally substituted C1-6 alkyl group, E represents —(CH$_2$)$_m$— whereupon m is an integer of 1 to 3, —CH$_2$OCH$_2$—, or —SCH$_2$—, n is an integer of 0 to 3, and A represents an optionally substituted bicyclic heterocyclic group or bicyclic hydrocarbon group), or a pharmaceutically acceptable salt thereof, and in this specification, such compound is referred to hereinafter as "the compound of the present invention".

The present invention also provides a DPP-IV inhibitor comprising the compound of the present invention as an active ingredient. The DPP-IV inhibitor serves as a prophylactic or therapeutic agent for diseases whose morbid state is expected to be ameliorated by inhibiting the activity of DPP-IV, for example, diabetes (particularly type 2 diabetes), diabetic complications and the like.

BEST MODE FOR CARRYING OUT THE INVENTION

The DPP-IV inhibitor of the present invention is described in more detail below. The compound of the present invention is a compound represented by the following formula:

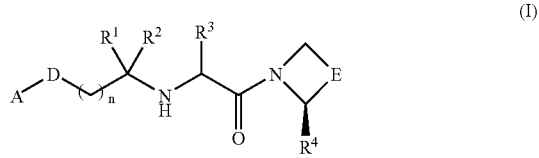

(I)

(wherein $R^1$ and $R^2$ are the same or different and each represents a hydrogen atom, an optionally substituted C1-6 alkyl group, or —COOR$^5$ whereupon $R^5$ represents a hydrogen atom or an optionally substituted C1-6 alkyl group, or $R^1$ and $R^2$, together with a carbon atom to which they are bound, represent a 3- to 6-membered cycloalkyl group, $R^3$ represents a hydrogen atom or an optionally substituted C6-10 aryl group, $R^4$ represents a hydrogen atom or a cyano group, D represents —CONR$^6$—, —CO— or —NR$^6$CO—, $R^6$ represents a hydrogen atom or an optionally substituted C1-6 alkyl group, E represents —(CH$_2$)$_m$— where upon m is an integer of 1 to 3, —CH$_2$OCH$_2$—, or —SCH$_2$—, n is an integer of 0 to 3, and A represents an optionally substituted bicyclic heterocyclic group or bicyclic hydrocarbon group), or a pharmaceutically acceptable salt thereof. Hereinafter, each symbol used in this specification is described in more detail.

The optionally substituted C1-6 alkyl group means that an arbitrary (throughout this specification, the term "arbitrary" refers not only to one atom or group but also to multiple atoms or groups) hydrogen atom of the C1-6 alkyl group may be substituted with a halogen atom (for example, a fluorine, chlorine, bromine or iodine atom), an oxo group, a nitro group, a cyano group, a phenyl group, —OR$^{14}$, —NR$^{15}$R$^{16}$, —OCOR$^{17}$, NHCOR$^{18}$, —NHS(O$_2$)R$^{19}$ or —S (O$_2$) NR$^{20}$R$^{21}$ wherein R$^{14}$, R$^{17}$, R$^{18}$ and R$^{19}$ each represents a hydrogen atom, a C1-6 alkyl group, a phenyl group or a benzyl group, R$^{15}$, R$^{16}$, R$^{20}$ and R$^{21}$ are the same or different and each represents a hydrogen atom, a C1-6 alkyl group or a phenyl group, or R$^{15}$ and R$^{16}$, or R$^{20}$ and R$^{21}$, may be combined with each other to form a 3- to 6-membered alicyclic ring. Specific examples of the C1-6 alkyl group include linear, branched or cyclic alkyl groups such as methyl, ethyl, propyl, isopropyl, butyl, isobutyl, s-butyl, t-butyl, cyclobutyl, pentyl, isopentyl, neopentyl, t-pentyl, cyclopentyl, hexyl, cyclohexyl and the like. Among these groups, C1-3 alkyl groups are preferable.

The optionally substituted C1-6 alkoxy group means that an arbitrary hydrogen atom of the C1-6 alkoxy group may be substituted with a halogen atom (for example, a fluorine, chlorine, bromine or iodine atom), an oxo group, a nitro group, a cyano group, a phenyl group, —OR$^{14}$, —NR$^{15}$R$^{16}$, —OCOR$^{17}$, NHCOR$^{18}$, —NHS(O$_2$)R$^{19}$ or —S (O$_2$) NR$^{20}$R$^{21}$ wherein R$^{14}$, R$^{15}$, R$^{16}$, R$^{17}$, R$^{18}$, R$^{19}$, R$^{20}$ and R$^{21}$ have the same meaning as defined above. Specific examples of the C1-6 alkoxy group include linear, branched or cyclic alkoxy groups such as methoxy, ethoxy, propoxy, isopropoxy, cyclopropoxy, butoxy, isobutoxy, s-butoxy, t-butoxy, cyclobutoxy, pentyloxy, isopentyloxy, neopentyloxy, t-pentyloxy, cyclopentyloxy, hexyloxy, cyclohexyloxy and the like. Among these groups, C1-3 alkoxy groups are preferable.

The optionally substituted C6-10 aryl group means that an arbitrary hydrogen atom on the ring of the aryl group may be substituted with a C1-6alkyl group, a halogen atom (for example, a fluorine, chlorine, bromine or iodine atom), an oxo group, a nitro group, a cyano group, a phenyl group, —OR$^{14}$, —NR$^{15}$R$^{16}$, —OCOR$^{17}$, NHCOR$^{18}$, —NHS(O$^2$) R$^{19}$ or —S(O$_2$)NR$^{20}$R$^{21}$ wherein R$^{14}$, R$^{15}$, R$^{16}$, R$^{17}$, R$^{18}$, R$^{19}$, R$^{20}$ and R$^{21}$ have the same meaning as defined above. Preferable examples of the aryl group include phenyl, naphthyl, and a bicyclic group (for example indanyl or the like) having a 6-membered ring condensed with a 5-, 6- or 7-membered ring, at least one ring of which is an aromatic ring.

The optionally substituted bicyclic heterocyclic group means that an arbitrary hydrogen atom on the ring of the bicyclic heterocyclic group may be substituted with an optionally substituted C1-6 alkyl group, an optionally substituted C1-6 alkoxy group, a halogen atom (for example, a fluorine, chlorine, bromine or iodine atom), an oxo group, a nitro group, a cyano group, a phenyl group, —OR$^{14}$, —NR$^{15}$R$^{16}$, —OCOR$^{17}$, NHCOR$^{18}$, —NHS(O$_2$) R$^{19}$ or —S(O$^2$)NR$^{20}$OR$^{21}$ wherein R$^{14}$, R$^{15}$, R$^{16}$, R$^{17}$, R$^{18}$, R$^{19}$, R$^{20}$ and R$^{21}$ have the same meaning as defined above. Preferable examples of the bicyclic heterocyclic group include a bicyclic heterocyclic group having a 6-membered ring having carbons and 1 to 4 heteroatoms (oxygen, nitrogen, sulfur atom) condensed with a 5-, 6- or 7-membered ring, particularly, a benz derivative, pyridyl derivative and pyrimidyl derivative. Examples thereof include indolyl, benzothiazolyl, benzoimidazolyl, benzoxazolyl, pyrazolopyridinyl, imidazopyridinyl, pyrazolopyrimidinyl, triazolopyrimidinyl, benzotriazolyl, benzofuranyl, isobenzofuranyl, benzothiophenyl, benzisoxazolyl, benzoisothiazolyl, triazolopyrimidinyl, quinolinyl, isoquinolinyl, cinnolinyl, chromenyl, pyridopyrimidinyl, quinazolinyl, quinoxalinyl, naphthyridinyl, thianaphthenyl, isothianaphthenyl, dihydroindolyl, dihydroisoindolyl, dihydropurinyl, dihydrothiazolopyrimidinyl, dihydrobenzodioxanyl, isoindolinyl, indazolyl, pyrrolopyridinyl, tetrahydroquinolinyl, decahydroquinolinyl, tetrahydroisoquinolinyl, decahydroisoquinolinyl, tetrahydronaphthyridinyl, tetrahydropyridoazepinyl and the like.

The optionally substituted bicyclic hydrocarbon group means that an arbitrary hydrogen atom on the bicyclic hydrocarbon group may be substituted with the same substituent group as on the above-mentioned bicyclic heterocyclic ring. Examples thereof include pentalenyl, indanyl, indenyl, naphthalenyl, tetrahydrobenzocycloheptenyl, tetrahydronaphthalenyl and the like.

Among the compounds of the present invention, particularly preferable compounds are described below in more detail.

In respect of stability, the compound is preferably a compound wherein $R^1$ and $R^2$ are preferably C1-6 alkyl groups, more preferably C1-3 alkyl groups, particularly methyl groups. $R^3$ is preferably a hydrogen atom, and for inhibitory action on DPP-IV, $R^4$ is preferably a cyano group. Further, A is preferably an optionally substituted 6-5, 6-6 or 6-7-system bicyclic heterocyclic group containing at least one heteroatom out of nitrogen, oxygen and sulfur atoms, particularly preferably an optionally substituted 6-5-system bicyclic heterocyclic group containing 1 to 3 nitrogen atoms. In addition, D is preferably —CONH— or —CO—, E is preferably —CH$_2$CH$_2$—, and n is preferably 1 or 2.

In the preferable compounds of the general formula (I), particularly preferable bicyclic heterocyclic groups represented by A are described in more detail below.

One group is the case where D in the general formula (I) is —CO—, and A is a 6-5-system bicyclic alicyclic heterocyclic group represented by the following formula:

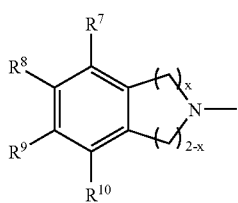

(II)

wherein x is an integer of 0 to 2, $R^7$, $R^8$, $R^9$ and $R^{10}$ are the same or different and each represents a hydrogen atom, a halogen atom, a hydroxy group, a trifluoromethyl group, an optionally substituted C1-6 alkyl group or an optionally substituted C1-6 alkoxy group. Particularly, the compound wherein x is 1, that is, dihydroisoindole is preferable in respect of activity, absorptivity, safety, and compound stability.

Another group is the case where D in the general formula (I) is —CONH—, and A is a 6-5-system bicyclic heterocyclic group represented by the following formula:

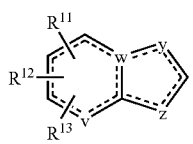

(III)

wherein ----- represents a single or double bond, at least one of y, z, v and w is an oxygen, nitrogen or sulfur atom, $R^{11}$, $R^{12}$ and $R^{13}$ may be substituted on any hydrogen atoms on the ring, are the same or different and each represents a hydrogen atom, a hydroxy group, a trifluoromethyl group, a trifluoroacetyl group, an oxo group, an optionally substituted C1-6 alkyl group, an optionally substituted C1-6 alkoxy group, or an optionally substituted C6-10 aryl group. Particularly preferable is the compound wherein 1 to 3 groups out of y, z, v and w are nitrogen atoms, and the remainder is a carbon atom. Further, the compound wherein y is a nitrogen atom while the remainder are carbon atoms, or v, w and y are nitrogen atoms while z is a carbon atom, that is, indole or pyrazolopyrimidine is generally considered to be more preferable in respect of activity, selectivity for the enzyme, ADME profile (absorptivity, metabolic stability, effect durability and the like), safety (mutagenicity, metabolic enzyme induction, metabolic enzyme inhibition, safety for each organ, and the like), compound stability, and the like.

The process for producing the compound of the present invention is described by reference to the following reaction schemes (1 to 3).

(Reaction scheme 1)

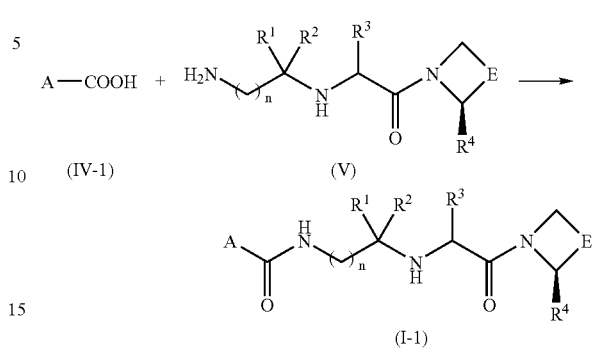

wherein the compound represented by the general formula (IV-1) is the compound wherein one hydrogen atom on the ring A was substituted with COOH, and the other symbols have the same meaning as defined above.

The reaction scheme 1 is a step of obtaining a compound represented by the general formula (I-1) by reacting a compound represented by the general formula (IV-1) with a compound represented by the general formula (V) or a salt thereof. Examples of the salt of the compound represented by the general formula (V) include hydrochloride, trifluoroacetate and the like.

The reaction of the compound represented by the general formula (IV-1) with the compound represented by the general formula (V) or a salt thereof proceeds preferably under the temperature conditions of −10 to 80° C., particularly, 0° C. to room temperature for 0.5 hour to 3 days by using a condensation reagent (for example, dicyclohexylcarbodiimide, N-(3-dimethylaminopropyl)-N'-ethylcarbodiimide or its hydrochloride, N,N'-carbonyldiimidazole or the like) activating the carboxylic acid of the compound represented by the general formula (IV-1) alone or in combination with an additive (N-hydroxysuccinimide, hydroxybenzotriazole or the like) in the presence or absence of a base (for example, triethylamine, 4-dimethylaminopyridine or the like) in a suitable solvent (for example, tetrahydrofuran, dichloromethane, N,N-dimethylformamide or the like).

(Reaction scheme 2)

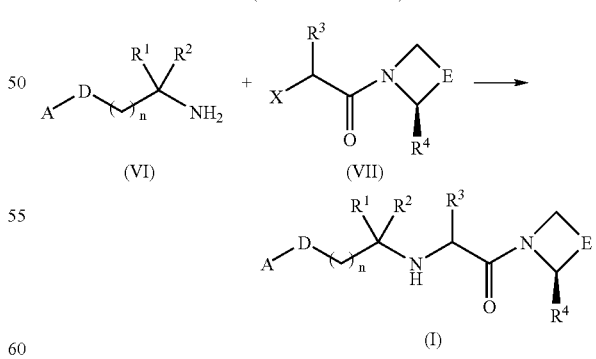

wherein X represents a halogen atom, and the other symbols have the same meaning as defined above.

The reaction scheme 2 is a step of obtaining a compound represented by the general formula (I) by reacting a compound represented by the general formula (VI) or a salt thereof with a compound represented by the general formula (VII). Examples of the salt of the compound represented by the general formula (VI) include hydrochloride, trifluoroacetate and the like.

The reaction of the compound represented by the general formula (VI) or a salt thereof with the compound represented by the general formula (VII) proceeds preferably under the temperature conditions of −10 to 80° C., particularly, 0° C. to room temperature for 0.5 hour to 3 days in the presence or absence of a base (for example, triethylamine, 4-dimethylaminopyridine, potassium carbonate or the like) and an additive (for example, sodium bromide, sodium iodide, potassium iodide) in a suitable solvent (for example, tetrahydrofuran, dichloromethane, N,N-dimethylformamide, acetone or the like).

(Reaction scheme 3)

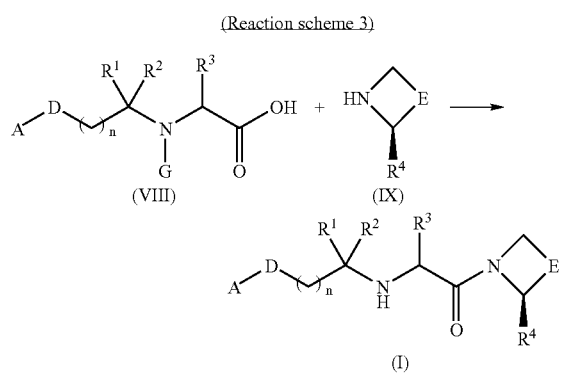

wherein G is a protecting group for amino acid (for example, t-butoxycarbonyl (Boc)), and the other symbols have the same meaning as defined above.

The reaction scheme 3 is a step of obtaining a compound represented by the general formula (I) by deprotecting a compound obtained by reacting a compound represented by the general formula (VIII) with a compound represented by the general formula (IX) or a salt thereof. Examples of the salt of the compound represented by the general formula (IX) include hydrochloride, trifluoroacetate and the like.

The amidation reaction proceeds preferably under the temperature conditions of −10 to 80° C., particularly, 0° C. to room temperature for 0.5 hour to 3 days by using a condensation reagent (for example, dicyclohexylcarbodiimide, N-(3-dimethylaminopropyl)-N'-ethylcarbodiimide or its hydrochloride, N,N'-carbonyldiimidazole or the like) activating the carboxylic acid of the compound represented by the general formula (VIII) alone or in combination with an additive (N-hydroxysuccinimide, hydroxybenzotriazole or the like) in the presence or absence of a base (for example, triethylamine, 4-dimethylaminopyridine or the like) in a suitable solvent (for example, tetrahydrofuran, dichloromethane, N,N-dimethylformamide or the like).

When the protecting group is for example a Boc group, the deprotection reaction proceeds preferably under the temperature conditions of −10 to 50° C., particularly, 0° C. to room temperature for 10 minutes to 24 hours by using an acid such as hydrogen chloride or trifluoroacetic acid in a suitable solvent (for example, 1,4-dioxane, tetrahydrofuran or the like).

Now, the process for producing the starting materials are described by reference to the following reaction schemes (4 to 7).

(Reaction scheme 4)

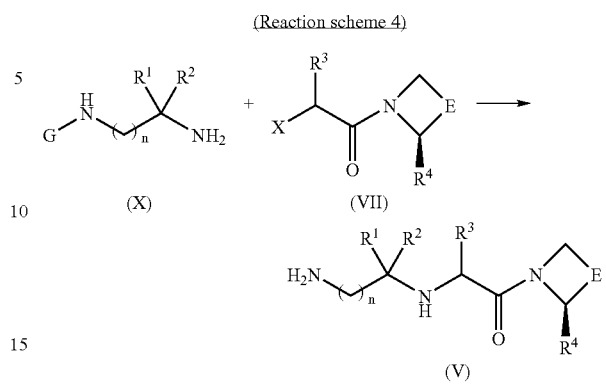

wherein each symbol has the same meaning as defined above.

The reaction scheme 4 is a step of obtaining the compound (V) by reacting a compound represented by the general formula (X) with a compound represented by the general formula (VII) and then deprotecting the product.

The reaction of the compound represented by the general formula (X) with the compound represented by the general formula (VII) proceeds preferably under the temperature conditions of −10 to 80° C., particularly, 0° C. to room temperature for 0.5 hour to 3 days in the presence or absence of a base (for example, triethylamine, 4-dimethylaminopyridine, potassiumcarbonate or the like) and an additive (for example, sodium bromide, sodium iodide, or potassium iodide) in a suitable solvent (for example, tetrahydrofuran, dichloromethane, N,N-dimethylformamide, acetone or the like).

When the protecting group is for example a Boc group, the deprotection reaction proceeds preferably under the temperature conditions of −10 to 50° C., particularly, 0° C. to room temperature for 10 minutes to 24 hours by using an acid such as hydrogen chloride or trifluoroacetic acid in a suitable solvent (for example, 1,4-dioxane, tetrahydrofuran or the like).

(Reaction scheme 5)

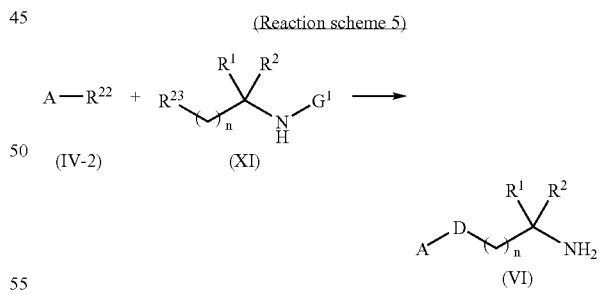

wherein $G^1$ represents a protecting group for amino acid (for example, t-butoxycarbonyl (Boc)) or a hydrogen atom; $R^{22}$ represents —COOH, —NH$_2$, or —NH— in the ring when A represents the general formula (II); $R^{23}$ represents —COOH or —NH$_2$; one of $R^{22}$ and $R^{23}$ represents a carboxylic acid, and the other represents an amine; and the other symbols have the same meaning as defined above.

The reaction scheme 5 is a step of obtaining a compound represented by the general formula (VI) by reacting a compound represented by the general formula (IV-2) or a salt thereof (in the case of amine) with a compound represented by the general formula (XI) or a salt thereof (in the case of amine) (followed by deprotection reaction when $G^1$ is a protecting group for amino acid). Examples of the salt of the compound represented by the general formula (IV-2) or (XI) include hydrochloride, trifluoroacetate and the like.

The amidation reaction proceeds preferably under the temperature conditions of −10 to 80° C., particularly, 0° C. to room temperature for 0.5 hour to 3 days, by using a condensation reagent (for example, dicyclohexylcarbodiimide, N-(3-dimethylaminopropyl)-N'-ethylcarbodiimide or its hydrochloride, N,N'-carbonyldiimidazole or the like) activating the carboxylic acid alone or in combination with an additive (N-hydroxysuccinimide, hydroxybenzotriazole or the like) in the presence or absence of a base (for example, triethylamine, 4-dimethylaminopyridine or the like) in a suitable solvent (for example, tetrahydrofuran, dichloromethane, N,N-dimethylformamide or the like).

When the compound represented by the general formula (IV-2) is a carboxylic acid ($R^{22}$ is —COOH), the carboxylic acid can also be reacted as follows. That is, the carboxylic acid is converted into the corresponding acid chloride ($R^{22}$ is converted into —COCl) by using oxalyl chloride, thionyl chloride or the like in a suitable solvent (for example, tetrahydrofuran, dichloromethane, N,N-dimethylformamide or the like), and the reaction with the compound represented by the general formula (XI) ($R^{23}$ is —NH$_2$) or a salt thereof proceeds preferably under the temperature conditions of −10 to 80° C., particularly, 0° C. to room temperature for 0.5 hour to 3 days in the presence or absence of a base (for example, triethylamine, 4-dimethylaminopyridine or the like).

When $G_1$ is, for example, a Boc group, the deprotection reaction proceeds preferably under the temperature conditions of −10 to 50° C., particularly, 0° C. to room temperature for 10 minutes to 24 hours by using an acid such as hydrogen chloride or trifluoroacetic acid in a suitable solvent (for example, 1,4-dioxane, tetrahydrofuran or the like).

(Reaction scheme 6)

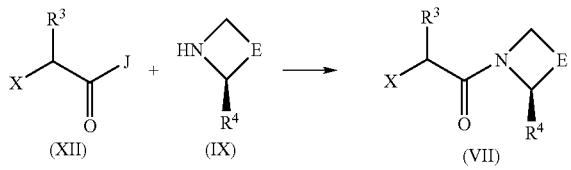

wherein J represents —OH or a halogen atom, and the other symbols have the same meaning as defined above.

The reaction scheme 6 is a step of obtaining a compound represented by the general formula (VII) by reacting a compound represented by the general formula (XII) with a compound represented by the general formula (IX) and a salt thereof.

The compound represented by the general formula (XII) (after conversion into the corresponding acid chloride by use of oxalyl chloride, thionyl chloride or the like when J is —OH) is reacted with the compound represented by the general formula (IX) or a salt thereof under the temperature conditions of −10 to 80° C., particularly, 0° C. to room temperature for 0.5 hour to 3 days in the presence or absence of a base (for example, triethylamine, 4-dimethylaminopyridine or the like) in a suitable solvent (for example, tetrahydrofuran, dichloromethane, N,N-dimethylformamide or the like), whereby the compound represented by the general formula (VII) is obtained.

(Reaction scheme 7)

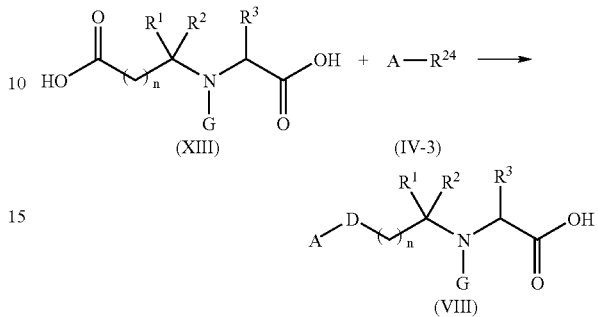

wherein $R^{24}$ represents —NH$_2$, or when A represents the general formula (II), $R^{24}$ represents —NH— in the ring, and the other symbols have the same meaning as defined above.

The reaction scheme 7 is a step of obtaining a compound represented by the general formula (VIII) by reacting a compound represented by the general formula (XIII) with a compound represented by the general formula (IV-3) and a salt thereof.

The reaction proceeds preferably under the temperature conditions of −10 to 80° C., particularly, 0° C. to room temperature for 0.5 hour to 3 days, by using a condensation reagent (for example, dicyclohexylcarbodiimide, N-(3-dimethylaminopropyl)-N'-ethylcarbodiimide or its hydrochloride, N,N'-carbonyldiimidazole or the like) activating the carboxylic acid alone or in combination with an additive (N-hydroxysuccinimide, hydroxybenzotriazole or the like) in the presence or absence of a base (for example, triethylamine, 4-dimethylaminopyridine or the like) in a suitable solvent (for example, tetrahydrofuran, dichloromethane, N,N-dimethylformamide or the like).

The objective compound obtained in each of the steps described above can be easily isolated by usual separation and purification method. As the isolation method, various kinds of generally used method can be used, and such method can be exemplified by recrystallization, reprecipitation, solvent extraction, column chromatography and the like.

The compound of the present invention can exhibit polymorphism, and can occur multiple tautomers. Accordingly, the present invention encompasses any stereoisomers, optical isomers, polymorphs, tautomers, and arbitrary mixtures thereof.

The compound of the present invention includes pharmaceutically acceptable salts thereof. Examples of the pharmaceutically acceptable salts include inorganic acid addition salts (for example, salts with hydrochloric acid, hydrobromic acid, hydriodic acid, sulfuric acid, nitric acid, phosphoric acid and the like), organic acid addition salts (for example, salts with methane sulfonic acid, benzene sulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid, pantothenic acid, methylsulfuric acid and the like), salts with an amino acid (for example, salts such as glutamic acid, aspartic acid and the like) and the like. The reaction of forming the acid addition salt can be carried out according to a conventional method.

The compound of the present invention can be provided as DPP-IV inhibitor. That is, the compound of the present invention exhibits a potent inhibitory action on DPP-IV, and is useful for prevention and treatment of diseases curable by an inhibitory action on DPP-IV, for example, diabetes (particularly type 2 diabetes), its related complications, obesity, autoimmune diseases (for example, arthritis, rheumatoid arthritis), osteoporosis, acquired immune deficiency syndrome (AIDS), rejection of transplanted organs and tissues, and the like.

Depending on the object, the method of administering the compound of the present invention can be selected from various administration forms described in general rules for pharmaceutical preparations in the Japanese Pharmacopoeia. In particular, the compound of the present invention is formed preferably into a pharmaceutical preparation for oral administration. For forming the compound in the form of tablets for oral administration, orally ingestible ingredients used in the field may be usually selected. Examples of such ingredients include excipients such as lactose, crystalline cellulose, white sugar and potassium phosphate. If necessary, various additives usually used in the filed of pharmaceutical manufacturing, such as a binder, a disintegrating agent, a lubricant and an aggregation inhibitor may be blended.

The amount of the compound of the present invention to be contained in the preparation of the present invention, that is, in the pharmaceutical composition of the present invention is not particularly limited and can be suitably selected from a broad range. The amount of the compound of the present invention as an active ingredient is selected suitably depending on the way of using it, the age, sex and other conditions of the patient, and the severeness of the disease, but usually the amount of the compound of the present invention is considered to be about 0.01 to 500 mg per kg of body weight. The preparation of the present invention can be administered all at once or in 2 to 4 divided portions per day.

Hereinafter, the present invention is described in more detail by reference to the Examples and Intermediate Examples, but these examples are not intended to limit the present invention.

INTERMEDIATE EXAMPLE 1

(S)-1-(2-Chloroacetyl)pyrrolidine-2-carbonitrile

In a similar procedure as employed in a patent (WO98/19998), L-proline amide (10.0 g) was reacted with chloroacetyl chloride (7.0 ml) and then subjected to dehydration reaction to give the title compound (7.7 g, yield (Y.:51%).

$^1$H NMR; (DMSO-$d_6$) δ (ppm):2.0-2.2 (4H, m), 3.4-3.5 (1H, m), 3.6-3.7 (1H, m), 4.4-4.5 (2H, m), 4.78 (1H, q).

ESI/MS (m/z):173 (M+H)$^+$, 171 (M−H)$^−$.

INTERMEDIATE EXAMPLE 2

(R)-1-(2-Chloroacetyl)pyrrolidine-2-carbonitrile

In a similar procedure as employed in the Intermediate Example 1, D-proline amide (3.2 g) was reacted with chloroacetyl chloride (2.5 ml) and then subjected to dehydration reaction to give the title compound (3.2 g, Y.:66%).

$^1$H NMR; (DMSO-$d_6$) δ (ppm):2.1-2.4 (4H, m), 3.5-3.8 (2H, m), 4.0-4.2 (2H, m), 4.7-4.9 (1H, m).

ESI/MS (m/z):173 (M+H)$^+$.

INTERMEDIATED EXAMPLE 3

(S)-3-(2-Chloroacetyl)thiazolidine-4carbonitrile 3-t-Butyl thiazolidine-3,4-dicarboxylate (2.0 g) was dissolved in tetrahydrofuran (10 ml), and N,N'-carbonyl diimidazole (1.4 g) was added thereto with ice-cooling. The mixture was warmed to room temperature and stirred for 6 hours. 1,4-Dioxane (10 ml) was added thereto, and the mixture was added dropwise to 28% ammonia water (40 ml) cooled on an ice bath. The mixture was warmed to room temperature and stirred for 20 hours. The reaction solution was extracted with ethyl acetate (60 ml). The organic phase was washed with a saturated saline solution and dried over sodium sulfate anhydrous. The product was concentrated under reduced pressure to give t-butyl 4-carbamoylthiazolidine-3-carboxylate (1.6 g, Y.:81%).

4 N HCl/1,4-dioxane (3.5 ml) was added to the t-butyl 4-carbamoyl thiazolidine-3-carboxylate (1.62 g) obtained above, and the mixture was stirred overnight. The reaction mixture was neutralized (pH 7.5 to 8) by adding water and 10% sodium bicarbonate solution and concentrated under reduced pressure. N,N-Dimethylformamide was added thereto, then the mixture was sonicated, and insolubles were removed by filtration. The filtrate was concentrated under reduced pressure to give thiazolidine-4-carboxylic acid amide (735 mg, Y.:80%).

In a similar procedure as employed in the Intermediate Example 1, the thiazolidine-4-carboxylic acid amide (102 mg) obtained above was reacted with chloroacetyl chloride (105 mg) and then subjected to dehydration reaction to give the title compound (87 mg, Y.:59%).

ESI/MS (m/z):191 (M+H)$^+$.

INTERMEDIATE EXAMPLE 4

(S)-1-(2-Chloroacetyl)azetidine-2-carbonitrile

4 N HCl/1,4-dioxane (2.5 ml) was added to a solution of t-butyl 2-carbamoylazetidine-1-carboxylate (500 mg) in 1,4-dioxane (2.0 ml) under cooling on an ice bath. The mixture was stirred for 2 hours at room temperature. The reaction mixture was neutralized by adding 5 N sodium hydroxide dropwise. The reaction mixture was concentrated under reduced pressure, then N,N-dimethylformamide was added thereto, insolubles were removed by filtration, and the filtrate was concentrated under reduced pressure to give azetidine-2-carboxylic acid amide (161 mg, Y.:65%).

In a similar procedure as employed in the Intermediate Example 1, the azetidine-2-carboxylic acid amide (161 mg) obtained above was reacted with chloroacetyl chloride (200 mg) and then subjected to dehydration reaction to give the title compound (112 mg, Y.:44%).

ESI/MS (m/z):159 (M+H)$^+$.

INTERMEDIATE EXAMPLE 5

(S)-1-(2-Bromo-2-phenylacetyl)pyrrolidine-2-carbonitrile

2-Bromo-2-phenylacetic acid (500 mg) was dissolved in dichloromethane (30 ml), and oxalyl chloride (950 μl) and N,N-dimethylformamide (2 drops) were added thereto and stirred at room temperature for 1 hour. The reaction solution was concentrated under reduced pressure, then diluted with dichloromethane (20 ml), added dropwise to a solution of (S)-pyrrolidine-2-carbonitrile (310 mg) in triethylamine (650 μl) and dichloromethane (30 ml), and stirred at room temperature for 3 hours. 10% Citric acid solution was added thereto, and the organic phase was separated, then washed with 4% sodium bicarbonate solution and a saturated saline solution, and dried over sodium sulfate anhydrous. The product was concentrated under reduced pressure to give the title compound (700 mg, Y.: quant.).

ESI/MS (m/z):294 (M+H)$^+$, 292 (M−H)$^−$.

In a similar procedure as employed in the Intermediate Examples 1 to 5, compounds were synthesized according to the following reaction scheme. The synthesized compounds and data are shown in Table 1. (Each symbol has the same meaning as defined above.)

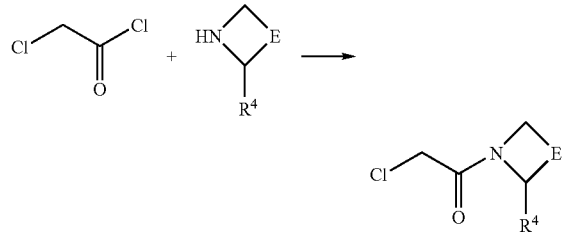

TABLE 1

| Intermediate Example | Compound Name | ESI/MS(m/z) |
| --- | --- | --- |
| 6 | 3-(2-chloroacetyl)thiazolidine | 166 (M + H)$^+$ |
|  |  | 164 (M − H)$^−$ |
| 7 | 1-(2-chloroacetyl)pyrrolidine | 148 (M + H)$^+$ |
|  |  | 146 (M − H)$^−$ |
| 8 | 1-(2-chloroacetyl)piperazine-2-carbonitrile | 187 (M + H)$^+$ |
|  |  | 185 (M − H)$^−$ |
| 9 | 1-(2-chloroacetyl)morpholine | 164 (M + H)$^+$ |
|  |  | 162 (M − H)$^−$ |

INTERMEDIATE EXAMPLE 10

(S)-Pyrrolidine-2-carbonitrile

L-Proline amide (23 g) was dissolved in tetrahydrofuran (1200 ml), then triethylamine (22 g) was added thereto, and the mixture was cooled on an ice bath. 2-Nitrophenylsulfonyl chloride (42 g) was added thereto and stirred for 1 hour at room temperature. Ethyl acetate and water were added thereto, and the organic phase was separated and dried over sodium sulfate anhydrous. The product was concentrated under reduced pressure, then ether was added to the residue, and precipitated crystals were collected by filtration and dried under reduced pressure. The resulting crystals (45 g) were dissolved in pyridine (890 ml), and imidazole (23 g) was added thereto and cooled on an ice bath. Phosphoryl chloride (31 ml) was added dropwise thereto and stirred at room temperature for 2 hours. Ice (1000 g) and ether (2000 ml) were added thereto, and the organic phase was separated, washed with water and dried over sodium sulfate anhydrous. The product was concentrated under reduced pressure, the resulting residue was dissolved in ether (4.1L), and filtered. 4 N HCl/1,4-dioxane (130 ml) was added dropwise to the filtrate with ice cooling and stirred for 3 hours at room temperature. Precipitated crystals were collected by filtration and washed with ether. The crystals were dried under reduced pressure to give a hydrochloride (20 g, Y.:88%) of the title compound as pale yellow crystals.

$^1$HNMR; (CDCl$_3$) δ (ppm):2.2-2.3 (2H, m), 2.3-2.4 (1H, m), 2.5-2.6 (1H, m), 3.5-3.7 (2H, m), 5.0 (1H, t).

INTERMEDIATE EXAMPLE 11

Piperidine-2-carbonitrile

In a similar procedure as employed in the Intermediate Examples 3 and 10, a hydrochloride (4.4 g, Y.:69%) of the title compound was obtained from piperidine-2-carboxylic acid (15 g).

ESI/MS (m/z):111 (M+H)$^+$.

INTERMEDIATE EXAMPLE 12

(S)-1-[(2-Amino-1,1-dimethylethyl)aminoacetyl]pyrrolidine-2-carbonitrile dihydrochloride 2-Methylpropane-1,2-diamine (5.0 g) was dissolved in dichloromethane (200 ml) and stirred for 15 minutes at 0° C. A solution of BOC-ON (15 g) in dichloromethane (60 ml) was added dropwise thereto and then stirred for 2 hours at room temperature. The reaction mixture was diluted with chloroform with ice cooling and then acidified by 10% citric acid solution, and the organic phase was separated. The aqueous phase was alkalinized by 5 N sodium hydroxide solution, then extracted with ethyl acetate, and the extract was dried over sodium sulfate anhydrous. The product was concentrated under reduced pressure to give t-butyl (2-amino-2-methyl-1-propyl)carbamate (7.9 g, Y.:74%).

$^1$H NMR; (DMSO-d$_6$) δ (ppm):0.9 (6H, s), 1.4 (9H, s), 2.8 (2H, d), 6.7 (1H, brt).

The t-butyl (2-amino-2-methyl-1-propyl)carbamate (7.9 g) obtained above, sodium iodide (8.7 g), and potassium carbonate (8.0 g) were suspended in acetone (230 ml). A solution of (S)-1-(2-Chloroacetyl)pyrrolidine-2-carbonitrile (10 g) in acetone (80 ml) was added thereto with ice cooling, and stirred as such for 30 minutes. The reaction mixture was stirred for 15 hours at room temperature and then concentrated under reduced pressure. The residue was dissolved in chloroform, then insolubles were removed by filtration, and the filtrate was concentrated under reduced pressure. The resulting residue was purified by colunm chromatography (eluting solvent; dichloromethane:methanol 80:1→60:1→40: 1) to give t-butyl (S)-{2-[(2-cyanopyrrolidine-1-yl)-2-oxoethylamino]-2-methyl-1-propyl} carbamate (12 g, Y.:91%).

$^1$H NMR; (DMSO-d$_6$) δ (ppm):0.9 (6H, s), 1.4 (9H, s), 1.9-2.2 (4H, m), 2.9 (2H, d), 3.2-3.5 (4H, m), 3.5-3.7 (1H, m), 4.7-4.8 (1H, m), 6.6-6.7 (1H, brt).

ESI/MS (m/z):325 (M+H)$^+$, 323 (M−H)$^−$.

The t-butyl (S)-{2-[(2-cyanopyrrolidine-1-yl)-2-oxoethylamino]-2-methyl-1-propyl}carbamate (4.8 g) obtained above was dissolved in dichloromethane (50 ml). 4 N HCl/1,4-dioxane (50 ml) was added thereto under cooling on ice and stirred for 1 hour at room temperature. The product was concentrated under reduced pressure to give the title compound (4.2 g, Y.:96%).

$^1$H NMR; (DMSO-d$_6$) δ (ppm):1.4 (6H, s), 2.0-2.3 (4H, m), 3.2 (2H, brs), 3.5-3.6 (2H, m), 3.7-3.8 (1H, m), 4.0-4.2 (2H, m), 4.9 (1H, q), 8.5 (2H, brs), 9.4 (1H, brs), 9.5 (1H, brs)

ESI/MS (m/z):225 (M+H)$^+$.

INTERMEDIATE EXAMPLE 13

(S)-1-[2-(1,1-Dimethyl-2-methylaminoethylamino)acetyl]-pyrrolidine-2-carbonitrile (S)-1-[(2-Amino-1,1-dimethylethyl)aminoacetyl]-pyrrolidine-2-carbonitrile dihydrochloride (1.48 g) was dissolved in acetonitrile (50 ml), and 4-nitrophenyl formate (1.00 g) and potassium carbonate (1.37 g) were added thereto and stirred for 16 hours at room temperature. The reaction mixture was concentrated under reduced pressure, and the residue was purified by column chromatography (eluting solvent; dichloromethane:methanol 5:1) to give (S)-N-{2-[2-(2-cyanopyrrolidin-1-yl)-2-oxoethylamino]-2-methyl-1-propyl}-formamide (693 mg, Y.:55%).

ESI/MS (m/z):253 (M+H)$^+$.

The (S)-N-{2-[2-(2-cyanopyrrolidin-1-yl)-2-oxoethylamino]-2-methyl-1-propyl}formamide (690 mg) obtained above was dissolved in MeOH (30 ml). Sodium cyanoborohydride (172 mg) was added there to and stirred for 6 hours at room temperature. The reaction mixture was concentrated under reduced pressure, and the residue was purified by column chromatography (eluting solvent; dichloromethane:methanol 5:1→3:1) to give the title compound (455 mg, Y.:70%).

$^1$H NMR; (DMSO-$d_6$) δ (ppm):1.4 (6H, s), 2.0 (2H, brs), 2.0-2.3 (4H, m), 2.50 (3H, s), 3.2 (2H, brs), 3.5-3.6 (2H, m), 4.0-4.2 (2H, m), 4.9 (1H, q).

ESI/MS (m/z):225 (M+H)$^+$.

INTERMEDIATE EXAMPLE 14

3-Amino-3-methylbutanoic acid

3-Methylcrotonic acid (12.0 g) was dissolved in pyridine (40 ml), and benzyl amine (12.8 g) was added thereto, and the mixture was stirred for 3 hours at 120° C. The reaction mixture was cooled to room temperature, and after acetone was added to the resulting suspension, crystals were collected by filtration and washed. The crystals were dried under reduced pressure to give 3-benzylamino-3-methylbutanoic acid (10.3 g, Y.:42%) as colorless crystals.

ESI/MS:208 (M+H)$^+$, 206 (M−H)$^-$.

6 N Hydrochloric acid (5.8 ml) was added to a solution of the thus obtained 3-benzylamino-3-methylbutanoic acid (6.0 g) in ethanol (90 ml). 5% Palladium on carbon (2.4 g) andacetic acid (46 ml) were added thereto and stirred for 5 hours at 50° C. in a hydrogen atmosphere. Insoluble matter was removed by filtration, and the filtrate was concentrated under reduced pressure. Precipitated crystals were washed with ether and dried under reduced pressure to give the title compound (4.4 g, Y.:quant.) as colorless crystals.

$^1$H NMR; (DMSO-$d_6$) δ (ppm):1.4 (6H, s), 2.7 (2H, s), 8.3 (3H, brs).

ESI/MS (m/z):118 (M+H)$^+$, 116 (M−H)$^-$.

INTERMEDIATE EXAMPLE 15

4-Methyl-1,4-pentanediamine

Methyl 4-methyl-4-nitropentanoate (5.00 g) was dissolved in ethanol (25 ml), and 1 N sodium hydroxide solution was added thereto and stirred for 1 day. The mixture was concentrated under reduced pressure, then chloroform and water were added thereto, and the aqueous phase was washed with chloroform. 2 N Hydrochloric acid (20 ml) was added to the aqueous phase which was then extracted with chloroform, and the extract was dried over sodium sulfate anhydrous. The product was concentrated under reduced pressure to give 4-methyl-4-nitropentanoic acid (4.32 g, Y.:94%) as white crystals.

$^1$H NMR; (CDCl$_3$) δ (ppm):1.6 (6H, s), 2.2-2.3 (2H, m), 2.4-2.5 (2H, m), 10.8 (1H, brs).

The 4-methyl-4-nitropentanoic acid (4.3 g) obtained above was dissolved in dichloromethane, and N-(3-dimethylaminopropyl)-N'-ethylcarbodiimide hydrochloride (6.1 g) and triethylamine (4.5 ml) were added thereto and stirred for 1 hour. Benzylamine (3.4 g) was added thereto and stirred for 1 day. Water was added to the reaction mixture which was then acidified by 2 N hydrochloric acid and extracted with chloroform. The organic phase was washed with a saturated sodium bicarbonate solution and a saturated saline solution and dried over sodium sulfate anhydrous. The resulting product was concentrated under reduced pressure, and the residue was purified by column chromatography (eluting solvent; ethyl acetate:n-hexane 1:1.5) to give N-benzyl-4-methyl-4-nitropentanoic acid amide (2.5 g, Y.:38%) as a colorless oil.

$^1$H NMR; (CDCl$_3$) δ (ppm):1.6 (6H, s), 2.1-2.2 (2H, m), 2.2-3.3 (2H, m), 4.4 (2H, d), 6.0 (1H, brs), 7.3-7.4 (5H, m).

The N-benzyl-4-methyl-4-nitropentanoic acid amide (2.5 g) obtained above was dissolved in tetrahydrofuran (20 ml) and cooled to 0° C. 1 N Borane tetrahydrofuran complex (13 ml) was added dropwise thereto and then stirred overnight at room temperature. The reaction mixture was cooled again to 0° C., and 2 N hydrochloric acid (30 ml) was added thereto, followed by heating to 50° C. The reaction solution was extracted with ethyl acetate. The aqueous phase was alkalinized by 50% sodium hydroxide solution, extracted with chloroform. The extract was washed with a saturated saline solution, and dried over sodium sulfate anhydrous. The product was concentrated under reduced pressure to give benzyl-4-methyl-4-nitropentylamine (1.7 g, Y.: 73%) as a colorless oil.

$^1$H NMR; (CDCl$_3$) δ (ppm):1.4-1.5 (2H, m), 1.6 (6H, s), 2.0 (2H, dt), 2.6 (2H, t), 7.2-7.4 (5H, m).

The benzyl-4-methyl-4-nitropentylamine (1.7 g) obtained above and 10% palladium on carbon (500 mg) were suspended in ethanol and stirred for 1 day at 60° C. in a hydrogen atmosphere. The reaction mixture was cooled to room temperature, filtered with celite and concentrated under reduced pressure. The resulting product was acidified by 2 N hydrochloric acid and extracted with ether. The aqueous phase was alkalinized by 50% sodium hydroxide solution, extracted with ether and dried over sodium sulfate anhydrous. The product was concentrated under reduced pressure to give the title compound (420 mg, Y.:50%).

$^1$H NMR; (CDCl$_3$) δ (ppm):1.2 (6H, s), 1.5-1.6 (4H, m), 2.7-2.8 (2H, m).

INTERMEDIATE EXAMPLE 16

2-Methylpyrazolo[1,5-a]pyrimidine-6-carboxylic acid

2-Methylpyrazolo[1,5-a]pyrimidine-6-carboxylic acid amide (475 mg) was dissolved in ethanol (5 ml), and 5 N sodium hydroxide solution (2 ml) was added thereto and stirred for 1 hour at 70° C. The reaction mixture was cooled to room temperature, water was added thereto, and the reaction mixture was washed with ethyl acetate. 2 N Hydrochloric acid was added to the aqueous phase until it became acidic, and precipitated crystals were collected by filtration and washed with water and n-hexane. The crystals were dried under reduced pressure to give the title compound (300 mg, Y.:63%) as white crystals.

ESI/MS:178 (M+H)$^+$, 176 (M−H$^-$.

INTERMEDIATE EXAMPLE 17

2,5,7-Trimethylpyrazolo[1,5-a]pyrimidine-6-carboxylic acid

3-Amino-5-methylpyrazole (970 mg) and ethyl diacetoacetate (1.7 g) were dissolved in acetic acid (5 ml) and stirred at 120° C. for 3 hours. The reaction mixture was cooled to room temperature and concentrated under reduced pressure. Ethanol (5 ml) and 5 N sodium hydroxide solution (2 ml) were added to the residue and stirred at 70° C. for 1 hour. The reaction mixture was cooled to room temperature, and water was added to the reaction mixture which was then washed with ethyl acetate. 2 N Hydrochloric acid was added to the aqueous phase until it became acidic, and precipitated crystals were collected by filtration and washed with water and n-hexane. The crystals were dried under reduced pressure to give the title compound (1.6 g, Y.:80%) as white crystals.

$^1$H NMR; (DMSO-d$_6$) δ (ppm):2.4 (3H, s), 2.5 (3H, s), 2.8 (3H, s), 6.5 (1H, s), 13.8 (1H, brs).
ESI/MS (m/z):206 (M−H)$^-$.

INTERMEDIATE EXAMPLE 18

7-Methoxy-2,5-dimethylpyrazolo[1,5-a]pyrimidine-6-carboxylic acid

3-Amino-5-methylpyrazole (970 mg) and diethyl acetomalonate (2.0 g) were dissolved in acetic acid (5 ml) and stirred for 3 hours at 120° C. The reaction mixture was cooled to room temperature and concentrated under reduced pressure, and ethanol was added to the residue which were then cooled to 0° C. Precipitated crystals were collected by filtration and washed with cold ethanol. The crystals were dried under reduced pressure to give ethyl 7-hydroxy-2,5-dimethylpyrazolo[1,5-a]pyrimidine-6-carboxylate (2.2 g, Y.:95%) as white crystals.

$^1$H NMR; (DMSO-d$_6$) δ (ppm):1.3 (3H, t), 2.3 (3H, s), 2.4 (3H, s), 4.2 (2H, q), 6.0 (1H, s), 12.6 (1H, brs).
ESI/MS (m/z):236 (M+H)$^+$, 234 (M−H)$^-$.

The ethyl 7-hydroxy-2,5-dimethylpyrazolo[1,5-a]pyrimidine-6-carboxylate (235 mg) obtained above was suspended in acetone (5 ml), and potassium carbonate (138 mg) was added thereto and stirred for 30 minutes at room temperature. Methyl iodide (1.0 ml) was added to the mixture which was then refluxed for 2 hours. The reaction mixture was cooled to room temperature, then water was added to the reaction mixture which was extracted with chloroform, and the organic phase was washed with a saturated saline solution and dried over sodium sulfate anhydrous. The resulting product was concentrated under reduced pressure, and the resulting crystals were dissolved in ethanol (5 ml). 5 N Sodium hydroxide solution (1 ml) was added thereto and stirred for 1 hour at 50° C. The reaction mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The crystals were dried under reduced pressure to give the title compound (162 mg, Y.:73%) as white crystals.

$^1$H NMR; (DMSO-d$_6$) δ (ppm):2.3 (3H, s), 2.7 (3H, s), 3.7 (3H, s), 6.4 (1H, s).
ESI/MS (m/z):222 (M+H)$^+$.

INTERMEDIATE EXAMPLE 19

5,7-Dimethyl-2-phenylpyrazolo[1,5-a]pyrimidine-6-carboxylic acid

3-Amino-5-phenylpyrazolo (1.6 g) and ethyl diacetoacetate (1.7 g) were dissolved in acetic acid (5.0 ml) and stirred for 3 hours at 120° C. The mixture was cooled to room temperature and concentrated under reduced pressure. Ethanol (10 ml) and 5 N sodium hydroxide solution (3 ml) were added to the residue and then stirred for 1 hour at 70° C. The mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The product was dried under reduced pressure to give the title compound (2.1 g, Y.:78%) as white crystals.

$^1$H NMR; (DMSO-d$_6$) δ (ppm):2.6 (3H, s), 2.9 (3H, s), 7.2 (1H, s), 7.4 (1H, t), 7.5 (2H, t), 8.1 (1H, d), 13.9 (1H, brs).
ESI/MS (m/z):266 (M−H)$^-$.

INTERMEDIATE EXAMPLE 20

2-Methyl-7-trifluoromethylpyrazolo[1,5-a]pyrimidine-6-carboxylic acid

3-Amino-5-methylpyrazole (389 mg) and ethyl (ethoxymethylidene)trifluoroacetoacetate (960 mg) were dissolved in ethanol (10 ml) and stirred for 1.5 hours at 70° C. Conc. hydrochloric acid (1 mg) was added thereto, and the mixture was stirred for additional 1 hour. The mixture was cooled to room temperature and concentrated under reduced pressure. Ethanol (10 ml) and 5 N sodium hydroxide solution (3 ml) were added to the residue and then stirred for 1 hour at 70° C. The mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The product was dried under reduced pressure to give the title compound (102 mg, Y.:42%) as white crystals.

$^1$H NMR; (DMSO-d$_6$) δ (ppm):2.6 (3H, s), 2.9 (3H, s), 7.2 (1H, s), 7.4 (1H, t), 7.5 (2H, t), 8.1 (1H, d), 13.9 (1H, brs).
ESI/MS (m/z):244 (M−H)$^-$.

INTERMEDIATE EXAMPLE 21

2-t-Butyl-5,7-dimethylpyrazolo[1,5-a]pyrimidine-6-carboxylic acid

3-Amino-5-t-butylpyrazole (1.6 g) and ethyl diacetoacetate (1.7 g) were dissolved in acetic acid (5 ml) and stirred for 3 hours at 120° C. The mixture was cooled to room temperature and concentrated under reduced pressure. Ethanol (10 ml) and 5 N sodium hydroxide solution (3 ml) were added to the residue and then stirred for 1 hour at 70° C. The mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The product was dried under reduced pressure to give the title compound (2.1 g, Y.:78%) as white crystals.

$^1$H NMR; (DMSO-d$_6$) δ (ppm):2.6 (3H, s), 2.9 (3H, s), 7.2 (1H, s), 7.4 (1H, t), 7.5 (2H, t), 8.1 (1H, d), 13.9 (1H, brs).
ESI/MS (m/z):246 (M−H)$^-$.

INTERMEDIATE EXAMPLE 22

2-t-Butyl-7-methylpyrazolo[1,5-a]pyrimidine-6-carboxylic acid

Ethyl acetoacetate (35.4 g) was dissolved in acetonitrile (200 ml), and dimethylformamide dimethyl acetal (30.9 g) was added thereto, and the mixture was stirred overnight at room temperature. The reaction mixture was concentrated under reduced pressure to give ethyl 2-dimethylaminomethyleneacetoacetate (50.4 g, Y.:99%) as a red oil.

$^1$H NMR; (CDCl$_3$-d$_6$) δ (ppm):1.3 (3H, t), 2.3 (3H, s), 3.1 (6H, brs), 4.2 (2H, q), 7.7 (1H, s).

The ethyl 2-dimethylaminomethyleneacetoacetate (556 mg) obtained above and 3-amino-5-t-butylpyrazole (418 mg) were dissolved in ethanol (10 ml) and stirred for 1.5 hours at 70° C. Conc. hydrochloric acid (1 ml) was added thereto, and the mixture was stirred for additional 1 hour. The mixture was cooled to room temperature and concentrated under reduced pressure. Ethanol (10 ml) and 5 N sodium hydroxide solution (3 ml) were added to the residue and then stirred for 1 hour at 70° C. The mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The product was dried under reduced pressure to give the title compound (396 mg, Y.:57%) as yellow crystals.

1H NMR; (DMSO-d$_6$) δ (ppm):1.4 (9H, s), 3.1 (3H, s), 6.8 (1H, s), 8.8 (1H, s), 13.5 (1H, brs).

ESI/MS (m/z):232 (M−H)$^-$.

INTERMEDIATE EXAMPLE 23

7-Methyl-2-phenylpyrazolo[1,5-a]pyrimidine-6-carboxylic acid

3-Amino-5-phenylpyrazolo (477 mg) and ethyl 2-N,N-dimethylaminomethyleneacetoacetate (556 mg) were dissolved in ethanol (10 ml) and stirred for 1.5 hours at 70° C. Conc. Hydrochloric acid (1 ml) was added thereto, and the mixture was stirred for additional 1 hour. The mixture was cooled to room temperature and concentrated under reduced pressure. Ethanol (10 ml) and 5 N sodium hydroxide solution (3 ml) were added to the residue and then stirred for 1 hour at 70° C. The mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The product was dried under reduced pressure to give the title compound (463 mg, Y.:61%) as yellow crystals.

$^1$H NMR; (DMSO-d$_6$) δ (ppm):3.2 (3H, s), 7.4 (1H, s), 7.5 (3H, m), 8.1 (2H, d), 8.9 (1H, s), 13.6 (1H, brs).

ESI/MS (m/z):252 (M−H)$^-$.

INTERMEDIATE EXAMPLE 24

7-Methoxy-5-methyl-2-phenylpyrazolo[1,5-a]pyrimidine-6-carboxylic acid

3-Amino-5-phenylpyrazole (1.56 mg) and diethyl acetomalonate (2.00 g) were dissolved in acetic acid (5.0 ml) and stirred for 3 hours at 120° C. The reaction mixture was cooled to room temperature and concentrated under reduced pressure. Ethanol was added to the residue which were then cooled to 0° C. Precipitated crystals were collected by filtration and washed with cold ethanol. The crystals were dried under reduced pressure to give ethyl 7-hydroxy-5-methyl-2-phenylpyrazolo[1,5-a]pyrimidine-6-carboxylate (2.73 g, Y.:92%) as white crystals.

$^1$H NMR; (DMSO-d$_6$) δ (ppm):1.3 (3H, t), 2.4 (3H, s), 4.3 (2H, q), 6.7 (1H, s), 7.4 (2H, t), 7.5 (2H, t), 8.0 (1H, d).

The ethyl 7-hydroxy-5-methyl-2-phenylpyrazolo[1.5-a]pyrimidine-6-carboxylate (297 mg) obtained above was suspended in acetone (5 ml), and potassium carbonate (138 mg) was added thereto and stirred for 30 minutes at room temperature. Methyl iodide (1.0 ml) was added to the mixture which was then refluxed for 2 hours. The reaction mixture was cooled to room temperature, and water was added to the reaction mixture which was extracted with chloroform, and the organic phase was washed with a saturated saline solution and dried over sodium sulfate anhydrous. The product was concentrated under reduced pressure, and the resulting crystals were dissolved in ethanol (5 ml). 5 N Sodium hydroxide solution (1 ml) was added thereto and stirred for 1 hour at 50° C. The reaction mixture was cooled to room temperature, and water was added to the mixture which was then washed with ethyl acetate. 2 N Hydrochloric acid was added to the aqueous phase until it became acidic, and precipitated crystals were collected by filtration and washed with water and n-hexane. The crystals were dried under reduced pressure to give the title compound (121 mg, Y.:45%) as white crystals.

$^1$H NMR; (DMSO-d$_6$) δ (ppm):2.7 (3H, s), 3.8 (3H, s), 7.2 (1H, s), 7.5 (1H, t), 7.5 (2H, dd), 8.0 (2H, d), 13.5 (1H, brs).

INTERMEDIATE EXAMPLE 25

5-Hydroxy-2-methylpyrazolo[1,5-a]pyrimidine-6-carboxylic acid

Triethylamine (2.02 g) and benzyloxycarbonyl chloride (1.71 g) were added dropwise to a solution of 3-amino-5-methylpyrazole (971 mg) in chloroform (20 ml) at 0° C., and the mixture was stirred for 18 hours. The mixture was concentrated under reduced pressure, and the residue was purified by column chromatography (eluting solvent; n-hexane:ethyl acetate 2:1) to give benzyl 5-methyl-2H-pyrazol-3-ylcarbamate (1.65 g, Y.:67%).

A mixed solution of the benzyl 5-methyl-2H-pyrazol-3-ylcarbamate (600 mg) obtained above and diethyl ethoxymethylenemalonate (1.80 g) was stirred for 18 hours at 100° C. The reaction mixture was concentrated under reduced pressure, and the residue was purified by column chromatography (eluting solvent; n-hexane:ethyl acetate 3:1) to give diethyl 2-(5-benzyloxycarbonylamino-3-methylpyrazol-1-ylmethylene)malonate (700 mg, Y.: 67%).

4 N Hydrochloric acid/1,4-dioxane (2 ml) was added to the diethyl 2-(5-benzyloxycarbonylamino-3-methylpyrazol-1-ylmethylene)m alonate (100 mg) obtained above and stirred for 22 hours. Precipitated crystals were collected by filtration and dried under reduced pressure to give ethyl 5-hydroxy-2-methylpyrazolo[1,5-a]pyrimidine-6-carboxylate (40 mg, Y.:73%).

In a similar procedure as employed in the Intermediate Example 24, the ethyl 5-hydroxy-2-methylpyrazolo[1,5-a]pyrimidine-6-carboxylate (154 mg) was hydrolyzed to give the title compound (136 mg, Y.: quant.).

$^1$H NMR; (DMSO-d$_6$) δ (ppm):2.3 (3H, s), 6.3 (1H, s), 8.6 (1H, s)

INTERMEDIATE EXAMPLE 26

7-Hydroxy-2-methylpyrazolo[1,5-a]pyrimidine-6-carboxylic acid

In a similar procedure as employed in the Intermediate Example 24, ethyl 7-methoxy-2-methylpyazolo[1,5-a]pyrimidine-6-carboxylate was hydrolyzed to give the title compound.

$^1$H NMR; (DMSO-d$_6$) δ (ppm):2.3 (3H, s), 6.3 (1H, s), 8.8 (1H, s).

INTERMEDIATE EXAMPLE 27

2-Hydroxymethylpyrazolo[1,5-a]pyrimidine-6-carboxylic acid

Acetonitrile (2.04 ml) was added to a solution of sodium methoxide (1.40 g) in tetrahydrofuran (50 ml) and refluxed for 1.5 hours. The mixture was cooled to room temperature, and methyl methoxyacetate (2.57 ml) was added to the mixture which was then refluxed overnight. The reaction mixture was cooled to room temperature, water was added to the reaction mixture which was adjusted to pH 7 by 1 N hydrochloric acid and extracted with ether. The organic phase was washed with a saturated saline solution and dried over sodium sulfate anhydrous. The resulting product was concentrated under reduced pressure, and the residue was purified by column chromatography (eluting solvent; n-hexane:ethyl acetate 2:1) to give 4-methoxy-3-oxobutyronitrile (1.14 g, Y.:39%).

Hydrazine monohydrate (0.49 ml) was added to a solution of the thus obtained 4-methoxy-3-oxobutyronitrile (1.14 g) in ethanol (50 ml), and refluxed for 17 hours. The reaction mixture was cooled to room temperature and concentrated under reduced pressure. The residue was purified by column chromatography (eluting solvent; dichloromethane:methanol 50:1) to give 5-methoxymethyl-2H-pyrazol-3-ylamine (684 mg, Y.:53%).

Ethyl 2-formyl-3-oxopropionate (775 mg) was added to a solution of the thus obtained 5-methoxymethyl-2H-pyrazol-3-ylamine (684 mg) in ethanol (50 ml), and stirred overnight. The reaction solution was concentrated under reduced pressure, and a saturated sodium bicarbonate solution was added to the residue which were then extracted with ethyl acetate. The organic phase was washed with a saturated saline solution and dried over sodium sulfate anhydrous. The resulting product was concentrated under reduced pressure, and the residue was purified by column chromatography (eluting solvent; n-hexane:ethyl acetate 4:1) to give ethyl 2-methoxymethylpyrazolo[1,5-a]pyrimidine-6-carboxylate (878 mg, Y.:69%). 1 M Boron tribromide solution in dichloromethane (0.51 ml) was added dropwise at −70° C. to a solution of the thus obtained ethyl 2-methoxymethylpyrazolo[1,5-a]pyrimidine-6-carboxylate (20 mg) in dichloromethane (2 ml). The temperature of the mixture under stirring was increased from −70° C. to −50° C. over 4.5 hours and then increased from −50° C. to room temperature over 2 hours. The reaction mixture was cooled to 0° C., water was added to the reaction mixture which was then extracted with ethyl acetate, and the extract was dried over sodium sulfate anhydrous. The resulting product was concentrated under reduced pressure to give ethyl 2-hydroxymethylpyrazolo[1,5-a]pyrimidine-6-carboxylate (19 mg, Y.:quant.).

5 N Sodium hydroxide solution (0.1 ml) was added to a solution of the thus obtained ethyl 2-hydroxymethylpyrazolo[1,5-a]pyrimidine-6-carboxylate (19 mg) in tetrahydrofuran (1 ml), and stirred for 17 hours at room temperature. After water was added, the reaction mixture was washed with ethyl acetate. The aqueous phase was acidified by 2 N hydrochloric acid, extracted with ethyl acetate and dried over sodium sulfate anhydrous. The resulting product was concentrated under reduced pressure, and the residue was dissolved in hot ethyl acetate and then filtered. The filtrate was concentrated under reduced pressure to give the title compound (11 mg, Y.:65%).

$^1$H NMR; (DMSO-$d_6$) δ (ppm):4.7 (2H, s), 6.8 (1H, s), 8.8 (1H, d), 9.3-9.4 (1H, m).

INTERMEDIATE EXAMPLE 28

2-Methoxymethylpyrazolo[1,5-a]pyrimidine-6-carboxylic acid

In a similar procedure as employed in the Intermediate Example 27, ethyl 2-methoxymethylpyrazolo[1,5-a]pyrimidine-6-carboxylate as the intermediate in Intermediate Example 27 was hydrolyzed to give the title compound.

$^1$H NMR; (DMSO-$d_6$) δ (ppm):3.4 (3H, s), 4.6 (2H, s), 6.8 (1H, s), 8.9 (1H, d), 9.4-9.5 (1H, m).

ESI/MS (m/z):206 (M−H)$^-$.

INTERMEDIATE EXAMPLE 29

1-Methyl-1H-indole-3-carboxylic acid

1H-Indole-3-carboxylic acid (960 mg) was dissolved in N,N-dimethylformamide (15 ml) and cooled to 0° C. Sodiumhydride (720 mg) was added in two divided portions thereto, and the mixture was warmed to room temperature and stirred for 1 hour. The mixture was cooled again to 0° C., and a solution of methyl iodide (0.67 ml) in N,N-dimethylformamide (5 ml) was added slowly dropwise thereto, and the mixture was warmed to room temperature and stirred for 2 hours. The reaction mixture was cooled to 0° C., then ice was added thereto, water (50 ml) was further added thereto, and precipitated crystals were collected by filtration and washed with water and n-hexane. The product was dried under reduced pressure to give the title compound (910 mg, Y.:87%) as yellow crystals.

$^1$H NMR; (DMSO-$d_6$) δ (ppm):3.9 (3H, s), 7.2 (1H, dd), 7.3 (1H, dd), 7.5 (1H, d), 8.0 (1H, d), 8.1 (1H, s), 11.9 (1H, brs).

ESI/MS (m/z):174 (M−H)$^-$.

In a similar procedure as employed in the Intermediate Example 29, compounds were synthesized according to the following reaction scheme. The synthesized compounds and data are shown in Table 2.

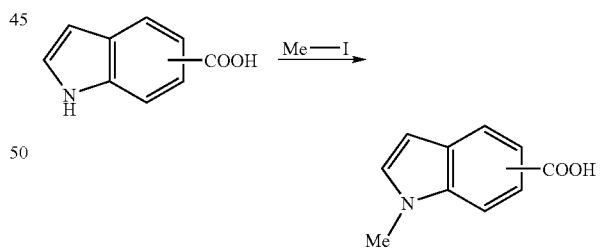

TABLE 2

| Intermediate Example | Compound Name | ESI/MS(m/z) |
|---|---|---|
| 30 | 1-methyl-1H-indole-4-carboxylic acid | 174 (M − H)$^-$ |
| 31 | 1-methyl-1H-indole-5-carboxylic acid | 176 (M + H)$^+$ 174 (M − H)$^-$ |
| 32 | 1-methyl-1H-indole-6-carboxylic acid | 176 (M + H)$^+$ 174 (M − H)$^-$ |

INTERMEDIATE EXAMPLE 33

1-Methyl-1H-indole-7-carboxylic acid

Methyl 1H-indole-7-carboxylate (546 mg) was dissolved in N,N-dimethylformamide (8 ml) and cooled to 0° C. Sodium hydride (370 mg) was added thereto and stirred as such for 30 minutes. Methyl iodide (0.38 ml) was added slowly dropwise thereto, and the mixture was warmed to room temperature and stirred for 2 hours. The mixture was diluted with ethyl acetate, and the organic phase was washed with 2 N hydrochloric acid, a saturated sodium bicarbonate solution and a saturated saline solution.

The resulting product was dried over sodium sulfate anhydrous and then concentrated under reduced pressure.

1,4-Dioxane (14 ml) and 1 N sodium hydroxide solution (14 ml) were added to the above compound and stirred for 17 hours at 40° C. The mixture was acidified by 2 N hydrochloric acid and extracted with chloroform. The extract was dried over sodium hydrous and then concentrated under reduced pressure. Precipitates were collected by filtration, washed with n-hexane and dried under reduced pressure to give the title compound (296 mg, Y.:55%).

$^1$H NMR (DMSO-d$_6$) δ (ppm):3.8 (1H, s), 6.5 (1H, d), 7.1 (1H, t), 7.4 (1H, d), 7.5 (1H, dd), 7.7 (1H, dd).

ESI/MS (m/z):176 (M+H)$^+$, 174 (M−H)$^-$.

In a similar procedure as employed in the Intermediate Example 33, compounds were synthesized according to the following reaction scheme. The synthesized compounds and data are shown in Table 3.

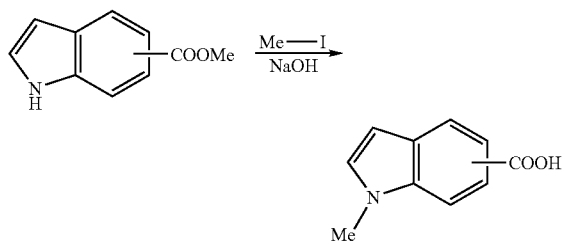

TABLE 3

| Intermediate Example | Compound Name | ESI/MS(m/z) |
|---|---|---|
| 34 | 4-methoxy-1-methyl-1H-indole-2-carboxylic acid | 204 (M − H)$^-$ |
| 35 | 6-methoxy-1-methyl-1H-indole-2-carboxylic acid | 206 (M + H)$^+$<br>204 (M − H)$^-$ |
| 36 | 4,6-dimethoxy-1-methyl-1H-indole-2-carboxylic acid | 236 (M + H)$^+$<br>234 (M − H)$^-$ |
| 37 | 5-methoxy-1,2-dimethyl-1H-indole-3-carboxylic acid | 220 (M + H)$^+$<br>218 (M − H)$^-$ |

INTERMEDIATE EXAMPLE 38

5-Methoxy-1-methyl-1H-indole-3-carboxylic acid

4-Methoxyphenylhydrazine hydrochloride (200 mg) and methyl 3,3-dimethoxypropionate (194 mg) were added to acetic acid (8.0 ml) and stirred for 4.5 hours at 70° C. The mixture was concentrated under reduced pressure, and the residue was purified by column chromatography (eluting solvent; ethyl acetate:n-hexane 1:5→1:3) to give methyl 5-methoxy-1H-indole-3-carboxylate (259 mg, Y.:97%).

$^1$H NMR; (DMSO-d$_6$) δ (ppm):3.8 (3H, s), 3.9 (3H, s), 6.8 (1H, dd), 7.4 (1H, d), 7.5 (1H, d), 8.0 (1H, s), 11.8 (1H, brs).

ESI/MS (m/z):204 (M−H)$^-$.

The methyl 5-methoxy-1H-indole-3-carboxylate (121 mg) obtained above was dissolved in N,N-dimethylformamide (1.5 ml) and cooled to 0° C. Sodium hydride (47 mg) was added thereto and stirred as such for 30 minutes. Methyl iodide (55 µl) was added dropwise thereto, and the mixture was warmed to room temperature and stirred for 1 hour. The reaction mixture was diluted with ethyl acetate, and the organic phase was washed with 2 N hydrochloric acid, a saturated sodium bicarbonate solution and a saturated saline solution. The resulting product was dried over sodium sulfate anhydrous and concentrated under reduced pressure.

1,4-Dioxane (4 ml) and 1 N sodium hydroxide solution (4 ml) were added to the above compound and stirred for 18 hours at 40° C. The mixture was acidified by 2 N hydrochloric acid, and precipitates were collected by filtration, washed with water and dried under reduced pressures to give the title compound (57 mg, Y.:52%).

$^1$H NMR; (DMSO-d$_6$) δ (ppm):3.7 (3H, s), 3.8 (3H, s), 6.8 (1H, dd), 7.4 (1H, d), 7.5 (1H, d), 7.9 (1H, s), 11.9 (1H, brs).

ESI/MS (m/z):206 (M+H)$^+$, 204 (M−H)$^-$.

INTERMEDIATE EXAMPLE 39

7-Methoxy-1-methyl-1H-indole-5-carboxylic acid

According to a method described in a literature (J. Org. Chem., 1996, 61, 5804-5812), the title compound was obtained from methyl 3-methoxy-4-anthranylate.

$^1$H NMR; (DMSO-d$_6$) δ (ppm):3.9 (3H, s), 4.0 (3H, s), 6.5 (1H, d), 7.2 (1H, s), 7.3 (1H, d), 7.9 (1H, s).

ESI/MS (m/z):206 (M+H)$^+$, 204 (M−H)$^-$.

INTERMEDIATE EXAMPLE 40

1-(2,2-Dimethylpropyl)-1H-indole-3-carboxylic acid

1H-Indole-3-carboxylic acid (208 mg) was dissolved in N,N-dimethylformamide (10 ml), then sodium hydride (154 mg) was added thereto, and the mixture was stirred for 10 minutes at room temperature. Neopentyl iodide (0.25 ml) was added to the reaction solution and stirred for 15 hours at 80° C. Water was added to the reaction mixture which was then washed with ethyl acetate. The aqueous phase was adjusted to pH 6 by 1 N hydrochloric acid, extracted with ethylacetate, and the extract was washed with a saturated saline solution and dried over sodium sulfate anhydrous. The resulting product was concentrated under reduced pressure, and the residue was purified by column chromatography (eluting solvent; n-hexane:ethyl acetate 4:1) to give the title compound (264 mg, Y.:89%).

$^1$H NMR; (CDCl$_3$) δ (ppm):1.0 (9H, s), 3.9 (2H, s), 7.2-7.3 (2H, m), 7.3-7.4 (1H, m), 7.9 (1H, s), 8.2-8.3 (1H, m).

ESI/MS (m/z):232 (M+H)$^+$, 230 (M−H)$^-$.

INTERMEDIATE EXAMPLE 41

1-Isobutyl-1H-indole-3-carboxylic acid

In a similar procedure as employed in the Intermediate Example 40, the title compound (121 mg, Y.:36%) was obtained by using 1H-indole-3-carboxylic acid (251 mg) and isobutyl iodide.

1H NMR; (CDCl$_3$) δ (ppm):0.9 (6H, d), 2.2-2.3 (1H, m), 3.9 (2H, d), 7.2-7.3 (2H, m), 7.3-7.4 (1H, m), 7.9 (1H, s), 8.2-8.3 (1H, m).
ESI/MS (m/z):218 (M+H)$^+$, 216 (M−H)$^-$.

INTERMEDIATE EXAMPLE 42

1-(2,2-Dimethylpropyl)-1H-indole-5-carboxylic acid

In a similar procedure as employed in the Intermediate Example 40, the title compound (473 mg, Y.:43%) was obtained by using methyl 1H-indole-5-carboxylate (825 mg) and neopentyl iodide.

$^1$H NMR; (CDCl$_3$) δ (ppm):1.0 (9H, s), 3.9 (2H, s), 6.6 (1H, d), 7.1 (1H, d), 7.3 (1H, d), 7.9 (1H, dd), 8.4 (1H, s).
ESI/MS (m/z):232 (M+H)$^+$, 230 (M−H)$^-$.

INTERMEDIATE EXAMPLE 43

1-Isobutyl-1H-indole-5-carboxylic acid

In a similar procedure as employed in the Intermediate Example 40, the title compound (375 mg, Y.:30%) was obtained by using methyl 1H-indole-5-carboxylate (1.02 g) and isobutyl iodide.

$^1$H NMR; (CDCl$_3$) δ (ppm):0.9 (6H, d), 2.1-2.2 (1H, m), 3.9 (2H, d), 6.6 (1H, d), 7.1 (1H, d), 7.3 (1H, d), 7.9 (1H, dd), 8.4 (1H, s).
ESI/MS (m/z):218 (M+H)$^+$, 216 (M−H)$^-$.

INTERMEDIATE EXAMPLE 44

1-Benzyloxymethyl-1H-indole-3-carboxylic acid

Methyl 1H-indole-3-carboxylate (1.00 g) was dissolved in N,N-dimethylformamide (12 ml) and cooled to 0° C. Sodium hydride (0.46 g) was added to the solution in two divided portions, and stirred as such for 30 minutes. Benzyloxymethyl chloride (2.4 ml) was added slowly dropwise thereto, and the mixture was warmed to room temperature and stirred for 2 hours. The reaction mixture was diluted with ethyl acetate, and the organic phase was washed with 2 N hydrochloric acid, a saturated sodium bicarbonate solution and a saturated saline solution. The resulting product was dried over sodium sulfate anhydrous and concentrated under reduced pressure.

1,4-Dioxane (20 ml) and 1 N sodium hydroxide solution (20 ml) were added to the above compound, and the mixture was stirred for 18 hours at 40° C. The reaction mixture was acidified by 2N hydrochloric acid and extracted with chloroform. The extract was dried over sodium sulfate anhydrous and concentrated under reduced pressure. The residue was crystallized from n-hexane and dried under reduced pressure to give the title compound (1.3 g, Y. :83%).

$^1$H NMR; (DMSO-d$_6$) δ (ppm):5.7 (2H, s), 7.2-7.4 (7H, m), 7.6 (1H, d), 8.0 (1H, d), 8.2 (1H, s).
ESI/MS (m/z):282 (M+H)$^+$, 280 (M−H)$^-$.

INTERMEDIATE EXAMPLE 45

1-Methoxymethyl-1H-indole-3-carboxylic acid

Methyl 1H-indole-3-carboxylate (500 mg) was dissolved in N,N-dimethylformamide (7.5 ml) and cooled to 0° C. Sodium hydride (340 mg) was added thereto and stirred as such for 30 minutes. Methoxymethyl chloride (0.43 ml) was added slowly dropwise thereto, and the mixture was warmed to room temperature and stirred for 1 hour. The reaction mixture was diluted with ethyl acetate, and the organic phase was washed with 2 N hydrochloric acid, a saturated sodium bicarbonate solution and a saturated saline solution. The resulting product was dried over sodium sulfate anhydrous and then concentrated under reduced pressure.

1,4-Dioxane (15 ml) and 1 N sodium hydroxide solution (15 ml) were added to the above compound and stirred for 16 hours at 40° C. The reaction mixture was acidified by 2 N hydrochloric acid and extracted with chloroform. The extract was dried over sodium sulfate anhydrous and then concentrated under reduced pressure. Precipitates were collected by filtration, washed with ether and dried under reduced pressure to give the title compound (342 mg, Y.:58%).

$^1$H NMR; (DMSO-d$_6$) δ (ppm):3.1 (3H, s), 5.6 (2H, s), 7.2-7.3 (2H, m), 7.6 (1H, d), 8.0 (1H, d), 8.2 (1H, d).
ESI/MS (m/z):206 (M+H)$^+$, 204 (M−H)$^-$.

INTERMEDIATE EXAMPLE 46

1-Acetoxymethyl-1H-indole-3-carboxylic acid

1H-Indole-3-carboxylic acid (400 mg) was dissolved in N,N-dimethylformamide (6 ml) and cooled to 0° C. Sodium hydride (500 mg) was added to the solution in two divided portions, and the mixture was stirred as such for 30 minutes. Bromomethyl acetate (0.32 ml) was added slowly dropwise thereto, and the mixture was stirred for 15 minutes at 0° C., warmed to room temperature and stirred for 45 minutes. The mixture was cooled to 0° C., and water was added to the mixture which was then acidified by 2 N hydrochloric acid and extracted with ethyl acetate. The extract was dried over sodium sulfate anhydrous and concentrated under reduced pressure. The residue was purified by column chromatography (eluting solvent; dichloromethane:methanol 50:1) to give the title compound (354 mg, Y.:61%).

$^1$H NMR; (DMSO-d$_6$) δ (ppm):2.0 (3H, s), 6.2 (2H, s), 7.2-7.4 (2H, m), 7.6 (1H, d), 7.9 (1H, s), 8.0 (1H, d).
ESI/MS (m/z):233 (M+H)$^+$.

INTERMEDIATE EXAMPLE 47

1-Benzyloxymethyl-1H-indole-5-carboxylic acid

Methyl 1H-indole-5-carboxylate (500 mg) was dissolved in N,N-dimethylformamide (6.0 ml). The solution was cooled to 0° C., and sodium hydride (230 mg) was added thereto and stirred for 30minutes. Benzylchloromethylether (1.2ml) was added thereto, and the mixture was stirred for 2 hours at room temperature. The reaction solution was extracted with ethyl acetate, and the organic phase was washed with 2 N hydrochloric acid, a saturated sodium bicarbonate solution and a saturated saline solution. The resulting product was dried over sodium sulfate anhydrous and then concentrated under reduced pressure. 1,4-Dioxane (10 ml) and 1 N sodium hydroxide solution (5 ml) were added to the residue and stirred for 22 hours at 40° C. The reaction mixture was acidified by 2 N hydrochloric acid and then extracted with chloroform. The extract was dried over sodium sulfate anhydrous and then concentrated under reduced pressure. Precipitates were collected by filtration, washed with n-hexane and dried under reduced pressure to give the title compound (740 mg, Y.: 92%).

$^1$H NMR; (DMSO-d$_6$) δ (ppm):4.4 (2H, s), 5.7 (2H, s), 6.6 (1H, d), 7.2-7.4 (5H, m), 7.6-7.7 (3H, m), 7.8 (1H, d), 8.2 (1H, s)
ESI/MS (m/z):280 (M−H)$^-$.

INTERMEDIATE EXAMPLE 48

1-Hydroxymethyl-1H-indole-5-carboxylic acid

The 1-benzyloxymethyl-1H-indole-5-carboxylic acid (380 mg) obtained in Intermediate Example 47 was suspended in ethanol (6.5 ml). 10% Palladium on carbon (190 mg) was added thereto and stirred for 47 hours at 60° C. in a hydrogen atmosphere. Insoluble matter was removed by filtration, and the filtrate was concentrated under reduced pressure. The residue was purified by column chromatography (eluting solvent; dichloromethane:methanol 50:1) to give the title compound (120 mg, Y.:48%).

$^1$H NMR; (DMSO-$d_6$) δ (ppm):5.5 (2H, s), 6.5 (1H, d), 7.5 (1H, d), 7.6 (1H, d), 7.7 (1H, d), 8.2 (1H, s).

INTERMEDIATE EXAMPLE 49

1-Methoxymethyl-1H-indole-5-carboxylic acid

In a similar procedure as employed in the Intermediate Example 45, the title compound (190 mg, Y.:70%) was obtained from methyl 1H-indole-5-carboxylate (500 mg) and chloromethyl methyl ether (0.43 ml).

$^1$H NMR; (DMSO-$d_6$) δ (ppm):5.5 (2H, s), 6.5 (1H, d), 7.5 (1H, d), 7.6 (1H, d), 7.7 (1H, d), 8.2 (1H, s).

INTERMEDIATE EXAMPLE 50

1-(2,2-Dimethylpropyl )-5-methoxy-1H-indole-3-carboxylic acid

Methyl 5-methoxy-1H-indole-5-carboxylate (357 mg) was dissolved in N,N-dimethylformamide (17 ml). Sodium hydride (209 mg) was added thereto in three divided portions and stirred as such for 15 minutes. Neopentyl iodide (0.35 ml) was added dropwise thereto and stirred for 15 hours at 80° C. The reaction mixture was diluted with ethyl acetate, and the organic phase was washed with 2 N hydrochloric acid, a saturated sodium bicarbonate solution and a saturated saline solution. The resulting product was dried over sodium sulfate anhydrous and then concentrated under reduced pressure. The residue was purified by preparative thin-layer chromatography (developing solvent; ethyl acetate:n-hexane 1:3) to give neopentyl 1-(2,2-dimethylpropyl)-5-methoxy-1H-indo-3-carboxylate (114 mg, Y.:20%) and methyl 1-(2,2-dimethylpropyl)-5-methoxy-1H-indole-3-carboxylate (130 mg, Y.: 27%).

1,4-Dioxane (2.5 ml) and 1 N sodium hydroxide solution (2.5 ml) were added to the neopentyl 1-2,2-dimethylpropyl)-5-methoxy-1H-indole-3-carboxylate (114 mg) obtained above, and the mixture was stirred for 15 hours at 40° C. Ethanol (3 ml) was added thereto and the mixture was stirred for 24 hours at 70° C. The reaction mixture was acidified by 2 N hydrochloric acid and extracted with chloroform. The extract was dried over sodium sulfate anhydrous and then concentrated under reduced pressure to give the title compound (73 mg, Y.:81%).

$^1$H NMR; (DMSO-$d_6$) δ (ppm):0.9 (9H, s), 3.7 (3H, s), 4.0 (2H, s), 6.8 (1H, dd), 7.4 (1H, d), 7.5 (1H, d), 7.8 (1H, s).
ESI/MS (m/z):262 (M+H)$^+$, 260 (M–H)$^-$.

INTERMEDIATE EXAMPLE 51

1-2,2-Dimethylpropyl)-5-methyl-1H-indole-3-carboxylic acid

From methyl 5-methyl-1H-indole-3-carboxylate, the title compound was obtained in the similar procedure as in Intermediate Example 50.

$^1$H NMR; (DMSO-$d_6$) δ (ppm):0.9 (9H, s), 2.4 (3H, s), 4.0 (2H, s), 7.0 (1H, d), 7.4 (1H, d), 7.8 (1H, s), 7.8 (1H, s).
ESI/MS (m/z):246 (M+H)$^+$, 244 (M–H)$^-$.

INTERMEDIATE EXAMPLE 52

1-2,2-Dimethylpropyl)-5-methyl-1H-indole-3-carboxylic acid 1-2,2-Dimethylpropyl)-5-methoxy-1H-indole-3-carboxylic acid (102 mg) was dissolved in dichloromethane (3 ml) and cooled to −78° C. 1 M Boron tribromide solution in dichloromethane (1.2 ml) was added slowly dropwise thereto, and the mixture was stirred for 1 hour while the temperature was returned from −78° C. to 0° C. The reaction mixture was diluted with chloroform and alkalinized by 1 N sodium hydroxide solution, and the organic phase was separated. The aqueous phase was acidified by 2 N hydrochloric acid, extracted with chloroform and dried over sodium sulfate anhydrous. The product was concentrated under reduced pressure to give the title compound (78 mg, Y.:80%).

1H NMR; (DMSO-$d_6$) δ (ppm):0.9 (9H, s), 3.9 (2H, s), 6.6 (1H, dd), 7.3-7.4 (2H, m), 7.8 (1H, s), 8.9 (1H, brs).
ESI/MS (m/z):248 (M+H)$^+$, 246 (M–H)$^-$.

INTERMEDIATE EXAMPLE 53

1-(2,2-Dimethylpropionyloxymethyl)-1H-indole-3-carboxylic acid

Sodium hydride (218 mg) was added to a solution of 1H-indole-3-carboxylic acid (400 mg) in N,N-dimethylformamide (4 ml) with ice cooling, and the mixture was stirred for 30 minutes. Chloromethyl2,2-dimethylpropionate (373 mg) was added thereto, and the mixture was warmed to room temperature and stirred for 2 hours. Water was added thereto, and the aqueous phase was washed with ether. The aqueous phase was acidified by 2 N hydrochloric acid and extracted with ether. The organic phase was washed with a saturated saline solution and dried over sodium sulfate anhydrous. The product was concentrated under reduced pressure to give the title compound (540 mg, Y.:79%) as orange crystals.

ESI/MS (m/z):276 (M+H)$^+$, 274 (M–H)$^-$.

INTERMEDIATE EXAMPLE 54

1-t-Butoxycarbonylmethyl-1H-indole-5-carboxylic acid

Sodium hydride (115 mg) was added to a solution of benzyl 1H-indole-5-carboxylate (600 mg) in N,N-dimethylformamide (2 ml) with ice cooling, and the mixture was stirred for 30 minutes. t-Butyl bromoacetate (562 mg) was added thereto and stirred for 2 hours. Water was added thereto, and the aqueous phase was neutralized and then extracted with dichloromethane. The organic phase was dried over sodium sulfate anhydrous. The product was concentrated under reduced pressure to give benzyl 1-t-butoxycarbonylmethyl-1H-indole-5-carboxylate (944 mg, Y.: quant.).

The benzyl 1-t-butoxycarbonylmethyl-1H-indole-5-carboxylate (800 mg) obtained above was dissolved in ethanol, then 5% palladium on carbon (160 mg) was added thereto, and the mixture was stirred overnight at room temperature in a hydrogen atmosphere. Insoluble matter was removed by filtration, and the filtrate was concentrated under reduced pressure to give the title compound (670 mg, Y.:quant.).

ESI/MS (m/z):276 (M+H)$^+$, 274 (M–H)$^-$.

INTERMEDIATE EXAMPLE 55

1-Methyl-2,3-dihydro-1H-indole-5-carboxylic acid

Dichloromethane (2 ml) and triethylsilane (1 ml) were added to 1-methyl-1H-indole-5-carboxylic acid (100 mg). The mixture was cooled to 0° C., trifluoroacetic acid (1 ml) was added dropwise thereto, and the mixture was warmed to room temperature and stirred for 2 hours. The reaction mixture was concentrated under reduced pressure, and precipitate was collected by filtration. The precipitate was washed with ether and dried under reduced pressure to give the title compound (66 mg, Y.:65%).

$^1$H NMR; (DMSO-d$_6$) δ (ppm):2.7 (3H, s), 2.9 (2H, t), 3.4 (2H, t), 6.4 (1H, d), 7.5 (1H, s), 7.6 (1H, d).

ESI/MS (m/z):178 (M+H)$^+$, 176 (M−H)$^-$.

INTERMEDIATE EXAMPLE 56

1-Acetyl-1H-indole-3-carboxylic acid

1H-Indole-3-carboxylic acid (400 mg) and sodium acetate (0.96 g) were suspended in acetic anhydride (4.8 ml). The mixture was stirred at 110° C. for 16 hours and extracted with chloroform. The organic phase was washed with 2 N hydrochloric acid, dried over sodium sulfate anhydrous, and concentrated under reduced pressure. The residue was purified by column chromatography (eluting solvent; dichloromethane:methanol 50:1) to give the title compound (170 mg, Y.:34%).

$^1$H NMR; (DMSO-d$_6$) δ (ppm):2.7 (3H, s), 7.3-7.4 (2H, m), 8.0-8.1 (1H, m), 8.3-8.4 (1H, m), 8.4-8.5 (1H, m).

ESI/MS (m/z):202 (M−H)$^-$.

INTERMEDIATE EXAMPLE 57

1-Acetyl-2,3-dihydro-1H-indole-5-carboxylic acid

1H-Indole-5-carboxylic acid (2.0 g) was dissolved in N,N-dimethylformamide (15 ml). Benzyl chloride (1.53 ml) and calcium carbonate (3.4 g) were added to the solution and stirred for 39 hours at room temperature. The mixture was diluted with ethyl acetate, and the organic phase was washed with 2 N hydrochloric acid, a saturated sodium bicarbonate solution and a saturated saline solution. The resulting product was dried over sodium sulfate anhydrous and then concentrated under reduced pressure. Precipitated solids were collected by filtration, washed with n-hexane and dried under reduced pressure to give 1H-benzyl indole-5-carboxylate (2.6 g, Y.:85%).

$^1$H NMR; (DMSO-d$_6$) δ (ppm):5.3 (2H, s), 6.6 (1H, s), 7.3-7.5 (7H, m), 7.7 (1H, d), 8.3 (1H, s), 11.5 (1H, brs).

ESI/MS (m/z):252 (M+H)$^+$, 250 (M−H)$^-$.

The 1H-benzyl indole-5-carboxylate (1.0g) obtained above was dissolved in N,N-dimethylformamide (10 ml). After the solution was cooled to 0° C., sodium hydride (0.32 g) was added to the solution which was then stirred for 30 minutes. Acetyl chloride (1.3 ml) was added thereto, and the mixture was stirred for 8 hours at room temperature. The reaction mixture was diluted with ethyl acetate, and the organic phase was washed with 2 N hydrochloric acid, a saturated sodium bicarbonate solution and a saturated saline solution. The organic phase was dried over sodium sulfate anhydrous and concentrated under reduced pressure. The residue was purified by colunm chromatography (eluting solvent; ethyl acetate:n-hexane 1:7→1:4) to give benzyl 1-acetyl-1H-indole-5-carboxylate (1.1 g, Y. 97%).

$^1$H NMR; (DMSO-d$_6$) δ (ppm):2.6 (3H, s), 5.3 (2H, s), 6.9 (1H, d), 7.3-7.5 (5H, m), 7.9 (1H, dd), 7.9 (1H, d), 8.3 (1H, d), 8.4 (1H, d).

ESI/MS (m/z):294 (M+H)$^+$, 292 (M−H)$^-$.

The benzyl 1-acetyl-1H-indole-5-carboxylate (550 mg) obtained above was suspended in ethanol (9 ml). 10% Palladium on carbon was added thereto, and the mixture was stirred for 16 hours at room temperature in a hydrogen atmosphere. Insoluble matter was removed by filtration, and the filtrate was concentrated under reduced pressure. Precipitated crystals were collected by filtration, washed with ether and dried under reduced pressure to give the title compound (180 mg, Y.:48%).

$^1$H NMR; (DMSO-d$_6$) δ (ppm):2.1 (3H, s), 3.1 (2H, t), 4.1 (2H, t), 7.7-7.8 (2H, m), 8.0 (1H, d).

ESI/MS (m/z):206 (M+H)$^+$, 204 (M−H)$^-$.

INTERMEDIATE EXAMPLE 58

1-Acetyl-1H-indole-5-carboxylic acid

1-Acetyl-2,3-dihydro-1H-indole-5-carboxylic acid (100 mg) was suspended in 1,4-dioxane (3 ml), and 2,3-dichloro-5,6-dicyano-p-benzoquinone (445 mg) was added thereto and stirred for 16 hours at 110° C. Solids were removed by filtration, and the filtrate was concentrated under reduced pressure. The residue was purified by preparative thin-layer chromatography (developing solvent; dichloromethane:methanol 20:1) to give the title compound (98 mg, Y.:99%).

$^1$H NMR; (DMSO-d$_6$) δ (ppm):2.6 (3H, s), 6.8 (1H, d), 7.9 (1H, d), 7.9 (1H, d), 8.2 (1H, s), 8.3 (1H, d)

ESI/MS (m/z):203 (M+H)$^+$, 202 (M−H)$^-$.

INTERMEDIATE EXAMPLE 59

1-Benzoyl-1H-indole-5-carboxylic acid

Sodium hydride (58 mg) was added to a solution of benzyl 1H-indole-5-carboxylate (300 mg) in N,N-dimethylformamide (2 ml) with ice cooling, and then stirred for 30 minutes. Benzoyl chloride (202 mg) was added thereto, and the mixture was stirred for 2 hours. The reaction mixture was diluted with dichloromethane, and the organic phase was washed with 2 N hydrochloric acid, a saturated sodium bicarbonate solution and a saturated saline solution. The organic phase was dried over sodium sulfate anhydrous. The product was concentrated under reduced pressure to give benzyl 1-benzoyl-1H-indole-5-carboxylate (500 mg, Y.:quant.) as pale orange crystals.

The benzyl 1-benzoyl-1H-indole-5-carboxylate (100 mg) obtained above was dissolved in ethanol, and 5% palladium on carbon (20 mg) was added thereto and stirred overnight at room temperature in a hydrogen atmosphere. Insoluble matter was removed by filtration, and the filtrate was concentrated under reduced pressure to give the title compound (50 mg, Y.:66%) as white crystals.

ESI/MS (m/z):266 (M+H)$^+$, 264 (M−H)$^-$.

INTERMEDIATE EXAMPLE 60

1-(2,2-Dimethylpropionyl)-1H-indole-5-carboxylic acid

Sodium hydride (53 mg) was added to a solution of benzyl 1H-indole-5-carboxylate (276 mg) in N,N-dimethylformamide (2 ml) with ice cooling, and the mixture was stirred for 30 minutes. 2,2-Dimethylpropionyl chloride (162 mg) was added thereto, and the mixture was stirred for 2 hours. Water was added thereto, and the aqueous phase was neutralized, extracted with dichloromethane, and the extract was dried over sodium sulfate anhydrous. The resulting product was concentrated under reduced pressure to give benzyl 1-(2,2-dimethylpropionyl)-1H-indole-5-carboxylate (320 mg, Y.:87%) as pale orange crystals.

The benzyl 1-(2,2-dimethylpropionyl)-1H-indole-5-carboxylate (220 mg) obtained above was dissolved in ethanol, and 5% palladium on carbon (44 mg) was added thereto and stirred overnight at room temperature in a hydrogen atmosphere. Insoluble matter was removed by filtration, and the filtrate was concentrated under reduced pressure to give the title compound (140 mg, Y.:86%).

ESI/MS (m/z):246 (M+H)$^+$, 244 (M−H)$^−$.

INTERMEDIATE EXAMPLE 61

4-Methoxybenzothiazole-6-carboxylic acid

4-Amino-3-methoxybenzoic acid (1.0 g) and ammonium thiocyanate (910 mg) were dissolved in methanol (15 ml). A solution of bromine (0.30 ml) in methanol (3.0 ml) was added slowly dropwise thereto at 0° C. Thereafter, the mixture was stirred for 2 hours at room temperature, and ice (50 g) was added thereto. Precipitated crystals were collected by filtration and dried under reduced pressure to give white crystals (760 mg) which were then stirred for 2 hours at 90° C. together with sodium sulfide (1.6 g) in a mixed solvent of water (3.0 ml) and ethanol (3.0 ml). After cooling, the reaction mixture was acidified by 90% formic acid, then precipitated crystals were collected by filtration and dried under reduced pressure to give 4-amino-5-mercapto-3-methoxybenzoic acid (670 mg, Y.:57%) as yellow crystals.

$^1$H NMR; (DMSO-d$_6$) δ (ppm):3.8 (3H, s), 7.1 (1H, brs), 7.4 (1H, brs).

ESI/MS (m/z):200 (M+H)$^+$, 198 (M−H)$^−$.

The 4-amino-5-mercapto-3-methoxybenzoic acid (670 mg) obtained above was heated at 50° C. in 90% formic acid (6.0 ml), and zinc powder (15 mg) was added thereto. The mixture was stirred for 2 hours at 100° C. and then cooled to room temperature, and precipitated crystals were collected by filtration, washed with water and dried under reduced pressure to give the title compound (470 mg, Y.:67%) as white crystals.

1H NMR; (DMSO-d$_6$) δ (ppm):4.0 (3H, s), 7.5 (1H, d), 8.3 (1H, d), 9.4 (1H, s).

ESI/MS (m/z):210 (M+H)$^+$, 208 (M−H)$^−$.

INTERMEDIATE EXAMPLE 62

5-Methoxybenzothiazole-6-carboxylic acid

By the similar procedure as in Intermediate Example 61, the title compound (1.3 g, Y.:38%) was obtained from 4-amino-2-methoxybenzoic acid (2.8 g).

ESI/MS (m/z):210 (M+H)$^+$, 208 (M−H)$^−$.

INTERMEDIATE EXAMPLE 63

4-Methoxy-2-methylbenzothiazole-6-carboxylic acid

4-Amino-3-mercapto-5-methoxybenzoic acid (500 mg) was dissolved in tetrahydrofuran (15 ml) and cooled at −78° C. Acetic anhydride (0.26 ml) was added thereto, and the mixture was warmed over 30 minutes to room temperature and stirred for 3 hours. The reaction mixture was concentrated under reduced pressure to give the title compound (550 mg, Y.:99%) as white crystals.

$^1$H NMR; (DMSO-d$_6$) δ (ppm):2.8 (3H, s), 3.9 (3H, s), 7.4 (1H, s), 8.2 (1H, s).

ESI/MS (m/z):222 (M−H)$^−$.

INTERMEDIATE EXAMPLE 64

4-Methoxy-2-trifluoromethylbenzothiazole-6-carboxylic acid

4-Amino-3-mercapto-5-methoxybenzoic acid (400 mg) was dissolved in tetrahydrofuran (15 ml) and cooled to −78° C. Trifluoroacetic anhydride (0.31 ml) was added thereto, and the mixture was warmed over 30 minutes to room temperature and stirred for 30 minutes. The reaction mixture was concentrated under reduced pressure to give the title compound (550 mg, Y.:99%) as white crystals.

$^1$H NMR; (DMSO-d$_6$) δ (ppm):4.0 (3H, s), 7.6 (1H, s), 8.5 (1H, s).

INTERMEDIATE EXAMPLE 65

2-Methylbenzothiazole-6-carboxylic acid

4-Aminobenzoic acid (13 g) and ammonium thiocyanate (6.9 g) were suspended in methanol (200 ml) and cooled at −15° C. on an ice bath. A methanol solution (40 ml) containing bromine (4.7 ml) was added slowly dropwise thereto. The mixture was warmed to room temperature and stirred for 2 hours, iced water (500 ml) was added thereto, and precipitated crystals were collected by filtration and washed with water and n-hexane. The product was dried under reduced pressure to give 4-amino-3-thiocyanatobenzoic acid (9.4 g, Y.:53%) as white crystals.

$^1$H NMR; (DMSO-d$_6$) δ (ppm):6.6 (2H, brs), 6.8 (1H, d), 7.7 (1H, dd), 7.9 (1H, d).

ESI/MS (m/z):193 (M−H)$^−$.

Sodium sulfide (25 g) was suspended in water (60 ml) and ethanol (60 ml), and after it was ascertained that the sodium sulfide had been dissolved at 40° C., the 4-amino-3-thiocyanatobenzoic acid (10 g) obtained above was added thereto. The solution was heated to 90° C. and stirred as such for 2 hours. The reaction mixture was cooled to room temperature, and 90% formic acid solution was added to the reaction mixture until it became acidic, and precipitated crystals were collected by filtration and washed with water and n-hexane. The product was dried under reduced pressure to give 4-amino-3-mercaptobenzoic acid (8.8 g, Y.:96%) as pale yellow crystals.

$^1$H NMR; (DMSO-d$_6$) δ (ppm):6.6 (2H, brs), 6.8 (1H, d), 7.7 (1H, dd), 7.9 (1H, d).

ESI/MS (m/z):168 (M−H)$^−$.

The 4-amino-3-mercaptobenzoic acid (170 mg) obtained above and thioacetamide (83 mg) were suspended in ethylene glycol (1.5 ml). Conc. hydrochloric acid (0.1 ml) was added thereto, and the mixture was stirred for 7 hours at 100° C. The mixture was cooled to room temperature, then cold water was added thereto, and precipitated crystals were collected by filtration and washed with water and n-hexane. The product was dried under reduced pressure to give the title compound (150 mg, Y.:78%) as white crystals.

ESI/MS (m/z):192 (M−H)$^−$.

INTERMEDIATE EXAMPLE 66

4-Methoxy-2-phenylbenzothiazole-6-carboxylic acid

4-Amino-3-mercapto-5-methoxybenzoic acid (600 mg) and thiobenzamide (450 mg) were suspended in ethylene glycol (10 ml). Conc. hydrochloric acid (1.0 ml) was added thereto, and the mixture was stirred for 7 hours at 60° C. The reaction mixture was cooled to room temperature, then cold water was added thereto, and precipitated crystals were collected by filtration and washed with water and n-hexane. The crystals were dried under reduced pressure to give the title compound (280 mg, Y.:32%) as white crystals.

$^1$H NMR; (DMSO-d$_6$) δ (ppm):4.0 (3H, s), 7.5 (1H, d), 7.5-7.6 (3H, m), 8.1-8.2 (2H, m), 8.3 (1H, d)

ESI/MS (m/z):284 (M−H)$^-$.

INTERMEDIATE EXAMPLE 67

2-Phenylbenzothiazole-6-carboxylic acid

By the similar procedure as in Intermediate Example 66, the title compound (1.9 g, Y.:74%) was obtained from 4-amino-3-mercaptobenzoic acid (1.7 g).

ESI/MS (m/z):254 (M−H)$^-$.

INTERMEDIATE EXAMPLE 68

2-Oxo-2,3-dihydrobenzothiazole-6-carboxylic acid

4-Amino-3-mercaptobenzoic acid (680 mg) was dissolved in tetrahydrofuran (20 ml), and potassium carbonate (550 mg) was added thereto and stirred for 30 minutes at room temperature. The mixture was cooled to −78° C., and triphosgene (400 mg) was added thereto and stirred for 1 hour. The mixture was warmed to room temperature and concentrated under reduced pressure until the volume of the solvent became ⅓. Water (20 ml) and formic acid were added to the concentrate until it became acidic, and precipitated crystals were collected by filtration and washed with water and n-hexane. The crystals were dried under reduced pressure to give the title compound (740 mg, Y.:95%) as white crystals.

1H NMR; (DMSO-d$_6$) δ (ppm):6.3 (1H, brs), 7.1 (1H, d), 7.8 (1H, d), 8.1 (1H, s).

ESI/MS (m/z):194 (M−H)$^-$.

INTERMEDIATE EXAMPLE 69

1-Methyl-1H-benzimidazole-5-carboxylic acid

Methyl 4-amino-3-nitrobenzoate (7.0 g), sodium hydroxide (5.7 g), potassium carbonate (4.9 g) and tetrabutylammonium bromide (0.22 g) were suspended in toluene (100 ml). The mixture was stirred for 1 hour at 40° C., and then dimethylsulfuric acid (7.7 ml) was added thereto and stirred for 2 hours. The reaction solution was extracted with ethyl acetate, and the extract was washed with water and dried over sodium sulfate anhydrous. The product was concentrated under reduced pressure to give methyl 4-methylamino-3-nitrobenzoate (7.3 g, Y.:97%).

$^1$H NMR; (DMSO-d$_6$) δ (ppm):3.0 (d, 3H), 3.8 (s, 3H), 7.0 (d, 1H), 8.00 (dd, 1H), 8.5-8.7 (brs, 1H), 8.6 (d, 1H).

ESI/MS (m/z):325 (M+H)$^+$, 323 (M−H)$^-$.

The methyl 4-methylamino-3-nitrobenzoate (6.3 g) obtained above was suspended in 1,4-dioxane (125 ml). 20% Palladium hydroxide (6.3 g) was added thereto, and the mixture was stirred for 91 hours at room temperature in a hydrogen atmosphere. Insoluble matter was removed by filtration, and the filtrate was concentrated under reduced pressure. The residue was purified by column chromatography (eluting solvent; ethyl acetate:n-hexane 1:4→2:3) to give methyl 3-amino-4-methylaminobenzoate (3.3 g, Y.:62%).

ESI/MS (m/z):181 (M+H)$^+$, 179 (M−H)$^-$.

The methyl 3-amino-4-methylaminobenzoate (3.3 g) obtained above was dissolved in formic acid (96 ml). Water (4 ml) was added thereto, and the solution was stirred for 3 hours at 90° C. The reaction solution was concentrated under reduced pressure, and ethyl acetate was added to the residue. The organic phase was washed with a saturated sodium bicarbonate solution and dried over sodium sulfate anhydrous. The product was concentrated under reduced pressure to give methyl 1-methyl-1H-benzimidazole-5-carbonate (3.4 g, Y.:97%).

$^1$H NMR; (DMSO-d$_6$) δ (ppm):3.8 (s, 3H), 3.8 (s, 3H), 7.6 (d, 1H), 7.9 (dd, 1H), 8.2 (d, 1H), 8.3 (s, 1H).

ESI/MS (m/z):191 (M+H)$^+$.

The methyl 1-methyl-1H-benzimidazole-5-carbonate (500 mg) obtained above was dissolved in methanol (10 ml). 1 N Sodium hydroxide solution (8 ml) was added thereto, and the mixture was stirred for 4 hours at room temperature. Water was added to the reaction mixture which was then acidified by formic acid. Precipitates were collected by filtration and dried under reduced pressure to give the title compound (367 mg, Y.:79%).

$^1$H NMR; (DMSO-d$_6$) δ (ppm):3.8 (s, 3H), 7.6 (d, 1H), 7.8 (dd, 1H), 8.2 (d, 1H), 8.3 (s, 1H).

INTERMEDIATE EXAMPLE 70

2-Methylbenzoxazole-6-carboxylic acid

4-Amino-3-hydroxybenzoic acid (4.9 g) was added to acetic acid (250 ml) and stirred for 3 days at 130° C. The solution was concentrated under reduced pressure, and precipitates were collected by filtration. The precipitates were dissolved in methanol and chloroform. The solution was concentrated under reduced pressure, and precipitates were collected by filtration, washed with methanol and dried under reduced pressure to give the title compound (3.5 g, Y.:62%).

$^1$H NMR; (DMSO-d$_6$) δ (ppm):2.6 (s, 3H), 7.7 (d, 1H), 7.9 (dd, 1H), 8.1 (d, 1H).

ESI/MS (m/z):178 (M+H)$^+$, 176 (M−H)$^-$.

INTERMEDIATE EXAMPLE 71

5-Methyl-2,3-dihydro-1H-isoindole

Xylene (15 ml) was added to 4-methylphthalic anhydride (3.0 g) and urea (1.2 g), and the mixture was stirred overnight at 150° C. The reaction mixture was cooled to room temperature, and precipitated crystals were collected by filtration and washed with ethanol and water. The crystals were dried under reduced pressure to give 4-methylphthalimide (2.4 g, Y.:82%) as white crystals.

1H NMR; (CDCl$_3$) δ (ppm):2.5 (3H, s), 7.5 (1H, d), 7.6 (1H, s), 7.7 (1H, s).

The 4-methylphthalimide (1.8 g) obtained above was suspended in tetrahydrofuran (3 ml), then 1 N borane tetrahydrofuran complex (30 ml) was added thereto at room temperature and stirred overnight at 60° C. The mixture was cooled to 0° C., then methanol (2.8 ml) and 6 N hydrochloric acid (3.2 ml) were added thereto, and the mixture was refluxed for 1 hour. The reaction mixture was cooled to 0° C., then 6 N sodium hydroxide solution was added thereto, and the reaction solution was extracted with ethyl acetate and then the extract was dried over sodium sulfate anhydrous. The resulting product was concentrated under reduced pressure, and the residue was purified by column chromatography (eluting solvent;

dichloromethane→dichloromethane:methanol 10:1→5:1) to give the title compound (400 mg, Y.:27%).

$^1$H NMR; (CDCl$_3$) δ (ppm):2.3 (3H, s), 2.7 (1H, brs), 7.0 (1H, d), 7.1 (1H, s), 7.2 (1H, d).

ESI/MS (m/z):134 (M+H)$^+$.

In a similar procedure as employed in the Intermediate Example 71, compounds were synthesized according to the following reaction scheme. The synthesized compounds and data are shown in Table 4. (Each symbol has the same meaning as defined above.)

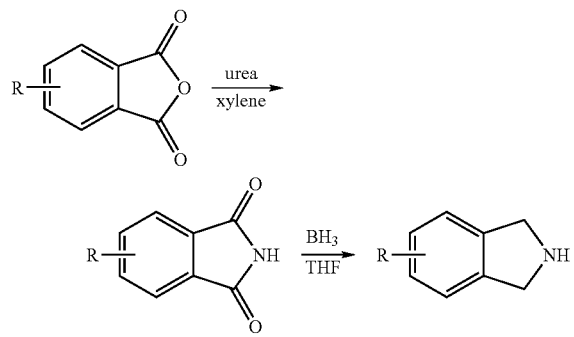

TABLE 4

| Intermediate Example | Compound Name | ESI/MS(m/z) |
|---|---|---|
| 72 | 5-fluoro-2,3-dihydro-1H-isoindole | 138 (M + H)$^+$ |
| 73 | 5-bromo-2,3-dihydro-1H-isoindole | 199 (M + H)$^+$ |
| 74 | 5-chloro-2,3-dihydro-1H-isoindole | 155 (M + H)$^+$ |
| 75 | 5-t-butyl-2,3-dihydro-1H-isoindole | 176 (M + H)$^+$ |
| 76 | 4-fluoro-2,3-dihydro-1H-isoindole | 138 (M + H)$^+$ |
| 77 | 4-methyl-2,3-dihydro-1H-isoindole | 134 (M + H)$^+$ |
| 78 | 4,7-dichloro-2,3-dihydro-1H-isoindole | 189 (M + H)$^+$ |
| 79 | 4-hydroxy-2,3-dihydro-1H-isoindole | 136 (M + H)$^+$ |
| 80 | 5-hydroxymethyl-2,3-dihydro-1H-isoindole | 150 (M + H)$^+$ |
| 81 | 5-trifluoromethyl-2,3-dihydro-1H-isoindole | 188 (M + H)$^+$ |
| 82 | 4,5,6,7-tetrachloro-2,3-dihydro-1H-isoindole | 258 (M + H)$^+$ |
| 83 | 5,6-dichloro-2,3-dihydro-1H-isoindole | 199 (M + H)$^+$ |
| 84 | 4-hydroxy-6-methyl-2,3-dihydro-1H-isoindole | 150 (M + H)$^+$ |
| 85 | 4-methoxy-6-methyl-2,3-dihydro-1H-isoindole | 164 (M + H)$^+$ |

INTERMEDIATE EXAMPLE 86

5-Methoxy-2,3-dihydro-1H-isoindole 3,4-Dimethylanisole (3.0 g) was added to carbon tetrachloride, and N-bromosuccinimide (7.9 g) and 2,2'-azobisisobutyronitrile (50 mg) were added thereto and refluxed overnight. The reaction mixture was cooled to room temperature, insoluble matter was removed by filtration, and the filtrate was concentrated under reduced pressure. The residue was purified by column chromatography (eluting solvent; n-hexane:ethyl acetate 25:1→20:1) to give 1,2-bisbromomomethyl-4-methoxybenzene (1.2 g, Y.:19%).

1H NMR; (CDCl$_3$) δ (ppm):3.8 (3H, s), 4.6 (2H, s), 4.6 (2H, s), 6.8 (1H, dd), 6.9 (1H, d), 7.2 (1H, d).

Sodium hydride (0.35 g) was suspended in N,N-dimethylformamide (1.2 ml), and a solution of p-toluenesulfonamide (0.71 g) in N,N-dimethylformamide (2 ml) was added thereto and stirred for 30 minutes at room temperature. The mixture was stirred for 1 hour at 60° C., and a solution of the 1,2-bisbromomethyl-4-methoxybenzene (1.2 g) obtained above in N,N-dimethylformamide (2 ml) was added at 60° C. to the mixture. The mixture was stirred for 3 hours at room temperature, then ethyl acetate was added thereto, and the reaction mixture was washed with water. The organic phase was dried over sodium sulfate anhydrous and concentrated under reduced pressure to give the corresponding sulfonyl derivative. This product was mixed with phenol (0.54 g), n-propanol (0.72 ml) and 48% hydrobromic acid (4.0 ml), and the mixture was stirred for 2 hours at 100° C. The reaction mixture was cooled and then washed with ethyl acetate. The aqueous phase was alkalinized, extracted with chloroform, and the extract was dried over sodium sulfate anhydrous. The product was concentrated under reduced pressure to give the title compound (89 mg, Y.:14%).

$^1$H NMR; (CDCl$_3$) δ (ppm):3.8 (3H, s), 4.1-4.2 (4H, m), 6.7-6.8 (2H, m), 7.1-7.2 (1H, m).

INTERMEDIATE EXAMPLE 87

4-Methoxy-2,3-dihydro-1H-isoindole

From 3,4-dimethylanisole, 4-methoxy-2,3-dihydro-1H-isoindole was synthesized by the similar procedure as in Intermediate Example 86.

H NMR; (CDCl$_3$) δ (ppm):3.8 (3H, s), 4.2-4.3 (4H, m), 6.7-7.2 (3H, m).

INTERMEDIATE EXAMPLE 88

2,3,4,5-Tetrahydro-1H-benzo[c]azepine

According to a method described in a literature (Tetrahedron, 1993, 49, 1807-1820), the title compound (2.0 g, Y.:55%) was obtained from 1-tetralone (3.3 ml).

ESI/MS (m/z):148 (M+H)$^+$.

INTERMEDIATE EXAMPLE 89

3-Amino-1-(1,3-dihydroisoindol-2-yl)-3-methylbutan-1-one 2,3-Dihydro-1H-isoindole (543 mg) and 3-amino-3-methylbutanoic acid (700 mg) were dissolved in N,N-dimethylformamide (30 ml). N-(3-Dimethylaminopropyl)-N'-ethylcarbodiimide hydrochloride (876 mg) and hydroxybenzotriazole (698 mg) were added thereto at 0° C., and then the mixture was stirred overnight at room temperature. The reaction mixture was concentrated under reduced pressure, and water and ethyl acetate were added to the residue. The organic phase was separated, and the aqueous phase was adjusted to pH 9 by adding a saturated sodium bicarbonate solution, and then extracted with ethyl acetate. The extract was dried over sodium sulfate and concentrated under reduced pressure to give the title compound (0.60 g, Y.:60%) as a brown oily matter.

$^1$H NMR; (CDCl$_3$) δ (ppm):1.2 (6H, s), 2.4 (2H, s), 4.7-4.8 (4H, m), 7.2-7.3 (4H, m).

ESI/MS (m/z):219 (M+H)$^+$.

In a similar procedure as employed in the Intermediate Example 89, compounds were synthesized according to the following reaction scheme. The synthesized compounds and data are shown in Tables 5 and 6. (Each symbol has the same meaning as defined above.)

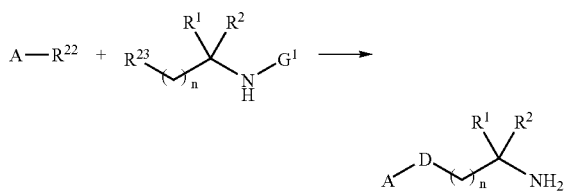

TABLE 5

| Intermediate Example | Compound Name | ESI/MS(m/z) |
| --- | --- | --- |
| 90 | 3-amino-3-methyl-1-(5-methyl-1,3-dihydroisoindol-2-yl)butan-1-one | 233 (M + H)+ |
| 91 | 3-amino-1-(5-fluoro-1,3-dihydroisoindol-2-yl)-3-methylbutan-1-one | 237 (M + H)+ |
| 92 | 3-amino-1-(5-bromo-1,3-dihydroisoindol-2-yl)-3-methylbutan-1-one | 298 (M + H)+ |
| 93 | 3-amino-1-(5-chloro-1,3-dihydroisoindol-2-yl)-3-methylbutan-1-one | 254 (M + H)+ |
| 94 | 3-amino-1-(5-t-butyl-1,3-dihydroisoindol-2-yl)-3-methylbutan-1-one | 275 (M + H)+ |
| 95 | 3-amino-1-(4-fluoro-1,3-dihydroisoindol-2-yl)-3-methylbutan-1-one | 237 (M + H)+ |
| 96 | 3-amino-3-methyl-1-(4-methyl-1,3-dihydroisoindol-2-yl)butan-1-one | 233 (M + H)+ |
| 97 | 3-amino-1-(4,7-dichloro-1,3-dihydroisoindol-2-yl)-3-methylbutan-1-one | 288 (M + H)+ |

TABLE 6

| Intermediate Example | Compound Name | ESI/MS(m/z) |
| --- | --- | --- |
| 98 | 3-amino-1-(4-hydroxy-1,3-dihydroisoindol-2-yl)-3-methylbutan-1-one | 235 (M + H)+ |
| 99 | 3-amino-1-(5-hydroxymethyl-1,3-dihydroisoindol-2-yl)-3-methylbutan-1-one | 249 (M + H)+ |
| 100 | 3-amino-3-methyl-1-(5-trifluoromethyl-1,3-dihydroisoindol-2-yl)butan-1-one | 287 (M + H)+ |
| 101 | 3-amino-3-methyl-1-(4,5,6,7-tetrachloro-1,3-dihydroisoindol-2-yl)butan-1-one | 357 (M + H)+ |
| 102 | 3-amino-1-(5,6-dichloro-1,3-dihydroisoindol-2-yl)-3-methylbutan-1-one | 288 (M + H)+ |
| 103 | 3-amino-1-(4-hydroxy-6-methyl-1,3-dihydroisoindol-2-yl)-3-methylbutan-1-one | 249 (M + H)+ |
| 104 | 3-amino-1-(4-methoxy-6-methyl-1,3-dihydroisoindol-2-yl)-3-methylbutan-1-one | 263 (M + H)+ |
| 105 | 3-amino-1-(5-methoxy-1,3-dihydroisoindol-2-yl)-3-methylbutan-1-one | 249 (M + H)+ |
| 106 | 3-amino-1-(4-methoxy-1,3-dihydroisoindol-2-yl)-3-methylbutan-1-one | 249 (M + H)+ |
| 107 | 3-amino-1-(3,4-dihydro-1H-isoquinolin-2-yl)-3-methylbutan-1-one | 233 (M + H)+ |
| 108 | 2-amino-1-(1,3-dihydroisoindol-2-yl)-2-methylpropan-1-one | 205 (M + H)+ |
| 109 | 2-amino-2-methyl-1-(1,3,4,5-tetrahydrobenzo[c]azepin-2-yl)propan-1-one | 233 (M + H)+ |
| 110 | 4-amino-1-(1,3-dihydroisoindol-2-yl)-4-methylpentan-1-one | 233 (M + H)+ |

INTERMEDIATE EXAMPLE 111

2-Methylpyrazolo[1,5-a]pyrimidine-6-carboxylic acid (2-amino-2-methylpropyl)amide 2-Methylpyrazolo[1,5-a]pyrimidine-6-carboxylic acid (0.18 g) was suspended in dichloromethane (5 ml), and N,N-dimethylformamide (1 drop) was added thereto. The mixture was cooled to 0° C., and a solution of oxalyl chloride (10 μl) in dichloromethane (3 ml) was added dropwise thereto over 10 minutes, and the mixture was stirred as such for 1 hour at 0° C. Thereafter, the mixture was stirred for 5 hours at room temperature to prepare the corresponding acid chloride. 2-Amino-2-methylpropylamine (0.11 g) was dissolved in dichloromethane, and triethylamine (0.33 ml) was added thereto and cooled to −78° C. The prepared acid chloride solution was added dropwise thereto over 30 minutes and stirred as such for 30 minutes. The temperature of the mixture was increased to room temperature, and the mixture was stirred for 1 hour at room temperature. Water was added thereto, and the aqueous phase was acidified by 2 N hydrochloric acid. After washing with chloroform, the aqueous phase was alkalinized by 5 N sodium hydroxide solution and extracted with chloroform. The organic phase was washed with a saturated saline solution and dried over sodium sulfate anhydrous. The product was concentrated under reduced pressure to give the title compound (0.14 g, Y.:56%) as yellow crystals.

ESI/MS (m/z):248 (M+H)+.

INTERMEDIATE EXAMPLE 112

2-Methylpyrazolo[1,5-a]pyrimidine-6-carboxylic acid (1-aminocyclopentylmethyl)amide 2-Methylpyrazolo[1,5-a]pyrimidine-6-carboxylic acid (0.31 g) was suspended in tetrahydrofuran (7 ml), and N,N-dimethylformamide (0.04 ml) was added thereto. A solution of oxalyl chloride (200 μl) in tetrahydrofuran (0.8 ml) was added dropwise thereto with ice cooling, and the mixture was stirred for 1 hour at the same temperature and then stirred for 2 hours at room temperature. Potassium carbonate (0.54 g) was added thereto at −60° C. or less, and then a solution of 1-(aminomethyl)cyclopentylamine (0.22 g) in tetrahydrofuran (0.8 ml) was added dropwise thereto. The mixture was stirred for 30 minutes at −60° C. or less and then stirred for 22 hours at room temperature. Water (6 ml) was added thereto on an ice bath, and the reaction mixture was adjusted to pH 2 by 6 N hydrochloric acid. The reaction mixture was washed with chloroform, and the aqueous phase was adjusted to pH 12 by 5 N sodium hydroxide solution and extracted with chloroform. The resulting product was washed with a saturated saline solution and then dried over sodium sulfate anhydrous. The product was concentrated under reduced pressure to give the title compound (57 mg, Y.:12%).

$^1$H NMR; (CDCl$_3$) δ (ppm):1.4-1.8 (8H, m), 2.5 (3H, s), 3.2-3.3 (2H, m), 6.5, 8.8, 9.2 (3H, s).

ESI/MS (m/z):274 (M+H)+, 272 (M−H)−.

INTERMEDIATE EXAMPLE 113

2-Methylpyrazolo[1,5-a]pyrimidine-6-carboxylic acid (4-amino-4-methylpentyl)amide 2-Methylpyrazolo[1,5-a]pyrimidine-6-carboxylic acid (177 mg) was suspended in tetrahydrofuran (5 ml), and N,N-dimethylformamide (1 drop) was added thereto. Oxalyl chloride (100 μl) was added thereto with ice cooling, and the mixture was stirred for 30 minutes at room temperature. The mixture was cooled again on ice, and 4-methyl-1,4-pentane <つめる>diamine (116 μl) and triethylamine (0.21 ml) were added thereto and stirred overnight at room temperature. By adding water and 2 N hydrochloric acid, the reaction mixture was acidified, followed by washing with chloroform. The aqueous phase was alkalinized by 5 N sodium hydroxide solution, extracted with chloroform, and the extract was dried over sodium sulfate anhydrous. The product was concentrated under reduced pressure to give the title compound (151 mg, Y.:55%) as pale yellow crystals.

$^1$H NMR; (CDCl$_3$) δ (ppm):1.1 (6H, s), 1.7 (4H, m), 2.5 (3H, s), 3.4 (2H, dd), 6.5 (1H, s), 8.4 (1H, brs), 8.7 (1H, d), 9.1 (1H, d).

ESI/MS (m/z):276 (M+H)$^+$, 274 (M−H)$^−$.

INTERMEDIATE EXAMPLE 114

Methyl 2-amino-3-[(benzothiazole-6-carbonyl)amino]propionate

Benzothiazole-6-carboxylic acid (358 mg), N-(3-dimethylaminopropyl)-N'-ethylcarbodiimide hydrochloride (382 mg) and hydroxybenzotriazole (306 mg) were dissolved in N,N-dimethylformamide (10 ml) and stirred for 30 minutes with ice cooling. A solution of methyl 3-amino-2-t-butoxycarbonylaminopropionate (560 mg) in N,N-dimethylformamide (8 ml) was added thereto, and the mixture was stirred for 17 hours at a temperature ranging from ice cooling to room temperature. The reaction mixture was concentrated under reduced pressure, and the organic phase was extracted by adding water and ethyl acetate. The organic phase was washed with 10% citric acid solution, 4% sodium bicarbonate solution and water, and dried over sodium sulfate anhydrous. The reaction product was concentrated under reduced pressure to give methyl 3-[(benzothiazole-6-carbonyl)amino]-2-t-butoxycarbonylamino propionate (750 mg, Y.:98.8%).

The methyl 3-[(benzothiazole-6-carbonyl)amino]-2-t-butoxycarbonylamino propionate (730 mg) obtained above was added to ice-cold trifluoroacetic acid (6ml) and stirred for 1 hour. The reaction mixture was concentrated under reduced pressure, and ether was added to the concentrate under cooling on ice to precipitate crystals, and the crystals were collected by filtration and dried under reduced pressure to give the title compound (817 mg, Y.: quant.).

ESI/MS (m/z):394 (M+H)$^+$.

INTERMEDIATE EXAMPLE 115

3-Amino-1-(1,3-dihydroisoindol-2-yl)propan-1-one

N-(3-Dimethylaminopropyl)-N'-ethylcarbodiimide hydrochloride (1.94 g) was added to a solution of 3-t-butoxycarbonylaminopropionic acid (1.90 g) in N,N-dimethylformamide at 0° C. A solution of 2,3-dihydro-1H-isoindole (1.00 g) in N,N-dimethylformamide was added thereto. The mixture was warmed to room temperature and stirred overnight. The reaction mixture was concentrated under reduced pressure, and water and dichloromethane were added to the residue. The organic phase was separated and washed with 10% citric acid solution, 4% sodium bicarbonate solution and a saturated saline solution. The product was dried over sodium sulfate anhydrous and concentrated under reduced pressure. Ether was added to precipitate crystals, and the crystals were collected by filtration and dried under reduced pressure to give t-butyl [3-(1,3-dihydroisoindole)-3-oxopropyl]carbamate (1.33 g, Y.:55%) as pale orange crystals.

The t-butyl [3-(1,3-dihydroisoindolyl)-3-oxopropyl]carbamate (1.33 g) obtained above was added to ice-cold trifluoroacetic acid (6 ml) and stirred as such for 30 minutes. The reaction solution was concentrated under reduced pressure, and ether was added to the residue, and precipitated crystals were collected by filtration and dried under reduced pressure to give the title compound (1.38 g, Y.:99%).

ESI/MS (m/z):191 (M+H)$^+$.

In a similar procedure as employed in the Intermediate Example 115, compounds were synthesized according to the following reaction scheme. The synthesized compounds and data are shown in in Table 7. (Each symbol has the same meaning as defined above.)

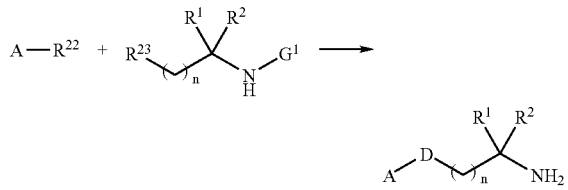

TABLE 7

| Intermediate Example | Compound Name | ESI/MS(m/z) |
|---|---|---|
| 116 | 3-amino-1-(3,4-dihydro-1H-isoquinolin-2-yl)propan-1-one | 205 (M + H)$^+$ |
| 117 | 3-amino-1-(2,3-dihydroindol-1-yl)propan-1-one | 191 (M + H)$^+$ |
| 118 | 4-amino-1-(1,3-dihydroisoindol-2-yl)butan-1-one | 205 (M + H)$^+$ |
| 119 | 3-amino-N-benzothiazol-2-ylpropionamide | 222 (M + H)$^+$ |

INTERMEDIATE EXAMPLE 120

3-Amino-1-indol-1-ylpropan-1-one

The t-butyl [3-(2,3-dihydroindol-1-yl)-3-oxopropyl]carbamate (290 mg) obtained as the intermediate in Intermediate Example 117, and 2,3-dichloro-5,6-dicyano-p-benzoquinone (510 mg) were suspended in chloroform (40 ml) and refluxed for 30 hours. The reaction mixture was cooled to room temperature, then insoluble matter was removed by filtration, the filtrate was washed with water, and the organic phase was dried over sodium sulfate anhydrous. The resulting product was concentrated under reduced pressure, and the residue was purified by column chromatography (eluting solvent; dichloromethane→dichloromethane:methanol 10:1) to give t-butyl (3-indol-1-yl-3-oxopropyl)carbamate (270 mg, Y.:95%).

ESI/MS (m/z):289 (M+H)$^+$, 287 (M−H)$^−$.

The t-butyl (3-indol-1-yl-3-oxopropyl)carbamate (260 mg) obtained above was added to ice-cold trifluoroacetic acid (2.0 ml) and stirred as such for 1 hour. The product was concentrated under reduced pressure, then ether was added to the residue, and precipitated white crystals were collected by filtration. The crystals were dried under reduced pressure to give a trifluoroacetate (260 g, Y.:94%) of the title compound.

$^1$H NMR; (DMSO-d$_6$) δ (ppm):3.2-3.3 (2H, m), 3.4 (2H, t), 6.8 (1H, d), 7.2 (1H, t), 7.3 (1H, t), 7.6 (1H, d), 7.8 (3H, brs), 7.9 (1H, d), 8.3 (1H, d).

ESI/MS (m/z):189 (M+H)$^+$, 187 (M−H)$^−$.

INTERMEDIATE EXAMPLE 121

1,3-Dimethyl-1H-pyrazolo[3,4-b]pyridine-5-carboxylic acid (2-aminoethyl)amide

Hydroxybenzotriazole (3.55 g) and N-(3-dimethylaminopropyl)-N'-ethylcarbodiimide hydrochloride (4.45 g) were added to a solution of 1,3-dimethyl-1H-pyrazolo[3,4-b]pyridine-5-carboxylic acid (4.00 g) in N,N-dimethylformamide (40 ml) with ice cooling. The mixture was stirred for 30 minutes at room temperature, and then t-butyl (2-aminoethyl)carbamate (3.65 ml) was added thereto and stirred overnight at room temperature. The reaction mixture was concentrated under reduced pressure, and ethyl acetate and water were added to the residue. The organic phase was washed with 10% citric acid solution, 4% sodium bicarbonate solution and a saturated saline solution. The product was dried under sodium sulfate anhydrous and concentrated under reduced pressure to give t-butyl {2-[(1,3-dimethyl-1H-pyrazolo[3,4-b]pyridine-5-carbonyl)amino]ethyl}carbamate (4.02 g, Y.:57%) as colorless crystals.

$^1$H NMR; (DMSO-d$_6$) δ (ppm):1.4 (9H, s), 2.5 (3H, s), 3.4-3.6 (4H, m), 4.1 (3H, s), 5.0, 7.5 (2H, brs), 8.4 (1H, s), 9.0 (1H, s).

The t-butyl {2-[(1,3-dimethyl-1H-pyrazolo[3,4-b]pyridine-5-carbonyl)amino]ethyl}carbamate (4.02 g) obtained above was added to ice-cold trifluoroacetic acid (20 ml) and stirred as such for 2 hours. The reaction mixture was concentrated under reduced pressure, then ether was added thereto, and precipitated crystals were collected by filtration. The product was dried under reduced pressure to give the title compound (3.52 g, Y.:84%) as pale yellow crystals.

$^1$H NMR; (DMSO-d$_6$) δ (ppm):2.5 (3H, s), 3.0-3.1 (2H, m), 3.5-3.6 (2H, m), 4.0 (3H, s), 7.8 (3H, brs), 8.7 (1H, s), 8.8 (1H, brt), 9.0 (1H, s).

In a similar procedure as employed in the Intermediate Example 121, compounds were synthesized according to the following reaction scheme. The synthesized compounds and data are shown in Table 8. (Each symbol has the same meaning as defined above.)

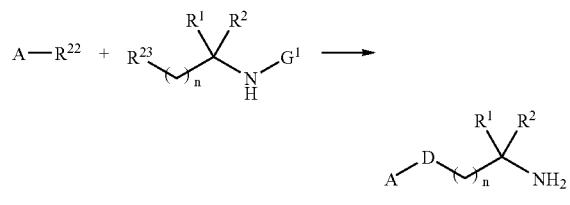

TABLE 8

| Intermediate Example | Compound Name | ESI/MS(m/z) |
|---|---|---|
| 122 | benzothiazole-6-carboxylic acid (2-aminoethyl)amide | 222 (M + H)$^+$ |
| 123 | 2-methylbenzothiazole-6-carboxylic acid (2-aminoethyl)amide | 236 (M + H)$^+$ |
| 124 | 5-methoxybenzothiazole-6-carboxylic acid (2-aminoethyl)amide | 252 (M + H)$^+$ |
| 125 | 4-methoxybenzothiazole-6-carboxylic acid (2-aminoethyl)amide | 252 (M + H)$^+$ |
| 126 | 2-phenylbenzothiazole-6-carboxylic acid (2-aminoethyl)amide | 298 (M + H)$^+$ |
| 127 | benzothiazole-6-carboxylic acid (4-aminobutyl)amide | 250 (M + H)$^+$ |
| 128 | 1-methyl-1H-indole-2-carboxylic acid (2-aminoethyl)amide | 218 (M + H)$^+$ |
| 129 | isoquinoline-3-carboxylic acid (2-aminoethyl)amide | 216 (M + H)$^+$ |
| 130 | isoquinoline-1-carboxylic acid (2-aminoethyl)amide | 216 (M + H)$^+$ |
| 131 | quinoline-3-carboxylic acid (2-aminoethyl)amide | 216 (M + H)$^+$ |
| 132 | quinoline-2-carboxylic acid (2-aminoethyl)amide | 216 (M + H)$^+$ |
| 133 | 5-oxo-2,3-dihydro-5H-thiazolo[3,2-a]pyrimidine-6-carboxylic acid (2-aminoethyl)amide | 241 (M + H)$^+$ |
| 134 | 2,7-dimethylpyrazolo[1,5-a]pyrimidine-6-carboxylic acid (2-aminoethyl)amide | 234 (M + H)$^+$ |
| 135 | 2,3-dihydrobenzo[1,4]dioxane-6-carboxylic acid (2-aminoethyl)amide | 223 (M + H)$^+$ |
| 136 | 2-methylimidazo[1,2-a]pyridine-3-carboxylic acid (2-aminoethyl)amide | 219 (M + H)$^+$ |
| 137 | 8-ethyl-5-oxo-2-pyrrolidin-1-yl-5,8-dihydropyrido[2,3-d]pyrimidine-6-carboxylic acid (2-aminoethyl)amide | 331 (M + H)$^+$ |

INTERMEDIATE EXAMPLE 138

{t-Butoxycarbonyl-[2-(1,3-dihydroisoindol-2-yl)-2-oxoethyl]amino}acetic acid

Boc-imidine acetic acid (580 mg) was dissolved in N,N-dimethylformamide (3.5 ml), and N-(3-dimethylaminopropyl)-N'-ethylcarbodiimide hydrochloride (480 mg) was added thereto and stirred for 1 hour at room temperature. 2,3-Dihydro-1H-isoindole (280 µl) was added thereto, and the mixture was stirred overnight at room temperature. The mixture was concentrated under reduced pressure, and 10% citric acid solution and ethyl acetate were added to the residue. The organic phase was separated, then washed with 4% sodium bicarbonate solution and a saturated saline solution, and dried over sodium sulfate anhydrous. The product was concentrated under reduced pressure, and the residue was purified by column chromatography (eluting solvent; dichloromethane:methanol 20:1→10:1) to give the title compound (270 mg, Y.:33%).

$^1$H NMR; (DMSO-d$_6$) δ (ppm):1.4 (9H, s), 3.9 (2H, s), 4.2 (2H, s), 4.8 (4H, d), 7.2-7.3 (4H, m).

ESI/MS (m/z):335 (M+H)$^+$, 333 (M−H)$^−$.

In a similar procedure as employed in the Intermediate Example 138, compounds were synthesized according to the following reaction scheme. The synthesized compounds and data are shown in Table 9. (Each symbol has the same meaning as defined above. )

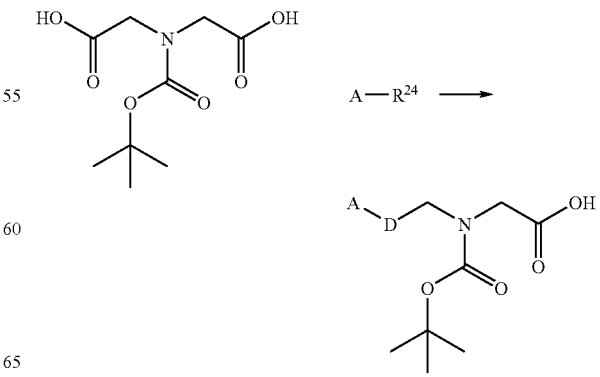

TABLE 9

| Intermediate Example | Compound Name | ESI/MS(m/z) |
|---|---|---|
| 139 | {t-butoxycarbonyl-[2-(2,3-dihydroindol-1-yl)-2-oxoethyl]amino}-acetic acid | 335 (M + H)+<br>336 (M − H)− |
| 140 | {t-butoxycarbonyl-[2-(3,4-dihydro-1H-isoquinolin-2-yl)-2-oxoethyl]amino}-acetic acid | 349 (M + H)+<br>347 (M − H)− |
| 141 | {t-butoxycarbonyl-[2-(3,4-dihydro-2H-quinolin-1-yl)-2-oxoethyl]amino}-acetic acid | 349 (M + H)+<br>347 (M − H)− |
| 142 | {t-butoxycarbonyl(isoquinolin-3-ylcarbonylmethyl)amino}acetic acid | 360 (M + H)+<br>358 (M − H)− |
| 143 | [t-butoxycarbonyl(quinolin-2-ylcarbonylmethyl)amino]acetic acid | 360 (M + H)+<br>358 (M − H)− |
| 144 | {t-butoxycarbonyl-[(2-methylquinolin-4-ylcarbonyl)methyl]amino}acetic acid | 374 (M + H)+<br>372 (M − H)− |
| 145 | {t-butoxycarbonyl-[(3-methylcinnolin-5-ylcarbonyl)methyl]amino}acetic acid | 375 (M + H)+<br>373 (M − H)− |
| 146 | {t-butoxycarbonyl-[(4-methyl-2-oxo-2H-chromen-7-ylcarbonyl)methyl]amino}-acetic acid | 391 (M + H)+<br>389 (M − H)− |
| 147 | [(benzothiazol-2-ylcarbonylmethyl)-t-butoxycarbonylamino]acetic acid | 366 (M + H)+<br>364 (M − H)− |
| 148 | {t-butoxycarbonyl-[(9H-purin-6-ylcarbonyl)methyl]amino}acetic acid | 351 (M + H)+<br>349 (M − H)− |
| 149 | {t-butoxycarbonyl-[(2-methylsulfanyl[1,2,4]triazolo[1,5-a]pyrimidin-7-ylcarbonyl)methyl]amino}acetic acid | 397 (M + H)+<br>395 (M − H)− |
| 150 | {t-butoxycarbonyl-[2-(octahydroquinolin-1-yl)-2-oxoethyl]amino}acetic acid | 355 (M + H)+<br>353 (M − H)− |

EXAMPLE 1

(S)-2,7-Dimethylpyrazolo[1,5-a]pyrimidine-6-carboxylic acid {2-[(2-cyanopyrrolidin-1-yl)-2-oxoethylamino]-2-methylpropyl}amide N,N'-Carbonyldiimidazole (930 mg) was added to a solution of 2,7-dimethylpyrazolo[1,5-a]pyrimidine-6-carboxylic acid (1.00 g) in tetrahydrofuran (30 ml), and the mixture was stirred for 4 hours at room temperature. The reaction mixture was added slowly dropwise to a solution of (S)-1-[(2-amino-1,1-dimethylethyl)aminoacetyl]pyrrolidine-2-carbonitrile dihydrochloride (1.56 g) and triethylamine (3.6 ml) in tetrahydrofuran (30 ml) with ice cooling. The mixture was warmed to room temperature and stirred overnight. The reaction mixture was concentrated under reduced pressure, and dichloromethane was added to the residue. Insoluble matter was removed by filtration, and the filtrate was concentrated under reduced pressure. The residue was purified by column chromatography (eluting solvent; dichloromethane:methanol 50:1) to give the title compound (690 mg, Y.:33%). 4N Hydrochloric acid/1,4-dioxane (0.50 ml) was added to a solution of the resulting compound (690 mg) in 1,4-dioxane (5.0 ml) at 10° C. and stirred for 10 minutes. Crystals were precipitated by adding ether and then collected by filtration. The crystals were dried under reduced pressure to give a hydrochloride (670 mg, Y.:90%) of the title compound as yellow crystals.

1H NMR; (DMSO-$d_6$) δ (ppm):1.37 (6H, s), 2.05-2.31 (4H, m), 2.47 (3H, s), 2.87 (3H, s), 3.30-3.80 (4H, m), 4.10-4.30 (2H, m), 4.84-4.86 (1H, m), 6.60 (1H, s), 8.68 (1H, s), 8.93-8.97 (3H, m).

In a similar procedure as employed in the Example 1, compounds were synthesized according to the following reaction scheme. The synthesized compounds and data are shown in Tables 10 to 17.

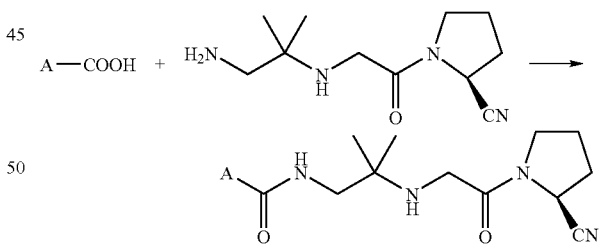

TABLE 10

| Example | A | ESI/MS(m/z) | 1H NMR |
|---|---|---|---|
| 2 | 2-methylpyrazolo-[1,5-a]pyrimidin-6-yl | 384(M+H)+<br>382(M−H)− | (DMSO-$d_6$)δ(ppm): 1.36(6H, s), 2.00-2.30(4H, m), 2.50(3H, s), 3.30-3.80(4H, m), 4.10-4.30(2H, m), 4.80(1H, m), 6.63(1H, s), 8.80-8.90(3H, m), 9.50(1H, s). |
| 3 | 2,5,7-trimethyl-pyrazolo[1,5-a]-pyrimidin-6-yl | 412(M+H)+<br>410(M−H)− | (DMSO-$d_6$)δ(ppm): 1.37(6H, s), 1.98-2.09(2H, m), 2.18-2.27(2H, m), 2.43(3H, s), 2.47(3H, s), 2.66(3H, s), 3.52-3.63(1H, m), 3.62(2H, d), 3.71-3.76(1H, m), 4.10-4.21(2H, m), |

TABLE 10-continued

| Example | A | ESI/MS(m/z) | ¹H NMR |
|---|---|---|---|
| | | | 4.86(1H, dd), 6.44(1H, s), 8.92(1H, brt), 9.12(2H, brs). |
| 4 | 7-methoxy-2,5-dimethylpyrazolo[1,5-a]pyrimidin-6-yl | 428(M+H)⁺ 426(M−H)⁻ | (DMSO-$d_6$)δ(ppm): 1.34(6H, s), 1.97-2.08(2H, m), 2.15-2.22(2H, m), 2.31(3H, s), 2.45(3H, s), 3.17(3H, s), 3.48-3.57(3H, m), 3.70-3.75(1H, m), 4.02-4.09(2H, m), 4.86(1H, dd), 6.30(1H, s), 8.68(1H, brt), 9.00-9.06(2H, m). |

TABLE 11

| Example | A | ESI/MS(m/z) | ¹H NMR |
|---|---|---|---|
| 5 | 5,7-dimethyl-2-phenylpyrazolo[1,5-a]pyrimidin-6-yl | 474(M+H)⁺ 472(M−H)⁻ | (DMSO-$d_6$)δ(ppm): 1.38(6H, s), 2.02-2.10(2H, m), 2.19-2.25(2H, m), 2.52(3H, s), 2.75(3H, s) 3.53-3.76(4H, m), 4.11(1H, dd), 4.18(1H, dd), 4.87(1H, dd), 7.18(1H, s), 7.44(1H, t), 7.51(2H, dd), 8.07(2H, d) 8.94(1H, t), 9.10(2H, brs). |
| 6 | 2-methyl-7-trifluoromethyl-pyrazolo[1,5-a]-pyrimidin-6-yl | 440(M+H)⁺ 438(M−H)⁻ | (DMSO-$d_6$)δ(ppm): 1.37(6H, s), 2.02-2.10(2H, m), 2.19-2.24(2H, m), 2.53(3H, s), 3.49-3.62(3H, m), 3.69-3.74(1H, m), 4.13-4.16(2H, m), 4.86(1H, dd), 6.94(1H, s), 9.00(2H, brs), 9.09(1H, t), 9.77(1H, s). |
| 7 | 2-t-butyl-5,7-dimethylpyrazolo[1,5-a]pyrimidin-6-yl | 454(M+H)⁺ 452(M−H)⁻ | (DMSO-$d_6$)δ(ppm): 1.36(15H, s), 2.01-2.10(2H, m), 2.19-2.24(2H, m), 2.47(3H, s), 2.66(3H, s) 3.51-3.71(4H, m), 4.11-4.19(2H, m), 4.87(1H, dd), 6.52(1H, s), 8.80(1H, t), 9.08(2H, brs). |
| 8 | 2-t-butyl-7-methylpyrazolo[1,5-a]pyrimidin-6-yl | 440(M+H)⁺ 438(M−H)⁻ | (DMSO-$d_6$)δ(ppm): 1.36(6H, s), 1.38(9H, s), 1.97-2.08(2H, m), 2.19-2.25(2H, m), 2.88(3H, s), 3.51-3.58(3H, m), 3.70-3.76(1H, m), 4.12-4.17(2H, m), 4.87(1H, dd), 6.73(1H, s), 8.68(1H, s), 8.91(1H, t), 8.95(2H, brs). |
| 9 | 7-methyl-2-phenyl-pyrazolo[1,5-a]-pyrimidin-6-yl | 460(M+H)⁺ 458(M−H)⁻ | (DMSO-$d_6$)δ(ppm): 1.39(6H, s), 2.03-2.11(2H, m), 2.19-2.25(2H, m), 2.96(3H, s), 3.54-3.69(4H, m), 4.11-4.23(2H, m) 4.88(1H, dd), 7.36(1H, s), 7.47(1H, t), 7.52(2H, dd), 8.10(2H, d) 8.77(1H, s), 9.01-9.06(3H, m). |
| 10 | 7-methoxy-5-methyl-2-phenyl-pyrazolo[1,5-a]-pyrimidin-6-yl | 490(M+H)⁺ 488(M−H)⁻ | (DMSO-$d_6$)δ(ppm): 1.36(6H, s), 2.01-2.09(2H, m), 2.19-2.28(2H, m), 2.48(3H, s), 3.52-3.58(3H, m), 3.71-3.73(1H, m), 3.77(3H, s), 4.87(1H, dd), 7.09(1H, s), 7.45(1H, t), 7.51(2H, t), 7.98(2H, d) 8.69(1H, t), 8.97-9.01(2H, m). |
| 11 | 5-hydroxy-2-methylpyrazolo[1,5-a]pyrimidin-6-yl | 400(M+H)⁺ 398(M−H)⁻ | (DMSO-$d_6$)δ(ppm): 1.31(6H, s), 2.05-2.27(4H, m), 2.32(3H, s), 3.52-3.68(5H, m), 3.96-4.08(2H, m), 4.82-4.85(1H, m), 6.15(1H, s), 8.55(1H, s), 9.36(1H, brt). |
| 12 | 7-hydroxy-2-methylpyrazolo[1,5-a]pyrimidin-6-yl | 400(M+H)⁺ 398(M−H)⁻ | (DMSO-$d_6$)δ(ppm): 1.22(6H, s), 2.05-2.27(4H, m), 2.28(3H, s), 3.48-3.53(4H, m), 3.63-3.69(1H, m), 3.79-3.89(2H, m), 4.79-4.82(1H, m), 5.97(1H, s), 8.47(1H, s), 9.65(1H, brt). |

TABLE 12

| Example | A | ESI/MS(m/z) | ¹H NMR |
|---|---|---|---|
| 13 | 2-hydroxymethyl-pyrazolo[1,5-a]-pyrimidin-6-yl | 400(M+H)⁺ 398(M−H)⁻ | (DMSO-$d_6$)δ(ppm): 1.05(6H, s), 1.96-2.23(4H, m), 3.16-3.51(5H, m), 3.60-3.66(1H, m), 4.68(2H, s), 4.72-4.75(1H, m), 5.39(1H, brs), 6.71(1H, s), 8.44(1H, brt), 8.87(1H, d), 9.44(1H, d). |
| 14 | 2-methoxymethyl-pyrazolo[1,5-a]-pyrimidin-6-yl | 414(M+H)⁺ 412(M−H)⁻ | (DMSO-$d_6$)δ(ppm): 1.35(6H, s), 1.98-2.29(4H, m), 3.36(3H, s), 3.57-4.15(6H, m), 4.63(2H, s), 4.82-4.85(1H, m), 6.77(1H, s), 8.94(1H, d), 9.11(1H, brt), 9.68(1H, d). |
| 15 | 1H-indol-3-yl | 368(M+H)⁺ 366(M−H)⁻ | (DMSO-$d_6$)δ(ppm): 1.04(6H, s), 1.90-2.20(4H, m), 3.15-3.30(2H, m), 3.35-3.50(3H, m), 3.60-3.70(1H, m), 4.74(1H, q), |

TABLE 12-continued

| Example | A | ESI/MS(m/z) | $^1$H NMR |
|---|---|---|---|
| 16 | 1H-indol-5-yl | 368(M+H)$^+$<br>366(M−H)$^−$ | 7.05-7.20(2H, m), 7.42(1H, d), 7.66(1H, brs), 8.05(1H, d), 8.10(1H, d), 11.56(1H, s).<br>(DMSO-d$_6$)δ(ppm): 1.33, 1.34(6H, 2s), 2.00-2.30(4H, m), 3.50-3.60(3H, m), 3.70-3.80(1H, m), 4.05-4.25(2H, m), 4.87(1H, q), 6.55(1H, s), 7.45(2H, t), 7.68(1H, dd), 8.21(1H, s), 8.59(1H, brt), 8.92(2H, brs), 11.43(1H, s). |
| 17 | 1-methyl-1H-indol-2-yl | 382(M+H)$^+$<br>380(M−H)$^−$ | (DMSO-d$_6$)δ(ppm): 1.34(6H, s), 1.95-2.15(2H, m), 2.15-2.30(2H, m), 3.45-3.65(3H, m), 3.70-3.80(1H, m), 3.98(3H, s), 4.00-4.25(2H, m), 4.87(1H, m), 7.12(1H, t), 7.24(1H, s), 7.29(1H, t), 7.54(1H, d), 7.66(1H, d), 8.73(1H, brs), 8.91(2H, brs). |
| 18 | 1-methyl-1H-indol-3-yl | 382(M+H)$^+$<br>380(M−H)$^−$ | (DMSO-d$_6$)δ(ppm): 1.33(6H, s), 2.00-2.24(4H, m), 3.53-3.57(5H, m), 3.67-3.75(1H, m), 3.85(3H, s), 4.12(1H, ddd), 4.16(1H, ddd), 4.86(1H, dd), 7.17(1H, dd), 7.24(1H, dd), 7.51(1H, d), 8.13(1H, d), 8.15(1H, s), 8.25(1H, t), 8.94(2H, brs). |
| 19 | 1-methyl-1H-indol-4-yl | 382(M+H)$^+$<br>380(M−H)$^−$ | (DMSO-d$_6$)δ(ppm): 1.35(6H, s), 2.00-2.30(4H, m), 3.50-3.65(3H, m), 3.65-3.80(1H, m), 3.83(3H, s), 4.00-4.25(2H, m), 4.86(1H, q), 6.84(1H, d), 7.24(1H, t), 7.44(1H, d), 7.57(1H, d), 7.64(1H, d), 8.51(1H, brt), 8.93(2H, brs). |
| 20 | 1-methyl-1H-indol-5-yl | 382(M+H)$^+$<br>380(M−H)$^−$ | (DMSO-d$_6$)δ(ppm): 1.34(6H, s), 1.90-2.30(4H, m), 3.20-3.45(2H, m), 3.45-3.65(2H, m), 3.70-3.80(1H, m), 3.83(3H, s), 4.00-4.25(2H, m), 4.87(1H, q), 6.55(1H, d), 7.43(1H, d), 7.51(1H, d), 7.73(1H, d), 8.20(1H, s), 8.59(1H, brs), 8.89(2H, brs). |

TABLE 13

| Example | A | ESI/MS(m/z) | $^1$H NMR |
|---|---|---|---|
| 21 | 1-methyl-1H-indol-6-yl | 382(M+H)$^+$<br>380(M−H)$^−$ | (DMSO-d$_6$)δ(ppm): 1.34(6H, s), 2.00-2.25(4H, m), 3.50-3.60(3H, m), 3.65-3.80(1H, m), 3.86(3H, s), 4.05-4.25(2H, m), 4.87(1H, q), 6.48(1H, d), 7.52(1H, d), 7.62(2H, s), 8.06(1H, s), 8.63(1H, brt), 8.80-9.00(2H, brs). |
| 22 | 1-methyl-1H-indol-7-yl | 382(M+H)$^+$<br>380(M−H)$^−$ | (DMSO-d$_6$)δ(ppm): 1.37(6H, s), 1.95-2.15(2H, m), 2.15-2.30(2H, m), 3.50-3.65(3H, m), 3.65-3.80(1H, m), 3.76(3H, s), 4.05-4.25(2H, m), 4.86(1H, m), 6.51(1H, d), 7.08(1H, dd), 7.33(1H, d), 7.36(1H, d), 7.67(1H, d), 8.71(1H, brs), 8.95(1H, brs). |
| 23 | 4-methoxy-1-methyl-1H-indol-2- | 412(M+H)$^+$<br>410(M−H)$^−$ | (DMSO-d$_6$)δ(ppm): 1.33(6H, s), 2.00-2.15(2H, m), 2.15-2.30(2H, m), 3.50-3.60(3H, m), 3.70-3.80(1H, m), 3.90(3H, s), 3.96(3H, s), 4.05-4.25(2H, m), 4.88(1H, m), 6.60(1H, d), 7.12(1H, d), 7.22(1H, t), 7.34(1H, s), 8.63(1H, brt), 8.92(2H, brs). |
| 24 | 6-methoxy-1-methyl-1H-indol-2-yl | 412(M+H)$^+$<br>410(M−H)$^−$ | (DMSO-d$_6$)δ(ppm): 1.32(6H, s), 2.00-2.15(2H, m), 2.15-2.30(2H, m), 3.45-3.60(3H, m), 3.70-3.80(1H, m), 3.83(3H, s), 3.95(3H, s), 4.00-4.25(2H, m), 4.87(1H, m), 6.75(1H, d), 7.02(1H, s), 7.18(1H, s), 7.53(1H, d), 8.60(1H, s), 8.90(2H, brs). |
| 25 | 4,6-dimethoxy-1-methyl-1H-indol-2-yl | 442(M+H)$^+$<br>440(M−H)$^−$ | (DMSO-d$_6$)δ(ppm): 1.32(6H, s), 1.95-2.15(2H, m), 2.15-2.30(2H, m), 3.45-3.60(3H, m), 3.70-3.80(1H, m), 3.82(3H, s), 3.86(3H, s), 3.92(3H, s), 4.00-4.25(2H, m), 4.87(1H, m), 6.24(1H, s), 6.62(1H, s), 7.27(1H, s), 8.49(1H, brt), 8.88(2H, brs). |
| 26 | 5-methoxy-1,2-dimethyl-1H-indol-3-yl | 426(M+H)$^+$ | (DMSO-d$_6$)δ(ppm): 1.40(6H, s), 2.00-2.30(4H, m), 2.62(3H, s), 3.30-3.80(4H, m), 3.68(3H, s), 3.80(3H, s), 4.83-3.86(1H, m), 6.83(1H, dd), 7.32(1H, d), 7.40(1H, d), 7.80(1H, brs), 8.80-9.00(2H, m). |

TABLE 13-continued

| Example | A | ESI/MS(m/z) | ¹H NMR |
|---|---|---|---|
| 27 | 5-methoxy-1-methyl-1H-indol-3-yl | 412(M+H)⁺ 410(M−H)⁻ | (DMSO-d₆)δ(ppm): 1.31(6H, s), 2.00-2.15(2H, m), 2.15-2.30(2H, m), 3.50-3.60(3H, m), 3.70-3.80(1H, m), 3.77(3H, s), 3.82(3H, s), 4.05-4.25(2H, m), 4.86(1H, m), 6.87(1H, dd), 7.42(1H, d), 7.64(1H, d), 8.05(1H, s), 8.14(1H, brt), 8.89(2H, brs). |
| 28 | 7-methoxy-1-methyl-1H-indol-5-yl | 412(M+H)⁺ 410(M−H)⁻ | (DMSO-d₆)δ(ppm): 1.33(6H, s), 2.00-2.15(2H, m), 2.15-2.30(2H, m), 3.50-3.60(3H, m), 3.70-3.80(1H, m), 3.94(3H, s), 4.02(3H, s), 4.00-4.25(2H, m), 4.87(1H, m), 6.49(1H, d), 7.19(1H, s), 7.30(1H, d), 7.82(1H, s), 8.64(1H, brt), 8.93(2H, brs). |

TABLE 14

| Example | A | ESI/MS(m/z) | ¹H NMR |
|---|---|---|---|
| 29 | 1-(2,2-dimethyl-propyl)-1H-indol-3-yl | 438(M+H)⁺ 436(M−H)⁻ | (CDCl₃)δ(ppm): 1.02(9H, s), 1.18(6H, s), 2.12-2.29(4H, m), 3.36-3.47(6H, m), 3.57-3.70(1H, m), 3.94(2H, s), 4.68-4.73(1H, m), 6.94-7.05(1H, m), 7.23-7.25(1H, m), 7.37-7.39(1H, m), 7.79(1H, s), 8.10-8.13(1H, m). |
| 30 | 1-isobutyl-1H-indol-3-yl | 424(M+H)⁺ 422(M−H)⁻ | (CDCl₃)δ(ppm): 0.94(6H, d), 1.19(6H, s), 2.10-2.29(5H, m), 3.37-3.48(6H, m), 3.58-3.62(1H, m), 3.93(2H, d), 4.67-4.75(1H, m), 6.87-6.97(1H, m), 7.25-7.27(1H, m), 7.35-7.37(1H, m), 7.78(1H, s), 8.11-8.13(1H, m). |
| 31 | 1-(2,2-dimethyl-propyl)-1H-indol-5-yl | 438(M+H)⁺ 436(M−H)⁻ | (DMSO-d₆)δ(ppm): 0.93(9H, s), 1.35(6H, s), 1.98-2.29(4H, m), 3.54-3.62(5H, m), 3.71-3.74(1H, m), 4.03(2H, d), 4.07-4.19(2H, m), 4.84-4.86(1H, m), 6.56(1H, d), 7.38(1H, d), 7.58(1H, d), 7.72(1H, dd), 8.20(1H, d), 8.59(1H, brt), 8.94(1H, brs). |
| 32 | 1-isobutyl-1H-indol-5-yl | 424(M+H)⁺ 422(M−H)⁻ | (DMSO-d₆)δ(ppm): 0.84(6H, d), 1.35(6H, s), 1.98-2.29(5H, m), 3.54-3.65(6H, m), 3.71-3.74(1H, m), 4.02(2H, d), 4.07-4.19(2H, m), 4.84-4.86(1H, m), 6.56(1H, d), 7.44(1H, d), 7.55(1H, d), 7.73(1H, dd), 8.22(1H, s), 8.59(1H, brt), 8.96(1H, brs). |
| 33 | 1-benzyloxymethyl-1H-indol-3-yl | 488(M+H)⁺ 486(M−H)⁻ | (DMSO-d₆)δ(ppm): 1.33, 1.34(6H, 2s), 1.95-2.15(2H, m), 2.15-2.30(2H, m), 3.50-3.60(3H, m), 3.70-3.80(1H, m), 4.05-4.25(2H, m), 4.50(2H, s), 4.87(1H, m), 5.74(2H, s), 7.15-7.40(7H, m), 7.65(1H, d), 8.17(1H, d), 8.33(1H, s), 8.40(1H, brt), 8.93(2H, brs). |
| 34 | 1-methoxymethyl-1H-indol-3-yl | 412(M+H)⁺ 410(M−H)⁻ | (DMSO-d₆)δ(ppm): 1.04, 1.05(6H, 2s), 1.95-2.10(2H, m), 2.10-2.20(2H, m), 3.15-3.35(3H, m), 3.35-3.50(2H, m), 3.60-3.70(1H, m), 4.74(1H, m), 5.57(2H, s), 7.15-7.25(2H, m), 7.60(1H, d), 7.79(1H, brt), 8.13(1H, d). |
| 35 | 1-acetoxymethyl-1H-indol-3-yl | 440(M+H)⁺ 438(M−H)⁻ | (DMSO-d₆)δ(ppm): 1.04(6H, s), 1.95-2.10(2H, m), 2.04(3H, m), 2.10-2.20(2H, m), 3.15-3.30(2H, m), 3.35-3.50(3H, m), 3.60-3.70(1H, m), 4.74(1H, m), 6.20(2H, s), 7.20(1H, t), 7.27(1H, t), 7.63(1H, d), 7.85(1H, brt), 8.13(1H, d), 8.19(1H, s). |
| 36 | 1-benzyloxymethyl-1H-indol-5-yl | 488(M+H)⁺ 486(M−H)⁻ | (DMSO-d₆)δ(ppm): 1.05(6H, s), 1.95-2.06(2H, m), 2.11-2.21(2H, m), 3.20-3.30(2H, m), 3.36-3.56(3H, m), 3.60-3.70(1H, m), 4.45(2H, s), 4.74-4.77(1H, m), 5.71(2H, s). |

TABLE 15

| Example | A | ESI/MS(m/z) | ¹H NMR |
|---|---|---|---|
| 37 | hydroxymethyl-1H-indol-5-yl | 398(M+H)⁺ | (DMSO-d₆)δ(ppm): 1.03, 1.04(6H, 2s), 1.95-2.20(4H, m), 3.20-3.30(2H, m), 3.40-3.60(3H, m), 3.60-3.70(1H, m), 4.75(1H, q), 5.53(2H, d), 6.51(1H, t), 6.55(1H, d), 7.48(1H, d), 7.59(1H, d), 7.70(1H, dd), 8.10-8.20(1H, m), 8.13(1H, d). |

TABLE 15-continued

| Example | A | ESI/MS(m/z) | ¹H NMR |
|---|---|---|---|
| 38 | methoxymethyl-1H-indol-5-yl | 412(M+H)+ 410(M−H)− | (DMSO-$d_6$)δ(ppm): 1.03, 1.04(6H, 2s), 1.95-2.20(4H, m), 3.15(3H, s), 3.20-3.30(2H, m), 3.30-3.50(4H, m), 3.60-3.70(1H, m), 4.75(1H, q), 5.56(2H, s), 6.61(1H, d), 7.57(1H, d), 7.61(1H, d), 7.70(1H, dd), 8.14(1H, d), 8.20-8.30(1H, m). |
| 39 | 1-(2,2-dimethyl-propyl)-5-methoxy-1H-indol-3-yl | 468(M+H)+ 466(M−H)− | (DMSO-$d_6$)δ(ppm): 0.95(9H, s), 1.33(6H, s), 1.95-2.15(2H, m), 2.15-2.25(2H, m), 3.50-3.60(3H, m), 3.70-3.80(1H, m), 3.77(3H, s), 3.99(2H, s), 4.05-4.25(2H, m), 4.87(1H, m), 6.83(1H, dd), 7.51(1H, d), 7.67(1H, d), 8.07(1H, s), 8.33(1H, brt), 8.88(2H, brs). |
| 40 | 1-(2,2-dimethyl-propyl)-5-methyl-1H-indol-3-yl | 452(M+H)+ 450(M−H)− | (DMSO-$d_6$)δ(ppm): 0.95(9H, s), 1.32, 1.33(6H, 2s), 2.00-2.15(2H, m), 2.15-2.25(2H, m), 2.39(3H, s), 3.50-3.60(3H, m), 3.70-3.80(1H, m), 4.00(2H, s), 4.05-4.25(2H m), 4.87(1H, m), 7.02(1H, d), 7.48(1H, d), 7.94(1H, s), 8.07(1H, s), 8.26(1H, brt), 8.92(2H, brs) |
| 41 | 1-(2,2-dimethyl-propyl)-5-hydroxy-1H-indol-3-yl | 454(M+H)+ 452(M−H)− | (DMSO-$d_6$)δ(ppm): 0.94(9H, s), 1.31, 1.32(6H, 2s), 1.95-2.15(2H, m), 2.15-2.25(2H, m), 3.45-3.60(3H, m), 3.65-3.75(1H, m), 3.94(2H, s), 4.00-4.20(2H, m), 4.86(1H, m), 6.68(1H, dd), 7.37(1H, d), 7.52(1H, d), 8.00(1H, s), 8.16(1H, brt), 8.93(2H, brs). |
| 42 | 1-(2,2-dimethyl-propionyloxy-methyl)-1H-indol-3-yl | 482(M+H)+ | (DMSO-$d_6$)δ(ppm): 1.10(6H, s), 1.16(9H, s), 2.10-2.30(4H, m), 3.30-3.50(5H, m), 3.70-3.80(1H, m), 4.79-4.81(1H, m), 6.30(2H, s), 7.24-7.34(2H, m), 7.66-7.67(1H, m), 7.84(1H, brs), 8.19-8.21(1H, m), 8.24(1H, s). |
| 43 | 1-t-butoxy-carbonylmethyl-1H-indol-5-yl | 482(M+H)+ | (DMSO-$d_6$)δ(ppm): 1.10(6H, s), 1.43(9H, s), 2.00-2.20(4H, m), 3.20-3.30(2H, m), 3.40-3.50(3H, m), 3.60 3.70(1H, m), 5.00(2H, s), 6.57(1H, d), 7.40(2H, m), 7.67(1H, dd), 8.06(1H, brs), 8.13(1H, d). |
| 44 | methyl-2,3-dihydro-1H-indol-5-yl | 384(M+H)+ 382(M−H)− | (DMSO-$d_6$)δ(ppm): 1.29(6H, s), 1.95-2.15(2H, m), 2.15-2.30(2H, m), 2.77(3H, s), 2.93(2H, t), 3.38(2H, t), 3.45-3.60(3H, m), 3.70-3.80(1H, m), 4.00-4.20(2H, m), 4.86(1H, m), 6.50(1H, d), 7.61(1H, s), 7.66(1H, d), 8.35(1H, brt), 8.83(2H, brs). |

TABLE 16

| Example | A | ESI/MS(m/z) | ¹H NMR |
|---|---|---|---|
| 45 | 1-acetyl-1H-indol-3-yl | 410(M+H)+ 408(M−H)− | (DMSO-$d_6$)δ(ppm): 1.36(6H, s), 2.00-2.30(4H, m), 2.72(3H, s), 3.50-3.70(3H, m), 3.70-3.85(1H, m), 4.10-4.30(2H, m), 4.88(1H, m), 7.30-7.50(2H, m), 8.19(1H, d), 8.34(1H, m), 8.70-8.80(1H, m), 8.80(1H, s), 8.95(2H, brs). |
| 46 | 1-acetyl-2,3-di-hydro-1H-indol-5-yl | 412(M+H)+ 410(M−H)− | (DMSO-$d_6$)δ(ppm): 1.31(6h, s), 2.00-2.30(4H, m), 2.19(3H, s), 3.19(2H, t), 3.50-3.60(3H, m), 3.65-3.75(1H, m), 4.05-4.20(2H, m), 4.15(2H, t), 4.86(1H, q), 7.75(1H, d), 7.78(1H, s), 8.07(1H, d), 8.58(1H, t), 8.75-9.00(2H, m). |
| 47 | 1-acetyl-1H-indol-5-yl | 410(M+H)+ 408(M−H)− | (DMSO-$d_6$)δ(ppm): 1.35(6H, s), 2.00-2.15(2H, m), 2.15-2.30(2H, m), 2.68(3H, s), 3.50-3.65(3H, m), 3.70-3.80(1H, m), 4.05-4.30(2H, m), 4.87(1H, m), 6.87(1H, d), 7.89(1H, d), 7.97(1H, d), 8.23(1H, s), 8.39(1H, d), 8.77(1H, brs), 8.91(2H, brs). |
| 48 | 1-benzoyl-1H-indol-5-yl | 472(M+H)+ 470(M−H)− | (DMSO-$d_6$)δ(ppm): 1.10(6H, m), 2.00-2.20(4H, m), 3.20-3.50(5H, m), 3.60-3.70(1H, m), 4.75-4.76(1H, m), 6.86(1H, d), 7.47-7.53(2H, m), 7.61-7.64(2H, m), 7.70-7.74(1H, m), 7.78(1H, d), 7.84-7.90(2H, m), 8.21(1H, brs), 8.28(1H, d). |
| 49 | 1-(2,2-dimethyl-propionyl)-1H-indol-5-yl | 452(M+H)+ | (DMSO-$d_6$)δ(ppm): 1.10(6H, s), 1.50(9H, s), 2.00-2.20(4H, m), 3.20-3.50(5H, m), 3.60-3.70(1H, m), 4.75-7.77(1H, m), 6.84(1H, d), 7.84(1H, dd), 8.15(1H, brs), 8.18(1H, d), 8.20(1H, brs), 8.40(1H, d). |

TABLE 16-continued

| Example | A | ESI/MS(m/z) | ¹H NMR |
|---|---|---|---|
| 50 | 1-(2,2,2-tri-fluoroacetyl)-2,3-dihydro-1H-indol-5-yl | 466(M+H)⁺ 464(M–H)⁻ | (DMSO-d₆)δ(ppm): 1.05(6H, s), 2.00-2.20(4H, m), 3.30-3.50(7H, m), 3.60-3.70(1H, m), 4.36(2H, t), 4.76-4.77(1H, m), 7.83(1H, d), 7.87(1H, brs), 8.11(1H, d), 8.21(1H, t). |
| 51 | benzothiazol-6-yl | 386(M+H)⁺ 384(M–H)⁻ | (DMSO-d₆)δ(ppm): 1.37(6H, s), 2.08-2.26(4H, m), 3.36-3.38(2H, m), 3.71-3.73(2H, m), 4.12-4.18(2H, m), 4.84(1H, dd), 8.09(1H, dd), 8.19(1H, d), 8.76(1H, s), 8.93(2H, brs), 9.55(1H, s). |
| 52 | 4-methoxy-2-methylbenzothiazol-6-yl | 430(M+H)⁺ 428(M–H)⁻ | (DMSO-d₆)δ(ppm): 1.35(6H, s), 1.90-2.24(4H, m), 2.81(3H, s), 3.49-3.60(4H, m), 4.01(3H, s), 4.09-4.18(2H, m), 4.87(1H, dd), 7.54(1H, d), 8.19(1H, d), 8.90(1H, t), 8.93(2H, brs). |

TABLE 17

| Example | A | ESI/MS(m/z) | ¹H NMR |
|---|---|---|---|
| 53 | 4-methoxy-2-trifluoromethylbenzothiazol-6-yl | 484(M+H)⁺ 482(M–H)⁻ | (DMSO-d₆)δ(ppm): 1.37(6H, s), 2.02-2.32(4H, m), 3.37-3.58(3H, m), 3.61(2H, d), 3.66-3.77(1H, m), 4.09(3H, s), 4.14-4.27(2H, m), 4.87(1H, d), 7.72(1H, s), 8.44(1H, s), 8.96(2H, brs), 9.09(1H, t). |
| 54 | 4-methoxy-2-phenylbenzothiazol-6-yl | 492(M+H)⁺ 490(M–H)⁻ | (DMSO-d₆)δ(ppm): 1.38(6H, s), 2.01-2.26(4H, m), 3.50-3.58(3H, m), 3.62(2H, d), 3.74-3.79(1H, m), 4.09(3H, s), 4.12-4.26(2H, m), 4.87(1H, dd), 7.60(3H, m), 7.64(1H, d), 8.11(2H, m), 8.33(1H, d), 9.02(2H, brs), 9.05(1H, t). |
| 55 | 2-oxo-2,3-dihydro-benzothiazol-6-yl | 402(M+H)⁺ 400(M–H)⁻ | (DMSO-d₆)δ(ppm): 1.18(6H, s), 2.18-2.35(4H, m), 3.35(2H, d), 3.41-3.51(1H, m), 3.46(2H, d), 3.62-3.69(1H, m), 4.77(1H, dd), 7.08(1H, d), 7.37(1H, t), 7.71(1H, dd), 7.92(1H, d). |
| 56 | 1-methyl-1H-benz-imidazol-5-yl | 383(M+H)⁺ 381(M–H)⁻ | (DMSO-d₆)δ(ppm): 1.36(6H, s), 1.95-2.30(4H, m), 3.50-3.65(2H, m), 3.65-3.75(2H, m), 4.03(3H, s), 4.05-4.25(2H, m), 4.87(1H, q), 7.96(1H, d), 8.09(1H, d), 8.42(1H, s), 8.85-9.10(2H, brs), 9.34(1H, brs). |
| 57 | 2-methylbenz-oxazol-6-yl | 384(M+H)⁺ 382(M–H)⁻ | (DMSO-d₆)δ(ppm): 1.34(6H, s), 1.95-2.30(4H, m), 2.66(3H, s), 3.30-3.60(5H, m), 3.65·.75(1H, m), 4.00-4.20(1H, m), 4.86(1H, q), 7.76(1H, d), 7.92(1H, dd), 8.19(1H, d), 8.74(1H, t), 8.75-8.90(1H, m). |
| 58 | isoquinolin-3-yl | 380(M+H)⁺ 378(M–H)⁻ | (DMSO-d₆)δ(ppm): 1.37(6H, s), 2.08-2.23(4H, m), 3.30-3.80(4H, m), 4.10-4.80(2H, m), 4.86-4.87(1H, m), 7.85(1H, dd), 7.92(1H, dd), 8.30(1H, d), 8.23(1H, d), 8.65(1H, s), 9.00(2H, m), 9.30(1H, m), 9.46(1H, s). |
| 59 | indan-2-yl | 369(M+H)⁺ 367(M–H)⁻ | (DMSO-d₆)δ(ppm): 1.27(6H, s), 1.95-2.25(4H, m), 3.00-3.20(4H, m), 3.26(1H, q), 3.30-3.45(2H, m), 3.52(1H, q), 3.65-3.75(1H, m), 4.00-4.20(2H, m), 4.86(1H, q), 7.10-7.25(4H, m), 8.33(1H, brs), 8.90(2H, brs). |

EXAMPLE 60

(S)-2-Methylpyrazolo[1,5-a]pyrimidine-6-carboxylic acid {2-[2(2-cyanopyrrolidin-1-yl)-2-oxoethylamino]-2-methylpropyl}methylamide In a similar procedure as employed in the Example 1, the title compound (210 mg, Y.:28%) was obtained from 2-methylpyrazolo[1,5-a]pyrimidine-6-carboxylic acid (354 mg) and (S)-1-[2-(1,1-dimethyl-2-methylaminoethylamino)acetyl]pyrrolidine-2-carbonitrile (450 mg).

¹HNMR; (DMSO-d₆) δ (ppm):1.36 (6H, s), 1.98 (1H, brs),2.00-2.30 (4H, m), 2.50 (3H, s), 2.90 (3H, s), 3.30-3.80 (4H, m), 4.10-4.30 (2H, m), 4.80 (1H, m), 6.63 (1H, s), 8.80 (1H, s), 9.50 (1H, s).

ESI/MS (m/z):398 (M+H)⁺, 396 (M–H)⁻.

EXAMPLE 61

(S)-1-{2-[3-(1,3-Dihydroisoindol-2-yl)-1,1-dimethyl-3-oxopropylamino]acetyl}pyrrolidine-2-carbonitrile Potassium carbonate (370 mg) and sodium iodide (200 mg) were added to a solution of 3-amino-1-(1,3-dihydroisoindol-2-yl)-3-methylbutan-1-one (0.55 g) in acetone.

(S)-1-(2'-Chloroacetyl)pyrrolidine-2-carbonitrile (467 mg) was added thereto with ice cooling, and the mixture was stirred for 8 hours at room temperature. Dichloromethane was added thereto, then insoluble matter was removed by filtration, and the filtrate was concentrated under reduced pressure. The residue was purified by column chromatography (eluting solvent; dichloromethane:methanol 20:1) to give the title compound (0.54 g, 61%).

$^1$H NMR; (DMSO-d$_6$) δ (ppm):1.39, 1.40 (6H, 2s), 2.00-2.25 (4H, m), 2.85-2.95 (2H, m), 3.30-4.10 (4H, m), 4.71, 4.90 (4H, 2s), 4.85-4.90 (1H, m), 7.30-7.40 (4H, m).

ESI/MS (m/z):355 (M+H)$^+$.

In a similar procedure as employed in the Example 61, compounds were synthesized according to the following reaction scheme. The synthesized compounds and data are shown in Tables 18 to 22. (Each symbol has the same meaning as defined above.)

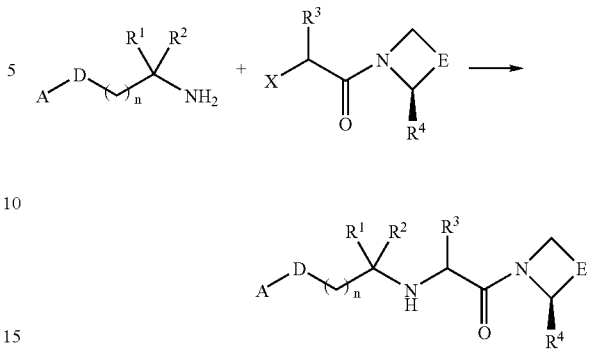

TABLE 18

| Example | A | D | n | R1 | R2 | R$^3$ | R$^4$ | E | ESI/MS (m/z) |
|---|---|---|---|---|---|---|---|---|---|
| 62 | 5-methyl-1,3-dihydroisoindol-2-yl | —CO— | 1 | Me | Me | H | CN | —CH$_2$CH$_2$— | 369 (M + H)$^+$ |
| 63 | 5-fluoro-1,3-dihydroisoindol-2-yl | —CO— | 1 | Me | Me | H | CN | —CH$_2$CH$_2$— | 373 (M + H)$^+$ |
| 64 | 5-bromo-1,3-dihydroisoindol-2-yl | —CO— | 1 | Me | Me | H | CN | —CH$_2$CH$_2$— | 435 (M + H)$^+$ 433 (M − H)$^-$ |
| 65 | 5-chloro-1,3-dihydroisoindol-2-yl | —CO— | 1 | Me | Me | H | CN | —CH$_2$CH$_2$— | 391 (M + H)$^+$ 389 (M − H)$^-$ |
| 66 | 5-t-butyl-1,3-dihydroisoindol-2-yl | —CO— | 1 | Me | Me | H | CN | —CH$_2$CH$_2$— | 411 (M + H)$^+$ |
| 67 | 4-fluoro-1,3-dihydroisoindol-2-yl | —CO— | 1 | Me | Me | H | CN | —CH$_2$CH$_2$— | 373 (M + H)$^+$ 371 (M − H)$^-$ |
| 68 | 4-methyl-1,3-dihydroisoindol-2-yl | —CO— | 1 | Me | Me | H | CN | —CH$_2$CH$_2$— | 369 (M + H)$^+$ 367 (M − H)$^-$ |
| 69 | 4,7-dichloro-1,3-dihydroisoindol-2-yl | —CO— | 1 | Me | Me | H | CN | —CH$_2$CH$_2$— | 423 (M + H)$^+$ |
| 70 | 4-hydroxy-1,3-dihydroisoindol-2-yl | —CO— | 1 | Me | Me | H | CN | —CH$_2$CH$_2$— | 371 (M + H)$^+$ 369 (M − H)$^-$ |
| 71 | 5-hydroxymethyl-1,3-dihydroisoindol-2-yl | —CO— | 1 | Me | Me | H | CN | —CH$_2$CH$_2$— | 385 (M + H)$^+$ |
| 72 | 5-trifluoromethyl-1,3-dihydroisoindol-2-yl | —CO— | 1 | Me | Me | H | CN | —CH$_2$CH$_2$— | 423 (M + H)$^+$ 421 (M − H)$^-$ |
| 73 | 4,5,6,7-tetrachloro-1,3-dihydroisoindol-2-yl | —CO— | 1 | Me | Me | H | CN | —CH$_2$CH$_2$— | 491 (M + H)$^+$ |
| 74 | 5,6-dichloro-1,3-dihydroisoindol-2-yl | —CO— | 1 | Me | Me | H | CN | —CH$_2$CH$_2$— | 423 (M + H)$^+$ |
| 75 | 4-hydroxy-6-methyl-1,3-dihydroisoindol-2-yl | —CO— | 1 | Me | Me | H | CN | —CH$_2$CH$_2$— | 385 (M + H)$^+$ |
| 76 | 4-methoxy-6-methyl-1,3-dihydroisoindol-2-yl | —CO— | 1 | Me | Me | H | CN | —CH$_2$CH$_2$— | 399 (M + H)$^+$ |
| 77 | 5-methoxy-1,3-dihydroisoindol-2-yl | —CO— | 1 | Me | Me | H | CN | —CH$_2$CH$_2$— | 385 (M + H)$^+$ |
| 78 | 4-methoxy-1,3-dihydroisoindol-2-yl | —CO— | 1 | Me | Me | H | CN | —CH$_2$CH$_2$— | 385 (M + H)$^+$ |

TABLE 19

| Example | A | D | n | R1 | R2 | R$^3$ | R$^4$ | E | ESI/MS (m/z) |
|---|---|---|---|---|---|---|---|---|---|
| 79 | 3,4-dihydro-1H-isoquinolin-2-yl | —CO— | 1 | Me | Me | H | CN | —CH$_2$CH$_2$— | 369 (M + H)$^+$ 367 (M − H)$^-$ |
| 80 | 1,3-dihydroisoindol-2-yl | —CO— | 0 | Me | Me | H | CN | —CH$_2$CH$_2$— | 341 (M + H)$^+$ |
| 81 | 1,3,4,5-tetrahydrobenzo[c]azepin-2-yl | —CO— | 0 | Me | Me | H | CN | —CH$_2$CH$_2$— | 369 (M + H)$^+$ 367 (M − H)$^-$ |
| 82 | 1,3-dihydroisoindol-2-yl- | —CO— | 2 | Me | Me | H | CN | —CH$_2$CH$_2$— | 369 (M + H)$^+$ 367 (M − H)$^-$ |
| 83 | 2-methylpyrazolo[1,5-a]pyrimidin-6-yl | —CONH— | 1 | Me | Me | H | (R) CN | —CH$_2$CH$_2$— | 384 (M + H)$^+$ 382 (M − H)$^-$ |
| 84 | 2-methylpyrazolo[1,5-a]pyrimidin-6-yl | —CONH— | 1 | Me | Me | H | CN | —SCH$_2$— | 402 (M + H)$^+$ 400 (M − H)$^-$ |
| 85 | 2-methylpyrazolo[1,5-a]pyrimidin-6-yl | —CONH— | 1 | Me | Me | H | CN | —CH$_2$— | 370 (M + H)$^+$ 368 (M − H)$^-$ |

TABLE 19-continued

| Example | A | D | n | R1 | R2 | R³ | R⁴ | E | ESI/MS (m/z) |
|---|---|---|---|---|---|---|---|---|---|
| 86 | 2-methylpyrazolo[1,5-a]pyrimidin-6-yl | —CONH— | 1 | cyclopentyl | H | H | CN | —CH₂CH₂— | 410 (M + H)⁺<br>408 (M − H)⁻ |
| 87 | 2-methylpyrazolo[1,5-a]pyrimidin-6-yl | —CONH— | 3 | Me | Me | H | CN | —CH₂CH₂— | 412 (M + H)⁺<br>410 (M − H)⁻ |
| 88 | benzothiazol-6-yl | —CONH— | 1 | H | —COOMe | H | CN | —CH₂CH₂— | 416 (M + H)⁺<br>414 (M − H)⁻ |
| 89 | 1,3-dihydroisoindol-2-yl | —CO— | 1 | H | H | H | CN | —CH₂CH₂— | 327 (M + H)⁺ |
| 90 | 3,4-dihydro-1H-isoquinolin-2-yl | —CO— | 1 | H | H | H | CN | —CH₂CH₂— | 341 (M + H)⁺ |
| 91 | 2,3-dihydroindol-1-yl | —CO— | 1 | H | H | H | CN | —CH₂CH₂— | 327 (M + H)⁺<br>325 (M − H)⁻ |
| 94 | indol-1-yl | —CO— | 1 | H | H | H | CN | —CH₂CH₂— | 325 (M + H)⁺<br>323 (M − H)⁻ |
| 92 | 1,3-dihydroisoindol-2-yl | —CO— | 2 | H | H | H | CN | —CH₂CH₂— | 341 (M + H)⁺ |
| 93 | benzothiazol-2-yl | —NHCO— | 1 | H | H | H | CN | —CH₂CH₂— | 358 (M + H)⁺<br>356 (M − H)⁻ |
| 95 | benzothiazol-6-yl | —CONH— | 1 | H | H | H | CN | —CH₂CH₂— | 358 (M + H)⁺ |
| 96 | benzothiazol-6-yl | —CONH— | 1 | H | H | Ph | CN | —CH₂CH₂— | 435 (M + H)⁺ |
| 97 | benzothiazol-6-yl | —CONH— | 1 | H | H | H | H | —SCH₂— | 351 (M + H)⁺ |

TABLE 20

| Example | A | D | n | R1 | R2 | R³ | R⁴ | E | ESI/MS (m/z) |
|---|---|---|---|---|---|---|---|---|---|
| 98 | benzothiazol-6-yl | —CONH— | 1 | H | H | H | H | —CH₂CH₂— | 333 (M + H)⁺ |
| 99 | benzothiazol-6-yl | —CONH— | 1 | H | H | H | CN | —CH₂CH₂CH₂— | 372 (M + H)⁺ |
| 100 | benzothiazol-6-yl | —CONH— | 1 | H | H | H | H | —CH₂OCH₂— | 349 (M + H)⁺ |
| 101 | 2-methylbenzothiazol-6-yl | —CONH— | 1 | H | H | H | CN | —CH₂CH₂— | 372 (M + H)⁺ |
| 102 | 5-methoxybenzothiazol-6-yl | —CONH— | 1 | H | H | H | CN | —CH₂CH₂— | 388 (M + H)⁺<br>386 (M − H)⁻ |
| 103 | 4-methoxybenzothiazol-6-yl | —CONH— | 1 | H | H | H | CN | —CH₂CH₂— | 388 (M + H)⁺ |
| 104 | 2-phenylbenzothiazol-6-yl | —CONH— | 1 | H | H | H | CN | —CH₂CH₂— | 435 (M + H)⁺ |
| 105 | benzothiazol-6-yl | —CONH— | 3 | H | H | H | CN | —CH₂CH₂— | 386 (M + H)⁺ |
| 106 | 1-methyl-1H-indol-2-yl | —CONH— | 1 | H | H | H | CN | —CH₂CH₂— | 354 (M + H)⁺ |
| 107 | isoquinolin-3-yl | —CONH— | 1 | H | H | H | CN | —CH₂CH₂— | 352 (M + H)⁺ |
| 108 | isoquinolin-3-yl | —CONH— | 1 | H | H | H | H | —SCH₂— | 345 (M + H)⁺ |
| 109 | isoquinolin-3-yl | —CONH— | 1 | H | H | H | H | —CH₂CH₂— | 327 (M + H)⁺ |
| 110 | isoquinolin-3-yl | —CONH— | 1 | H | H | H | CN | —CH₂CH₂CH₂— | 366 (M + H)⁺ |
| 111 | isoquinolin-3-yl | —CONH— | 1 | H | H | H | H | —CH₂OCH₂— | 343 (M + H)⁺ |
| 112 | isoquinolin-1-yl | —CONH— | 1 | H | H | H | CN | —CH₂CH₂— | 352 (M + H)⁺ |
| 113 | isoquinolin-1-yl | —CONH— | 1 | H | H | H | H | —SCH₂— | 345 (M + H)⁺ |
| 114 | isoquinolin-1-yl | —CONH— | 1 | H | H | H | H | —CH₂CH₂— | 327 (M + H)⁺ |
| 115 | isoquinolin-1-yl | —CONH— | 1 | H | H | H | H | —CH₂OCH₂— | 343 (M + H)⁺ |
| 116 | quinolin-3-yl | —CONH— | 1 | H | H | H | CN | —CH₂CH₂— | 352 (M + H)⁺ |

TABLE 21

| Example | A | D | n | R1 | R2 | R³ | R⁴ | E | ESI/MS (m/z) |
|---|---|---|---|---|---|---|---|---|---|
| 117 | quinolin-3-yl | —CONH— | 1 | H | H | H | H | —SCH₂— | 345 (M + H)⁺ |
| 118 | quinolin-3-yl | —CONH— | 1 | H | H | H | H | —CH₂CH₂— | 327 (M + H)⁺ |
| 119 | quinolin-3-yl | —CONH— | 1 | H | H | H | CN | —CH₂CH₂CH₂— | 366 (M + H)⁺ |
| 120 | quinolin-3-yl | —CONH— | 1 | H | H | H | H | —CH₂OCH₂— | 343 (M + H)⁺ |
| 121 | quinolin-2-yl | —CONH— | 1 | H | H | H | CN | —CH₂CH₂— | 352 (M + H)⁺ |
| 122 | 1,3-dimethyl-1H-pyrazolo[3,4-b]pyridin-5-yl | —CONH— | 1 | H | H | H | CN | —CH₂CH₂— | 370 (M + H)⁺ |
| 123 | 1,3-dimethyl-1H-pyrazolo[3,4-b]pyridin-5-yl | —CONH— | 1 | H | H | H | H | —SCH₂— | 363 (M + H)⁺ |
| 124 | 1,3-dimethyl-1H-pyrazolo[3,4-b]pyridin-5-yl | —CONH— | 1 | H | H | H | H | —CH₂CH₂— | 345 (M + H)⁺ |
| 125 | 1,3-dimethyl-1H-pyrazolo[3,4-b]pyridin-5-yl | —CONH— | 1 | H | H | H | H | —CH₂OCH₂— | 361 (M + H)⁺ |
| 126 | 5-oxo-2,3-dihydro-5H-thiazolo[3,2-a]pyrimidin-6-yl | —CONH— | 1 | H | H | H | CN | —CH₂CH₂— | 377 (M + H)⁺ |
| 127 | 5-oxo-2,3-dihydro-5H-thiazolo[3,2-a]pyrimidin-6-yl | —CONH— | 1 | H | H | H | H | —SCH₂— | 370 (M + H)⁺ |
| 128 | 5-oxo-2,3-dihydro-5H-thiazolo[3,2-a]pyrimidin-6-yl | —CONH— | 1 | H | H | H | H | —CH₂CH₂— | 352 (M + H)⁺ |
| 129 | 5-oxo-2,3-dihydro-5H-thiazolo[3,2-a]pyrimidin-6-yl | —CONH— | 1 | H | H | H | CN | —CH₂CH₂CH₂— | 391 (M + H)⁺ |
| 130 | 5-oxo-2,3-dihydro-5H-thiazolo[3,2-a]pyrimidin-6-yl | —CONH— | 1 | H | H | H | H | —CH₂OCH₂— | 368 (M + H)⁺ |

TABLE 21-continued

| Example | A | D | n | R1 | R2 | R³ | R⁴ | E | ESI/MS (m/z) |
|---|---|---|---|---|---|---|---|---|---|
| 131 | 2,7-dimethylpyrazolo[1,5-a]-pyrimidin-6-yl | —CONH— | 1 | H | H | H | CN | —$CH_2CH_2$— | 370 (M + H)⁺ |
| 132 | 2,7-dimethylpyrazolo[1,5-a]-pyrimidin-6-yl | —CONH— | 1 | H | H | H | H | —$SCH_2$— | 363 (M + H)⁺ |
| 133 | 2,3-dihydrobenzo[1,4]dioxan-6-yl | —CONH— | 1 | H | H | H | CN | —$CH_2CH_2$— | 359 (M + H)⁺ |
| 134 | 2,3-dihydrobenzo[1,4]dioxan-6-yl | —CONH— | 1 | H | H | H | H | —$SCH_2$— | 352 (M + H)⁺ |
| 135 | 2-methylimidazo[1,2-a]-pyridin-3-yl | —CONH— | 1 | H | H | H | CN | —$CH_2CH_2$— | 355 (M + H)⁺ |

TABLE 22

| Example | A | D | n | R1 | R2 | R³ | R⁴ | E | ESI/MS (m/z) |
|---|---|---|---|---|---|---|---|---|---|
| 136 | 2-methylimidazo[1,2-a]-pyridin-3-yl | —CONH— | 1 | H | H | H | H | —$SCH_2$— | 348 (M + H)⁺ |
| 137 | 2-methylimidazo[1,2-a]-pyridin-3-yl | —CONH— | 1 | H | H | H | H | —$CH_2CH_2$— | 330 (M + H)⁺ |
| 138 | 2-methylimidazo[1,2-a]-pyridin-3-yl | —CONH— | 1 | H | H | H | H | —$CH_2OCH_2$— | 346 (M + H)⁺ |
| 139 | 8-ethyl-5-oxo-2-pyrrolidin-1-yl-5,8-dihydropyrido[2,3-d]-pyrimidin-6-yl | —CONH— | 1 | H | H | H | CN | —$CH_2CH_2$— | 468 (M + H)⁺ |
| 140 | 8-ethyl-5-oxo-2-pyrrolidin-1-yl-5,8-dihydropyrido[2,3-d]-pyrimidin-6-yl | —CONH— | 1 | H | H | H | H | —$SCH_2$— | 461 (M + H)⁺ |
| 141 | 8-ethyl-5-oxo-2-pyrrolidin-1-yl-5,8-dihydropyrido[2,3-d]-pyrimidin-6-yl | —CONH— | 1 | H | H | H | CN | —$CH_2CH_2CH_2$— | 482 (M + H)⁺ |

EXAMPLE 142

(S)-1-{2-[2-(1,3-Dihydroisoindol-2-yl)-2-oxoethylamino]acetyl}pyrrolidine-2-carbonitrile {t-Butoxycarbonyl-[2-(1,3-dihydroisoindol-2-yl)-2-oxoethyl]amino}acetic acid (260 mg), N-(3-dimethylaminopropyl)-N'-ethylcarbodiimide hydrochloride (150 mg) and hydroxybenzotriazole (120 mg) were dissolved in N,N-dimethylformamide (5.0 ml). Triethylamine (110 µl) and (S)-pyrrolidine-2-carbonitrile hydrochloride (100 mg) were added thereto, and the mixture was stirred for 21 hours at room temperature. The reaction mixture was concentrated under reduced pressure, then ethyl acetate and 10% citric acid solution were added to the residue, and the organic phase was separated. The organic phase was washed with 4% sodium bicarbonate solution and a saturated saline solution and dried over sodium sulfate anhydrous. The reaction mixture was concentrated under reduced pressure, and the residue was purified by column chromatography (eluting solvent; dichloromethane:methanol 20:1) to give t-butyl (S)-[2-(cyanopyrrolidin-1-yl)-2-oxoethyl]-[2-(1,3-dihydrois oindol-2-yl)-2-oxoethyl]carbamate (290 mg, Y.:90%).

ESI/MS (m/z):413 (M+H)⁺, 411 (M–H)⁻.

The t-butyl (S)-[2-(cyanopyrrolidin-1-yl)-2-oxoethyl]-[2-(1,3-dihydrois oindol-2-yl)-2-oxoethyl]carbamate (280 mg) obtained above was dissolved in 1,4-dioxane (1.0 ml), and 4 N Hydrochloric acid/1,4-dioxane (1.0 ml) was added thereto and stirred for 30 minutes with ice cooling. Ether was added thereto, and precipitated crystals were collected by filtration and dried under reduced pressure to give a hydrochloride (240 mg, Y.: quant.) of the title compound.

¹H NMR; (DMSO-d₆) δ (ppm):2.03-2.19 (4H, m), 3.36-3.44 (2H, m), 3.57, 4.10 (4H, 2s), 4.74, 4.84 (4H, 2s), 4.86-4.88 (1H, m), 7.32-7.39 (4H, m).

ESI/MS (m/z):313 (M+H)⁺, 311 (M–H)⁻.

In a similar procedure as employed in the Example 142, compounds were synthesized according to the following reaction scheme. The synthesized compounds and data are shown in Tables 23 to 27.

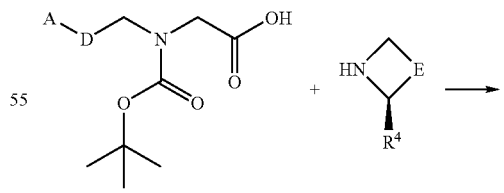

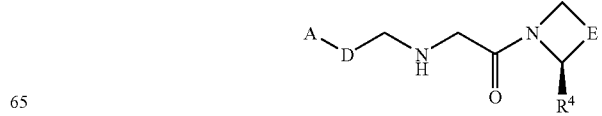

TABLE 23

| Example | A | D | R⁴ | E | ESI/MS (m/z) |
|---|---|---|---|---|---|
| 143 | 1,3-dihydroisoindol-2-yl | —CO— | H | —SCH₂— | 306 (M + H)⁺ |
| 144 | 1,3-dihydroisoindol-2-yl | —CO— | H | —CH₂CH₂— | 288 (M + H)⁺ |
| 145 | 1,3-dihydroisoindol-2-yl | —CO— | (±)CN | —CH₂CH₂CH₂— | 327 (M + H)⁺ |

TABLE 24

| Example | A | D | R⁴ | E | ESI/MS (m/z) |
|---|---|---|---|---|---|
| 146 | 1,3-dihydroisoindol-2-yl | —CO— | H | —CH₂OCH₂— | 304 (M + H)⁺ |
| 147 | 1,3-dihydroisoindol-2-yl | —CO— | H | —CH₂CH₂CH₂— | 302 (M + H)⁺ |
| 148 | 2,3-dihydroindol-1-yl | —CO— | CN | —CH₂CH₂— | 313 (M + H)⁺ |
| 149 | 2,3-dihydroindol-1-yl | —CO— | H | —SCH₂— | 306 (M + H)⁺ |
| 150 | 2,3-dihydroindol-1-yl | —CO— | H | —CH₂CH₂— | 288 (M + H)⁺ |
| 151 | 2,3-dihydroindol-1-yl | —CO— | (±)CN | —CH₂CH₂CH₂— | 327 (M + H)⁺ |
| 152 | 2,3-dihydroindol-1-yl | —CO— | H | —CH₂OCH₂— | 304 (M + H)⁺ |
| 153 | 2,3-dihydroindol-1-yl | —CO— | H | —CH₂CH₂CH₂— | 302 (M + H)⁺ |
| 154 | 3,4-dihydro-1H-isoquinolin-2-yl | —CO— | CN | —CH₂CH₂— | 327 (M + H)⁺ |
| 155 | 3,4-dihydro-1H-isoquinolin-2-yl | —CO— | H | —SCH₂— | 320 (M + H)⁺ |
| 156 | 3,4-dihydro-1H-isoquinolin-2-yl | —CO— | H | —CH₂CH₂— | 302 (M + H)⁺ |
| 157 | 3,4-dihydro-1H-isoquinolin-2-yl | —CO— | (±)CN | —CH₂CH₂CH₂— | 341 (M + H)⁺ |
| 158 | 3,4-dihydro-1H-isoquinolin-2-yl | —CO— | H | —CH₂OCH₂— | 318 (M + H)⁺ |
| 159 | 3,4-dihydro-1H-isoquinolin-2-yl | —CO— | H | —CH₂CH₂CH₂— | 326 (M + H)⁺ |
| 160 | 3,4-dihydro-2H-quinolin-1-yl | —CO— | CN | —CH₂CH₂— | 327 (M + H)⁺ |
| 161 | 3,4-dihydro-2H-quinolin-1-yl | —CO— | H | —SCH₂— | 320 (M + H)⁺ |
| 162 | 3,4-dihydro-2H-quinolin-1-yl | —CO— | H | —CH₂CH₂— | 302 (M + H)⁺ |
| 163 | 3,4-dihydro-2H-quinolin-1-yl | —CO— | (±)CN | —CH₂CH₂CH₂— | 341 (M + H)⁺ |

TABLE 25

| Example | A | D | R⁴ | E | ESI/MS (m/z) |
|---|---|---|---|---|---|
| 164 | 3,4-dihydro-2H-quinolin-1-yl | —CO— | H | —CH₂OCH₂— | 318 (M + H)⁺ |
| 165 | 3,4-dihydro-2H-quinolin-1-yl | —CO— | H | —CH₂CH₂CH₂— | 326 (M + H)⁺ |
| 166 | isoquinolin-3-yl | —NHCO— | CN | —CH₂CH₂— | 338 (M + H)⁺<br>336 (M − H)⁻ |
| 167 | isoquinolin-3-yl | —NHCO— | H | —SCH₂— | 331 (M + H)⁺ |
| 168 | isoquinolin-3-yl | —NHCO— | H | —CH₂CH₂— | 313 (M + H)⁺ |
| 169 | isoquinolin-3-yl | —NHCO— | (±)CN | —CH₂CH₂CH₂— | 352 (M + H)⁺ |
| 170 | isoquinolin-3-yl | —NHCO— | H | —CH₂OCH₂— | 329 (M + H)⁺ |
| 171 | isoquinolin-3-yl | —NHCO— | H | —CH₂CH₂CH₂— | 327 (M + H)⁺ |
| 172 | quinolin-2-yl | —NHCO— | CN | —CH₂CH₂— | 338 (M + H)⁺<br>336 (M − H)⁻ |
| 173 | quinolin-2-yl | —NHCO— | H | —SCH₂— | 331 (M + H)⁺ |
| 174 | quinolin-2-yl | —NHCO— | H | —CH₂CH₂— | 313 (M + H)⁺ |
| 175 | quinolin-2-yl | —NHCO— | (±)CN | —CH₂CH₂CH₂— | 352 (M + H)⁺ |
| 176 | quinolin-2-yl | —NHCO— | H | —CH₂OCH₂— | 329 (M + H)⁺ |
| 177 | quinolin-2-yl | —NHCO— | H | —CH₂CH₂CH₂— | 327 (M + H)⁺ |
| 178 | 2-methylquinolin-4-yl | —NHCO— | CN | —CH₂CH₂— | 352 (M + H)⁺ |
| 179 | 2-methylquinolin-4-yl | —NHCO— | H | —SCH₂— | 345 (M + H)⁺ |
| 180 | 2-methylquinolin-4-yl | —NHCO— | H | —CH₂CH₂— | 327 (M + H)⁺ |
| 181 | 2-methylquinolin-4-yl | —NHCO— | (±)CN | —CH₂CH₂CH₂— | 366 (M + H)⁺ |

TABLE 26

| Example | A | D | R⁴ | E | ESI/MS (m/z) |
|---|---|---|---|---|---|
| 182 | 2-methylquinolin-4-yl | —NHCO— | H | —CH₂CH₂CH₂— | 341 (M + H)⁺ |
| 183 | 3-methylquinolin-5-yl | —NHCO— | CN | —CH₂CH₂— | 353 (M + H)⁺ |
| 184 | 3-methylquinolin-5-yl | —NHCO— | H | —SCH₂— | 346 (M + H)⁺ |
| 185 | 3-methylquinolin-5-yl | —NHCO— | H | —CH₂CH₂— | 328 (M + H)⁺ |
| 186 | 3-methylquinolin-5-yl | —NHCO— | (±)CN | —CH₂CH₂CH₂— | 367 (M + H)⁺ |
| 187 | 3-methylquinolin-5-yl | —NHCO— | H | —CH₂OCH₂— | 344 (M + H)⁺ |
| 188 | 3-methylquinolin-5-yl | —NHCO— | H | —CH₂CH₂CH₂— | 342 (M + H)⁺ |
| 189 | 4-methyl-2-oxo-2H-chromen-7-yl | —NHCO— | CN | —CH₂CH₂— | 369 (M + H)⁺<br>367 (M − H)⁻ |
| 190 | 4-methyl-2-oxo-2H-chromen-7-yl | —NHCO— | H | —SCH₂— | 362 (M + H)⁺ |
| 191 | 4-methyl-2-oxo-2H-chromen-7-yl | —NHCO— | H | —CH₂CH₂— | 344 (M + H)⁺ |
| 192 | 4-methyl-2-oxo-2H-chromen-7-yl | —NHCO— | (±)CN | —CH₂CH₂CH₂— | 383 (M + H)⁺ |
| 193 | 4-methyl-2-oxo-2H-chromen-7-yl | —NHCO— | H | —CH₂OCH₂— | 360 (M + H)⁺ |
| 194 | 4-methyl-2-oxo-2H-chromen-7-yl | —NHCO— | H | —CH₂CH₂CH₂— | 358 (M + H)⁺ |

TABLE 26-continued

| Example | A | D | R⁴ | E | ESI/MS (m/z) |
|---|---|---|---|---|---|
| 195 | benzothiazol-2-yl | —NHCO— | CN | —CH₂CH₂— | 344 (M + H)⁺ |
| 196 | benzothiazol-2-yl | —NHCO— | H | —SCH₂— | 337 (M + H)⁺ |
| 197 | benzothiazol-2-yl | —NHCO— | H | —CH₂CH₂— | 319 (M + H)⁺ |
| 198 | benzothiazol-2-yl | —NHCO— | (±)CN | —CH₂CH₂CH₂— | 358 (M + H)⁺ |
| 199 | benzothiazol-2-yl | —NHCO— | H | —CH₂CH₂CH₂— | 333 (M + H)⁺ |

TABLE 27

| Example | A | D | R⁴ | E | ESI/MS (m/z) |
|---|---|---|---|---|---|
| 200 | 9H-purin-6-yl | —NHCO— | CN | —CH₂CH₂— | 329 (M + H)⁺ |
| 201 | 9H-purin-6-yl | —NHCO— | H | —SCH₂— | 322 (M + H)⁺ |
| 202 | 9H-purin-6-yl | —NHCO— | H | —CH₂CH₂— | 304 (M + H)⁺ |
| 203 | 9H-purin-6-yl | —NHCO— | (±)CN | —CH₂CH₂CH₂— | 343 (M + H)⁺ |
| 204 | 9H-purin-6-yl | —NHCO— | H | —CH₂CH₂CH₂— | 318 (M + H)⁺ |
| 205 | 2-methylsulfanyl[1,2,4]triazolo[1,5-a]pyrimidin-7-yl | —NHCO— | CN | —CH₂CH₂— | 375 (M + H)⁺ |
| 206 | 2-methylsulfanyl[1,2,4]triazolo[1,5-a]pyrimidin-7-yl | —NHCO— | H | —SCH₂— | 368 (M + H)⁺ |
| 207 | 2-methylsulfanyl[1,2,4]triazolo[1,5-a]pyrimidin-7-yl | —NHCO— | H | —CH₂CH₂— | 350 (M + H)⁺ |
| 208 | 2-methylsulfanyl[1,2,4]triazolo[1,5-a]pyrimidin-7-yl | —NHCO— | (±)CN | —CH₂CH₂CH₂— | 389 (M + H)⁺ |
| 209 | 2-methylsulfanyl[1,2,4]triazolo[1,5-a]pyrimidin-7-yl | —NHCO— | H | —CH₂CH₂CH₂— | 364 (M + H)⁺ |
| 210 | octahydroquinolin-1-yl | —CO— | CN | —CH₂CH₂— | 333 (M + H)⁺ |

PHARMACOLOGICAL TEST EXAMPLE 1

In screening of DPP-IV inhibitor, the following method using glycyl-proline-4-methylcumalyl-7-amide (Gly-Pro-MCA) as substrate was used.

A test substance (40 μl) in various concentrations dissolved in a measurement buffer (Tris-HCl buffer (25 mM), pH 7.4, containing sodium chloride (140 mM), calcium chloride (10 nM), 1% bovine serum albumin), and 150 μM Gly-Pro-MCA substrate (40 μl), were put into each well of a 96-well microtiter plate, then mixed and left at room temperature for 5 minutes. There after, human plasma (20 μl) diluted30-fold with the measurement buffer was added to each well, stirred and reacted at room temperature for 30 minutes in the dark. The reaction was terminated by adding 100 μl of 1 M acetate buffer, pH 4.2, and MCA released by the activity of DPP-IV was determined by measuring fluorescence at 465 nm obtained by excitation at 360 nm. The concentration (IC₅₀) at which 50% of the activity of DPP-IV was inhibited by the test substance was determined on the basis of the activity of DPP-IV calculated according to the following equation. The results are shown in Table 28. Isoleucyl thiazolidide (Compound A) described in a patent (WO97/40832) was used as comparative chemical.

Inhibitory activity on DPP-IV=100×(1−(Fs−Fb)/F100−Fb)
F100:fluorescence intensity obtained by reaction with plasma. Fb:fluorescence intensity of a blank where the reaction was carried out with the reaction terminating solution added. Fs:fluorescence intensity obtained by adding the test substance.

TABLE 28

| Compound (Example No.) | DPP-IV IC50 (μM) |
|---|---|
| 1 | 0.051 |
| 2 | 0.032 |
| 3 | 0.023 |
| 4 | 0.087 |
| 6 | 0.091 |
| 8 | 0.054 |
| 9 | 0.061 |
| 10 | 0.085 |
| 11 | 0.068 |
| 12 | 0.028 |
| 13 | 0.024 |
| 15 | 0.028 |
| 16 | 0.033 |
| 18 | 0.036 |
| 19 | 0.050 |
| 20 | 0.052 |
| 21 | 0.028 |
| 22 | 0.073 |
| 23 | 0.082 |
| 24 | 0.043 |
| 25 | 0.048 |
| 26 | 0.033 |
| 27 | 0.021 |
| 28 | 0.078 |
| 30 | 0.089 |
| 31 | 0.049 |
| 32 | 0.048 |
| 33 | 0.071 |
| 34 | 0.023 |
| 35 | 0.037 |
| 36 | 0.045 |
| 37 | 0.017 |
| 38 | 0.025 |
| 39 | 0.073 |
| 41 | 0.025 |
| 42 | 0.027 |
| 43 | 0.016 |
| 44 | 0.037 |
| 45 | 0.028 |
| 46 | 0.019 |
| 47 | 0.024 |

TABLE 28-continued

| Compound (Example No.) | DPP-IV IC50 (μM) |
|---|---|
| 48 | 0.031 |
| 49 | 0.020 |
| 50 | 0.020 |
| 51 | 0.026 |
| 53 | 0.048 |
| 55 | 0.024 |
| 56 | 0.030 |
| 57 | 0.035 |
| 59 | 0.050 |
| 61 | 0.010 |
| 62 | 0.027 |
| 63 | 0.018 |
| 64 | 0.024 |
| 65 | 0.011 |
| 66 | 0.050 |
| 67 | 0.007 |
| 68 | 0.016 |
| 69 | 0.021 |
| 70 | 0.032 |
| 71 | 0.002 |
| 72 | 0.039 |

TABLE 28-continued

| Compound (Example No.) | DPP-IV IC50 (μM) |
|---|---|
| 73 | 0.094 |
| 74 | 0.044 |
| 75 | 0.014 |
| 76 | 0.022 |
| 77 | 0.022 |
| 78 | 0.015 |
| 82 | 0.017 |
| 89 | 0.025 |
| 91 | 0.082 |
| 92 | 0.052 |
| 93 | 0.062 |
| 95 | 0.013 |
| 101 | 0.066 |
| 102 | 0.090 |
| 105 | 0.031 |
| 122 | 0.026 |
| 126 | 0.031 |
| Compound A | 0.225 |

From the results of this test, the compound of the present invention showed an $IC_{50}$ value of tens nM, and was found to have a stronger inhibitory activity on DPP-IV than Compound A (the $IC_{50}$:225 nM).

PHARMACOLOGICAL TEST EXAMPLE 2

Wistar/ST male rats (Japan SLC, Inc.) were acclimated for 5 days or more (8-week-old when used) and then fasted overnight. The compound (3 mg/kg) in Example 1, the compound (1 mg/kg) in Example 61 and Compound A (10 mg/kg) were orally administered in a volume of 5 ml/kg into rats respectively, and after 30 minutes, 20% glucose solution (5 ml/kg) (corresponding to glucose (1 g/kg).) was orally administered to each rat. From the tip end of each tail, blood was collected with time, and plasma was separated, and blood glucose and insulin levels were measured. The blood level was measured by using Glutest (Sanwa Kagaku Kenkyusho Co., Ltd.), and the plasma insulin level was measured by using a commercially available EAI kit (Shibayagi Co., Ltd.).

The results are shown in Table 29. The blood glucose level was expressed in terms of area-under-curve ($AUC_{0\text{-}60\ min}$) (min·mg/dl) from 0 min. after sugar administration to 60 minutes, wherein the blood glucose level in a sample obtained by blood collection before the test was substituted for the blood glucose level at 0 min. The plasma insulin level was indicated by the plasma insulin level (pg/ml) 10 minutes after administration of the compound.

TABLE 29

| Administration group | Blood glucose level (min · mg/dl) | Insulin (pg/ml) | Administration group | Blood glucose level (min · mg/dl) | Insulin (pg/ml) |
|---|---|---|---|---|---|
| Water | 8199 ± 235 | 1692 ± 583 | Water | 8208 ± 368 | 2008 ± 666 |
| Compound A | 6671 ± 161 | 2994 ± 310 | Compound A | 6769 ± 128 | 3670 ± 827 |
| Example 1 | 7024 ± 222 | 2745 ± 574 | Example 61 | 7055 ± 287 | 4093 ± 1050 |

From the results of this test, it was found that the compound of the present invention exhibits a blood glucose depressant action based on its insulin secretion potentiation.

As described above, the compound of the present invention is a compound which exhibits a potent inhibitory activity on DPP-IV, is chemically stable, is excellent in enzyme selectivity without side effects and the like, and is thus useful in treatment of diabetes (particularly type 2 diabetes), its related complications, obesity and the like.

The invention claimed is:

1. A compound represented by the general formula (I):

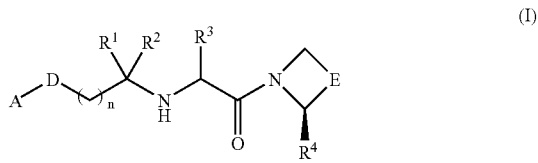

(I)

wherein $R^1$ and $R^2$ are the same or different and each represents a hydrogen atom, an optionally substituted C1-6 alkyl group, or —COOR$^5$ whereupon $R^5$ represents a hydrogen atom or an optionally substituted C1-6 alkyl group, or $R^1$ and $R^2$, together with a carbon atom to which they are bound, represent a 3- to 6-membered cycloalkyl group, $R^3$ represents a hydrogen atom or an optionally substituted C6-10 aryl group, $R^4$ represents a hydrogen atom or a cyano group, D represents —CONR$^6$—, —CO— or —NR$^6$CO—, $R^6$ represents a hydrogen atom or an optionally substituted C1-6 alkyl group, E represents —(CH$_2$)$_2$— or —SCH$_2$—, n is an integer of 0 to 3, and A represents an optionally substituted 6-5-system bicyclic heterocyclic group containing nitrogen in the 5-membered ring of the bicyclic heterocyclic group.

2. The compound according to claim 1, wherein in the general formula (I), each of $R^1$ and $R^2$ is a methyl group, $R^3$ is a hydrogen atom, $R^4$ is a cyano group, D is —CONH— or —CO—, E is —CH$_2$CH$_2$—, and n is 1 or 2.

3. The compound according to claim 2, wherein in the general formula (I), D is —CO—, and A is a 6-5-system bicyclic alicyclic heterocyclic group represented by the following formula:

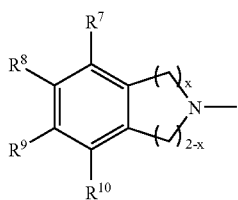

wherein x is an integer of 0 to 2, $R^7$, $R^8$, $R^9$ and $R^{10}$ are the same or different and each represents a hydrogen atom, a halogen atom, a hydroxy group, a trifluoromethyl group, an optionally substituted C1-6 alkyl group or an optionally substituted C1-6 alkoxy group.

4. The compound according to claim 2, wherein in the general formula (I), D is —CONH—, and A is a 6-5-system bicyclic heterocyclic group represented by the following formula:

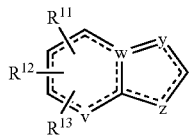

wherein ====represents a single or double bond, at least one of y, z, v and w is an oxygen, nitrogen or sulfur atom, $R^{11}$, $R^{12}$ and $R^{13}$ may be substituted on any hydrogen atoms on the ring, are the same or different and each represents a hydrogen atom, a hydroxy group, a trifluoromethyl group, a trifluoroacetyl group, an oxo group, an optionally substituted C1-6 alkyl group, an optionally substituted C1-6 alkoxy group, or an optionally substituted C6-10 aryl group.

5. The compound according to claim 4, wherein 1 to 3 groups out of y, z, v and w in the formula (III) are nitrogen atoms, and the remainder is a carbon atom.

6. The compound according to claim 4, wherein y in the formula (III) is nitrogen atom and each of w, x and z is a carbon atom.

7. The compound according to claim 4, wherein v, w and y in the formula (III) are nitrogen atoms and z is a carbon atom.

8. A pharmaceutical composition comprising as an active ingredient a compound represented by the general formula (I):

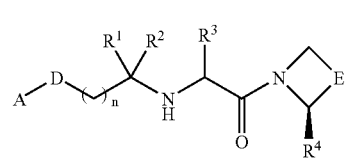

wherein $R^1$ and $R^2$ are the same or different and each represents a hydrogen atom, an optionally substituted C1-6 alkyl group, or —COOR$^5$ whereupon $R^5$ represents a hydrogen atom or an optionally substituted C1-6 alkyl group, or $R^1$ and $R^2$, together with a carbon atom to which they are bound, represent a 3- to 6-membered cycloalkyl group, $R^3$ represents a hydrogen atom or an optionally substituted C6-10 aryl group, $R^4$ represents a hydrogen atom or a cyano group, D represents —CONR$^6$—, —CO— or —NR$^6$CO—, $R^6$ represents a hydrogen atom or an optionally substituted C1-6 alkyl group, E represents —(CH$_2$)$_2$— or —SCH$_2$—, n is an integer of 0 to 3, and A represents an optionally substituted 6-5-system bicyclic heterocyclic group containing nitrogen in the 5-membered ring of the bicyclic heterocyclic group.

9. The pharmaceutical composition according to claim 8, wherein in the general formula (I), each of $R^1$ and $R^2$ is a methyl group, $R^3$ is a hydrogen atom, $R^4$ is a cyano group, D is —CONH— or —CO—, E is —CH$_2$CH$_2$—, and n is 1 or 2.

10. The pharmaceutical composition according to claim 9, wherein in the general formula (I), D is —CO—, and A is a 6-5-system bicyclic alicyclic heterocyclic group represented by the following formula:

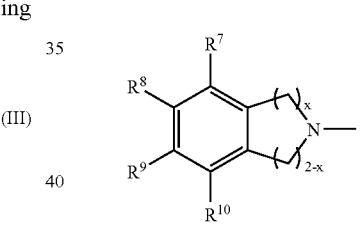

wherein x is an integer of 0 to 2, $R^7$, $R^8$, $R^9$ and $R^{10}$ are the same or different and each represents a hydrogen atom, a halogen atom, a hydroxy group, a trifluoromethyl group, an optionally substituted C1-6 alkyl group or an optionally substituted C1-6 alkoxy group.

11. The pharmaceutical composition according to claim 9, wherein in the general formula (I), D is —CONH—, and A is a 6-5-system bicyclic heterocyclic group represented by the following formula:

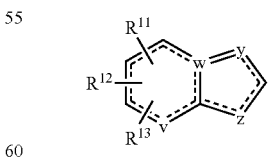

wherein ====represents a single or double bond, at least one of y, z, v and w is an oxygen, nitrogen or sulfur atom, $R^{11}$, $R^{12}$ and $R^{13}$ may be substituted on any hydrogen atoms on the ring, are the same or different and each represents a hydrogen atom, a hydroxy group, a trifluoromethyl group, a trifluoroacetyl group, an oxo group, an optionally substituted C1-6 alkyl group, an optionally substituted C1-6 alkoxy group, or an optionally substituted C6-10 aryl group.

12. The pharmaceutical composition according to claim 11, wherein 1 to 3 groups out of y, z, v and w in the formula (III) are nitrogen atoms, and the remainder is a carbon atom.

13. The pharmaceutical composition according to claim 11, wherein y in the formula (III) is a nitrogen atom and each of w, x and z is a carbon atom.

14. The pharmaceutical composition according to claim 11, wherein v, w and y in the formula (III) are nitrogen atoms and z is a carbon atom.

15. The pharmaceutical composition according to claim 8, which is for treatment of diabetes.

* * * * *